(12) United States Patent
Qin et al.

(10) Patent No.: US 6,972,124 B2
(45) Date of Patent: *Dec. 6, 2005

(54) PRECURSOR OF N-ACETYLGALACTOSAMINE-4-SULFATASE, METHODS OF TREATMENT USING SAID ENZYME AND METHODS FOR PRODUCING AND PURIFYING SAID ENZYME

(75) Inventors: Minmin Qin, Pleasanton, CA (US); Gary N. Zecherle, Novato, CA (US); Wai-Pan Chan, Castro Valley, CA (US); Paul A. Fitzpatrick, Albany, CA (US); Stuart Sweidler, Oakland, CA (US); John M. Henstrand, Oakland, CA (US); Dan J. Wendt, Walnut Creek, CA (US); Lin Chen, San Francisco, CA (US); Christopher M. Starr, Sonoma, CA (US)

(73) Assignee: BioMarin Pharmaceuticals Inc., Novato, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 10/704,365

(22) Filed: Nov. 7, 2003

(65) Prior Publication Data

US 2004/0131605 A1 Jul. 8, 2004

Related U.S. Application Data

(60) Continuation-in-part of application No. 10/658,699, filed on Sep. 9, 2003, and a continuation-in-part of application No. 10/290,908, filed on Nov. 7, 2002, now Pat. No. 6,866,844, which is a division of application No. 09/562,427, filed on May 1, 2000, now abandoned.

(51) Int. Cl.[7] .......................... A61K 38/46; C12N 9/16; C12N 1/20; C12N 5/00; A23J 1/00

(52) U.S. Cl. .................. 424/94.6; 435/196; 435/252.3; 435/320.1; 536/23.2; 530/412

(58) Field of Search .................. 424/94.6; 435/196, 435/252.3, 320.1, 94.6; 536/23.2; 530/412

(56) References Cited

FOREIGN PATENT DOCUMENTS

WO    WO 01/83722    11/2001

OTHER PUBLICATIONS

McGovern et al., J. Biol. Chem. (1982), 257 : 12605–12610.*
Brooke et al. et al. Biochimica et Biophysica Acta 1361 (1997) : 203–216.*
Anson et al. Biochem. J. (192) 284 : 789–794.*
Anson et al., "Correction of Human Mucopolysaccharidosis Type–VI Fibroblasts with Recombinant N–Acetylgalactosamine–4–Sulphatase," *Biochem J.*, 284:789–794 (1992).

Bielicki et al., "Advantages of Using Same Species Enzyme for Replacement Therapy in a Feline Model of Mucopolysaccharidosis Type VI," *J. Biol. Chem.*, 274:36335–36343 (1999).
Brooks et al., "Enzyme Replacement Therapy in Mucopolysaccharidosis VI: Evidence for Immune Response S and Alteed Efficacy of Treatment in Animal Models," *Biochem. Biophys. Acta.*, 1361:203–216 (1997).
Byers et al., "Effect of Enzyme Replacement Therapy on Bone Formation in a Feline Model of Mucopolysaccharidosis Type VI," *Bone*, 21:425–431 (1997).
Crawley et al., "Enzyme Replacement Therapy from Birth in a Feline Model of Mucopolysaccharidosis Type VI," *J. Clin. Invest.*, 99:651–662 (1997).
Crawley et al., " Enzyme Replacement Therapy from Birth in a Feline Model of Maroteaux–Lamy Syndrome," *J. Clin. Invest.*, 97:1864–1873 (1996).
Haskins et al., "Spinal Cord Compression and Hindlimb Paresis in Cats with Mucopolysaccharidosis VI," *J. Am. Vet. Med. Assoc.*, 182:983–985 (1983).
Haskins et al., "The Pathology of the Feline Model of Mucopolysaccharidosis VI," *Am. J. Pathol.*, 101:657–674 (1980).
Hoogerbrugge et al., "Allogenic Bone Marrow Transplantation for Lysosomal Storage Diseases," *Lancet*, 345:1398–1402 (1995).
Inherited Disease, eds., Scriver et al., New York:McGraw Hill, 1989, pp. 1565–1587.
Jezyk et al., "Mucopolysaccharidosis in a Cat with Arysulfatase B Deficiency: A Model of Maroteaux–Lamy Syndrome," *Science*, 198:834–836 (1977).
Konde et al., "Radiographically Visualized Skeletal Changes Associated with Mucopolysaccharidosis VI in Cats," *Vet. Radiol.*, 28:223–228 (1987).
Krivit et al., "Bone–Marrow Transplantation in the Maroteaux–Lamy Syndrome (Mucopolysaccharidosis Type VI)," *N. Eng. J. Med.*, 311:1606–1611 (1984).
Krivit et al., "Maroteaux–Lamy Syndrome—Treatment b, Allogenic Bone Marrow Transplantation in 6 Patients and Potential for Antotransplantation Bone Marrow Gene Insertion," *Intl. Ped.*, 7:47–52 (1992).

(Continued)

*Primary Examiner*—Tekchand Saidha
(74) *Attorney, Agent, or Firm*—Marshall, Gerstein & Borun LLP

(57) ABSTRACT

The present invention provides a highly purified recombinant human precursor N-acetylgalactosamine-4-sulfatase and biologically active mutants, fragments and analogs thereof as well as pharmaceutical formulations comprising highly purified recombinant human precursor N-acetylgalactosamine-4-sulfatase. The invention also provides methods for treating diseases caused all or in part by deficiencies in human N-acetylgalactosamine-4-sulfatase including MPS VI and methods for producing and purifying the recombinant precursor enzyme to a highly purified form.

5 Claims, 27 Drawing Sheets

OTHER PUBLICATIONS

McGovern et al., "Purification and Properties of Feline and Human Arylsulfatase B Isozymes," *J. Biol. Chem.*, 257:12605–12610 (1982).

Peters et al., "Phylogenetic Conservation of Arylsulfatase," *J. Biol. Chem.*, 265:3374–3381 (1990).

Roberts et al., "Development of a Procedure for Purification of a Recombinant Therapeutic Protein," *Australasian Biotechnol.*, 6:93–99 (1996).

Yogalingam et al., "Regulation of N–Acetylglactosamine–4–Sulfatase Expression in Retrovirus–Transduced Feline Mucopolysaccharidosis Type VI Muscle Cells.," *DNA Cell Biol.*, 18:187–195 (1999).

* cited by examiner

Outline of the rhASB Drug Substance Purification Process

Process Flow Chart - Sampling Plan

SDS-PAGE, 4-20% TG gel
Silver Stain 4-20% Polyacrylamide gradient SDS gels, stained with Coomassie R-250 or Silver 1 NEB Broad Range Prestained Standards
2 5 µg ASB AS60001 (Batch Process)
3 5 µg Ap60109UF4
4 5 µg Ap60109UF10
5 5 µg Ap60109UF15

4-20% Polyacrylamide gradient SDS gels, stained with Coomassie R-250 or Silver

1 NEB Broad Range Prestained Standards
2 5 μg ASB AS60001 (Batch Process)
3 5 μg Ap60109UF4
4 5 μg Ap60109UF10
5 5 μg Ap60109UF15
6 5 μg Ap60109UF18
7 5 μg Ap60109UF22
8 5 μg Ap60109UF25
9 5 μg Ap60109UF27

Formulated rhASb, 052202
5 ug/lane

1. AP60202 UF 4
2. AP60202 UF 10
3. AP60202 UF 18
4. AP60202 (BMK)
5. 102PD0139xB3
6. 102PD0139xB5
7. rhASB-202-002
8. 102PD0136 P1
9. 102PD0136 P2
10. Mark 12 Standard

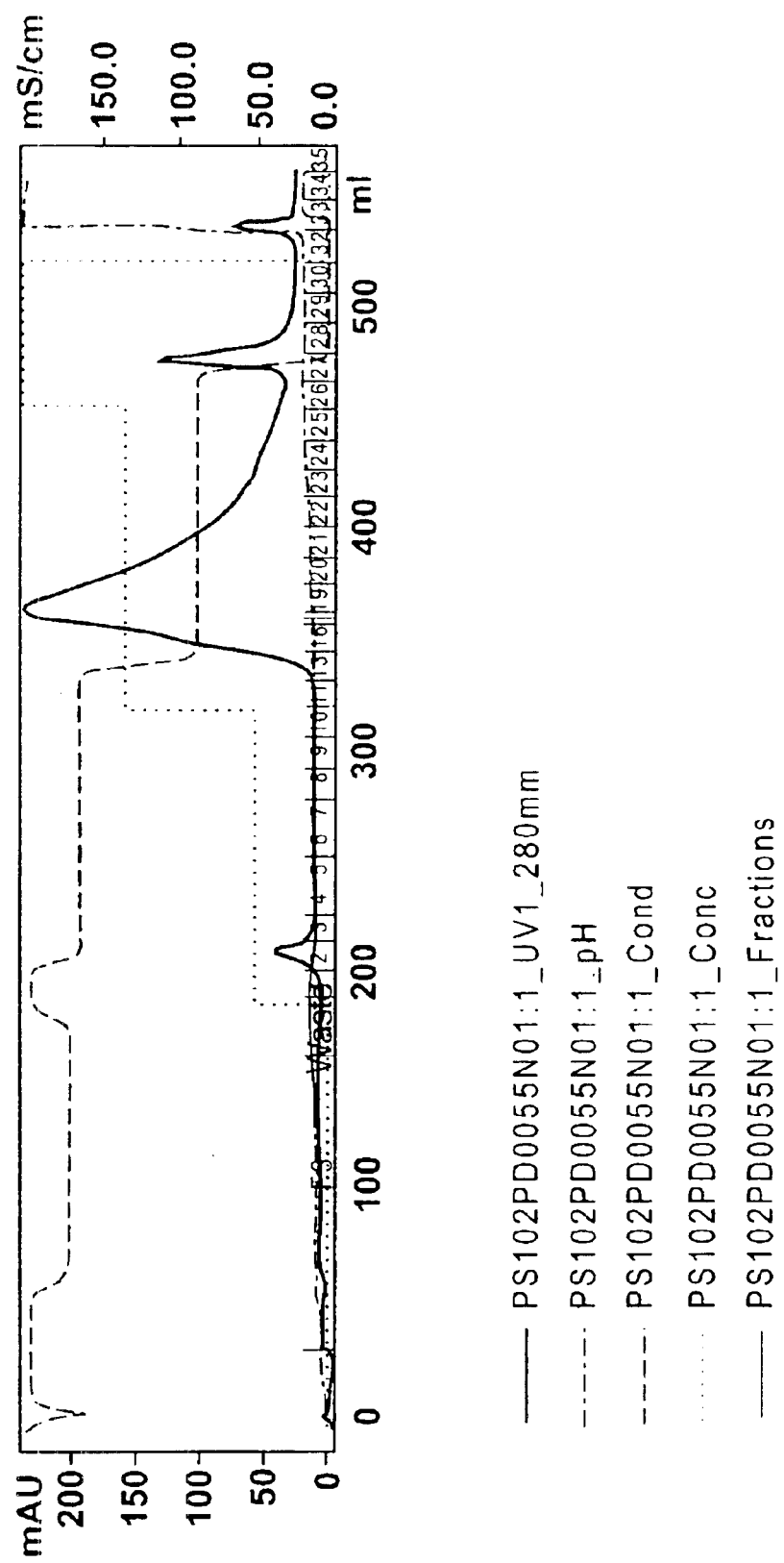

Western Blot, G-Anti-Cathepsin IgG, M19, 1:5,000
Donkey-Anti_goat IgG AP 1:5,000

SEQUENCE LISTING

<160> NUMBER OF SEQ ID NOS: 2

<210> SEQ ID NO 1
<211> LENGTH: 1656
<212> TYPE: DNA
<213> ORGANISM: Homo sapiens
<220> FEATURE:
<221> NAME/KEY: CDS
<222> LOCATION: (45)..(1643)

<400> SEQUENCE: 1

```
tagctacagt cggaaaccat cagcaagcag gtcattgttc caac atg ggt ccg cgc         56
                                                Met Gly Pro Arg
                                                 1 ggc gcg gcg agc ttg ccc cga ggc ccc gga cct cgg cgg ctg ctc ctc        104
Gly Ala Ala Ser Leu Pro Arg Gly Pro Gly Pro Arg Arg Leu Leu Leu
 5              10                  15                  20 ccc gtc gtc ctc ccg ctg ctg ctg ctg ttg ttg gcg ccg ccg ggc            152
Pro Val Val Leu Pro Leu Leu Leu Leu Leu Leu Ala Pro Pro Gly
                25                  30                  35 tcg ggc gcc ggg gcc agc cgg ccg ccc cac ctg gtc ttc ttg ctg gca        200
Ser Gly Ala Gly Ala Ser Arg Pro Pro His Leu Val Phe Leu Leu Ala
            40                  45                  50 gac gac cta ggc tgg aac gac gtc ggc ttc cac ggc tcc cgc atc cgc        248
Asp Asp Leu Gly Trp Asn Asp Val Gly Phe His Gly Ser Arg Ile Arg
        55                  60                  65 acg ccg cac ctg gac gcg ctg gcg gcc ggc ggg gtg ctc ctg gac aac        296
Thr Pro His Leu Asp Ala Leu Ala Ala Gly Gly Val Leu Leu Asp Asn
    70                  75                  80 tac tac acg cag ccg ctg tgc acg ccg tcg cgg agc cag ctg ctc act        344
Tyr Tyr Thr Gln Pro Leu Cys Thr Pro Ser Arg Ser Gln Leu Leu Thr
85                  90                  95                 100 ggc cgc tac cag atc cgt aca ggt tta cag cac caa ata atc tgg ccc        392
Gly Arg Tyr Gln Ile Arg Thr Gly Leu Gln His Gln Ile Ile Trp Pro
                105                 110                 115 tgt cag ccc agc tgt gtt cct ctg gat gaa aaa ctc ctg ccc cag ctc        440
Cys Gln Pro Ser Cys Val Pro Leu Asp Glu Lys Leu Leu Pro Gln Leu
            120                 125                 130 cta aaa gaa gca ggt tat act acc cat atg gtc gga aaa tgg cac ctg        488
Leu Lys Glu Ala Gly Tyr Thr Thr His Met Val Gly Lys Trp His Leu
        135                 140                 145 gga atg tac cgg aaa gaa tgc ctt cca acc cgc cga gga ttt gat acc        536
Gly Met Tyr Arg Lys Glu Cys Leu Pro Thr Arg Arg Gly Phe Asp Thr
    150                 155                 160 tac ttt gga tat ctc ctg ggt agt gaa gat tat tcc cat gaa cgc            584
Tyr Phe Gly Tyr Leu Leu Gly Ser Glu Asp Tyr Tyr Ser His Glu Arg
165                 170                 175                 180 tgt aca tta att gac gct ctg aat gtc aca cga tgt gct ctt gat ttt        632
```

```
Cys Thr Leu Ile Asp Ala Leu Asn Val Thr Arg Cys Ala Leu Asp Phe
            185                 190                 195 cga gat ggc gaa gaa gtt gca aca gga tat aaa aat atg tat tca aca       680
Arg Asp Gly Glu Glu Val Ala Thr Gly Tyr Lys Asn Met Tyr Ser Thr
            200                 205                 210 aac ata ttc acc aaa agg gct ata gcc ctc ata act aac cat cca cca       728
Asn Ile Phe Thr Lys Arg Ala Ile Ala Leu Ile Thr Asn His Pro Pro
            215                 220                 225 gag aag cct ctg ttt ctc tac ctt gct ctc cag tct gtg cat gag ccc       776
Glu Lys Pro Leu Phe Leu Tyr Leu Ala Leu Gln Ser Val His Glu Pro
        230                 235                 240 ctt cag gtc cct gag gaa tac ttg aag cca tat gac ttt atc caa gac       824
Leu Gln Val Pro Glu Glu Tyr Leu Lys Pro Tyr Asp Phe Ile Gln Asp
245                 250                 255                 260 aag aac agg cat cac tat gca gga atg gtg tcc ctt atg gat gaa gca       872
Lys Asn Arg His His Tyr Ala Gly Met Val Ser Leu Met Asp Glu Ala
                265                 270                 275 gta gga aat gtc act gca gct tta aaa agc agt ggg ctc tgg aac aac       920
Val Gly Asn Val Thr Ala Ala Leu Lys Ser Ser Gly Leu Trp Asn Asn
                280                 285                 290 acg gtg ttc atc ttt tct aca gat aac gga ggg cag act ttg gca ggg       968
Thr Val Phe Ile Phe Ser Thr Asp Asn Gly Gly Gln Thr Leu Ala Gly
            295                 300                 305 ggt aat aac tgg ccc ctt cga gga aga aaa tgg agc ctg tgg gaa gga      1016
Gly Asn Asn Trp Pro Leu Arg Gly Arg Lys Trp Ser Leu Trp Glu Gly
        310                 315                 320 ggc gtc cga ggg gtg ggc ttt gtg gca agc ccc ttg ctg aag cag aag      1064
Gly Val Arg Gly Val Gly Phe Val Ala Ser Pro Leu Leu Lys Gln Lys
325                 330                 335                 340 ggc gtg aag aac cgg gag ctc atc cac atc tct gac tgg ctg cca aca      1112
Gly Val Lys Asn Arg Glu Leu Ile His Ile Ser Asp Trp Leu Pro Thr
                345                 350                 355 ctc gtg aag ctg gcc agg gga cac acc aat ggc aca aag cct ctg gat      1160
Leu Val Lys Leu Ala Arg Gly His Thr Asn Gly Thr Lys Pro Leu Asp
                360                 365                 370 ggc ttc gac gtg tgg aaa acc atc agt gaa gga agc cca tcc ccc aga      1208
Gly Phe Asp Val Trp Lys Thr Ile Ser Glu Gly Ser Pro Ser Pro Arg
            375                 380                 385 att gag ctg ctg cat aat att gac cca aac ttc gtg gac tct tca ccg      1256
Ile Glu Leu Leu His Asn Ile Asp Pro Asn Phe Val Asp Ser Ser Pro
        390                 395                 400 tgt ccc agg aac agc atg gct cca gca aag gat gac tct tct ctt cca      1304
Cys Pro Arg Asn Ser Met Ala Pro Ala Lys Asp Asp Ser Ser Leu Pro
405                 410                 415                 420 gaa tat tca gcc ttt aac aca tct gtc cat gct gca att aga cat gga      1352
Glu Tyr Ser Ala Phe Asn Thr Ser Val His Ala Ala Ile Arg His Gly
                425                 430                 435 aat tgg aaa ctc ctc acg ggc tac cca ggc tgt ggt tac tgg ttc cct      1400
Asn Trp Lys Leu Leu Thr Gly Tyr Pro Gly Cys Gly Tyr Trp Phe Pro
                440                 445                 450 cca ccg tct caa tac aat gtt tct gag ata ccc tca tca gac cca cca      1448
Pro Pro Ser Gln Tyr Asn Val Ser Glu Ile Pro Ser Ser Asp Pro Pro
            455                 460                 465 acc aag acc ctc tgg ctc ttt gat att gat cgg gac cct gaa gaa aga      1496
Thr Lys Thr Leu Trp Leu Phe Asp Ile Asp Arg Asp Pro Glu Glu Arg
        470                 475                 480 cat gac ctg tcc aga gaa tat cct cac atc gtc aca aag ctc ctg tcc      1544
His Asp Leu Ser Arg Glu Tyr Pro His Ile Val Thr Lys Leu Leu Ser
485                 490                 495                 500
```

```
cgc cta cag ttc tac cat aaa cac tca gtc ccc gtg tac ttc cct gca    1592
Arg Leu Gln Phe Tyr His Lys His Ser Val Pro Val Tyr Phe Pro Ala
                505                 510                 515 cag gac ccc cgc tgt gat ccc aag gcc act ggg gtg tgg ggc cct tgg    1640
Gln Asp Pro Arg Cys Asp Pro Lys Ala Thr Gly Val Trp Gly Pro Trp
        520                 525                 530 atg taggatttca ggg                                                  1656
Met
```

<210> SEQ ID NO 2
<211> LENGTH: 533
<212> TYPE: PRT
<213> ORGANISM: Homo sapiens

<400> SEQUENCE: 2

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95

Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
            260                 265                 270

Met Asp Glu Ala Val Gly Asn Val Thr Ala Ala Leu Lys Ser Ser Gly
        275                 280                 285

Leu Trp Asn Asn Thr Val Phe Ile Phe Ser Thr Asp Asn Gly Gly Gln
    290                 295                 300

Thr Leu Ala Gly Gly Asn Asn Trp Pro Leu Arg Gly Arg Lys Trp Ser
305                 310                 315                 320
```

-continued

```
Leu Trp Glu Gly Gly Val Arg Gly Val Gly Phe Val Ala Ser Pro Leu
            325                 330                 335

Leu Lys Gln Lys Gly Val Lys Asn Arg Glu Leu Ile His Ile Ser Asp
            340             345                 350

Trp Leu Pro Thr Leu Val Lys Leu Ala Arg Gly His Thr Asn Gly Thr
        355                 360                 365

Lys Pro Leu Asp Gly Phe Asp Val Trp Lys Thr Ile Ser Glu Gly Ser
    370                 375                 380

Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
            405                 410                 415

Ser Ser Leu Pro Glu Tyr Ser Ala Phe Asn Thr Ser Val His Ala Ala
            420                 425                 430

Ile Arg His Gly Asn Trp Lys Leu Leu Thr Gly Tyr Pro Gly Cys Gly
        435                 440                 445

Tyr Trp Phe Pro Pro Ser Gln Tyr Asn Val Ser Glu Ile Pro Ser
    450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
            485                 490                 495

Lys Leu Leu Ser Arg Leu Gln Phe Tyr His Lys His Ser Val Pro Val
            500                 505                 510

Tyr Phe Pro Ala Gln Asp Pro Arg Cys Asp Pro Lys Ala Thr Gly Val
        515                 520                 525

Trp Gly Pro Trp Met
        530
```

PRECURSOR OF N-ACETYLGALACTOSAMINE-4-SULFATASE, METHODS OF TREATMENT USING SAID ENZYME AND METHODS FOR PRODUCING AND PURIFYING SAID ENZYME

This is a continuation-in-part of U.S. Ser. No. 10/290,908 filed Nov. 7, 2002 now U.S. Pat. No. 6,866,844 and a continuation-in-part of U.S. Ser. No. 10/658,699 filed Sep. 9, 2003, which in turn is a divisional of U.S. Ser. No. 09/562,427 filed May 1, 2000, now abandoned each of which is incorporated by reference herein in its entirety.

FIELD OF THE INVENTION

The present invention is in the field of clinical medicine, biochemistry and molecular biology. The present invention features therapeutics and methods for treating mucopolysaccharidosis VI as well as production and purification procedures for producing such therapeutics.

BACKGROUND OF THE INVENTION

MPS VI (Maroteaux-Lamy syndrome) is a lysosomal storage disease in which the affected patients lack the enzyme N-acetylgalactosamine-4-sulfatase (ASB). The enzyme metabolizes the sulfate moiety of glycosaminoglycan (GAG) dermatan sulfate (Neufeld, et al., "The mucopolysaccharidoses" The Metabolic Basis of Inherited Disease, eds. Scriver et al., New York:McGraw-Hill, 1989, p. 1565–1587). In the absence of the enzyme, the stepwise degradation of dermatan sulfate is blocked and the substrate accumulates intracellularly in the lysosome in a wide range of tissues. The accumulation causes a progressive disorder with multiple organ and tissue involvement in which the infant appears normal at birth, but usually dies before puberty. The diagnosis of MPS VI is usually made at 6–24 months of age when children show progressive deceleration of growth, enlarged liver and spleen, skeletal deformities, coarse facial features, upper airway obstruction, and joint deformities. Progressive clouding of the cornea, communicating hydrocephalus, or heart disease may develop in MPS VI children. Death usually results from respiratory infection or cardiac disease. Distinct from MPS I, MPS VI is not typically associated with progressive impairment of mental status, although physical limitations may impact learning and development. Although most MPS VI patients have the severe form of the disease that is usually fatal by the teenage years, affected patients with a less severe form of the disease have been described which may survive for decades.

Several publications provide estimates of MPS VI incidence. A 1990 British Columbia survey of all births between 1952 and 1986 published by Lowry et al (Lowry, et al., Human Genet 85:389–390 (1990)) estimates an incidence of just 1:1,300,000. An Australian survey (Meikle et al., JAMA 281(3):249–54) of births between 1980–1996 found 18 patients for an incidence of 1:248,000. A survey in Northern Ireland (Nelson, et al., Hum. Genet. 101:355–358 (1997)) estimated an incidence of 1:840,000. Finally, a survey from The Netherlands from 1970–1996 calculated a birth prevalence of 0.24 per 100,000 (Poorthuis, et al., Hum. Genet. 105:151–156 (1999)). Based on these surveys, it is estimated that there are between 50 and 300 patients in the U.S. who are diagnosed with all forms of this syndrome.

There is no satisfactory treatment for MPS VI although a few patients have benefited from bone marrow transplantation (BMT)(Krivit, et al., N. Engl. J. Med. 311(25):1606–11 (1984); Krivit, et al., Int. Pediat. 7:47–52 (1992)). BMT is not universally available for lack of a suitable donor and is associated with substantial morbidity and mortality. The European Group for Bone Marrow Transplantation reported transplant-related mortality of 10% (HLA identical) to 20–25% (HLA mismatched) for 63 transplantation cases of lysosomal disorders (Hoogerbrugge, et al., Lancet 345: 1398–1402 (1995)). Other than BMT, most patients receive symptomatic treatment for specific problems as their only form of care. It is an object of the present invention to provide enzyme replacement therapy with recombinant human N-acetylgalactosamine-4-sulfatase (rhASB). No attempts to treat humans with rhASB have been made. Likewise, no acceptable clinical dosages or medical formulations have been provided. Several enzyme replacement trials in the feline MPS VI model have been conducted.

SUMMARY OF THE INVENTION

The present invention encompasses the production, purification, and the use of a composition comprising a highly purified N-acetylgalactosamine-4-sulfatase in the precursor form. The DNA and encoded amino acid sequence of the precursor form is set forth in SEQ ID NOS: 1 and 2, respectively. The signal sequence is predicted to be amino acids 1–38 of SEQ ID NO: 2, and recombinant production has resulted in product commencing at either amino acid residue 39 or 40 of SEQ ID NO: 2.

In a first aspect, the present invention features novel methods of treating diseases caused all or in part by a deficiency in N-acetylgalactosamine-4-sulfatase (ASB). A method comprises administering an effective amount of a pharmaceutical composition to a subject in need of such treatment. In the preferred embodiment, the pharmaceutical composition comprises highly purified N-acetylgalactosamine-4-sulfatase in the precursor form, or a biologically active fragment, mutant or analog thereof alone or in combination with a pharmaceutically suitable carrier. The subject suffers from a disease caused all or in part by a deficiency of N-acetylgalactosamine-4-sulfatase. In other embodiments, this method features transferring a nucleic acid encoding all or a part of an N-acetylgalactosamine-4-sulfatase (ASB) or a biologically active mutant or analog thereof into one or more host cells in vivo. Preferred embodiments include optimizing the dosage to the needs of the organism to be treated, preferably mammals or humans, to effectively ameliorate the disease symptoms. In preferred embodiments the disease is mucopolysaccharidosis VI (MPS V1) or Maroteaux-Lamy syndrome.

This first aspect of the invention specifically provides methods of treating humans suffering from diseases caused all or in part by a deficiency in ASB activity by administering a therapeutically effective amount of human ASB, preferably recombinant human ASB. Thus, the invention contemplates use of human ASB in preparation of a medicament for the treatment of a deficiency in ASB activity, as well as a pharmaceutical composition containing human ASB for use in treating a deficiency in ASB activity. The deficiency in ASB activity can be observed, e.g., as activity levels of 50% or less, 25% or less, or 10% or less compared, to normal levels of ASB activity and can manifest as a mucopolysaccharidosis, for example mucopolysaccharidosis VI (MPS VI) or Maroteaux-Lamy syndrome. The therapeutically effective amount is an amount sufficient to provide a beneficial effect in the human patient and preferably provides improvements in any one of the following: joint mobility, pain, or stiffness, either subjectively or objectively; exercise tolerance or endurance, for example, as measured by walking or climbing ability; pulmonary function, for example, as measured by FVC, $FEV_1$ or FET; visual acuity; or activities of daily living, for example, as measured by ability to stand up from sitting, pull clothes on or off, or pick up small objects. The human ASB is preferably administered as a highly purified recombinant preparation as described herein. Preferred preparations contain rhASB with a purity greater than 95%, 96%, 97%, 98%, 99%, 99.2%, 99.5%, 99.6%, 99.7%, 99.8%, or 99.9%, as measured by reverse-phase HPLC. Preferred preparations also contain the precursor form of ASB at high purity, so that processed forms of ASB are not detected on Coomassie-stained SDS-PAGE. Most preferably the purity of the precursor form of ASB is greater than 95%, 95%, 96%, 97%, 98%, 99%, 99.2%, 99.5%, 99.6%, 99.7%, 99.8%, or 99.9%, as measured, by size exclusion chromatography (SEC)-HPLC. The human ASB is also preferably formulated with a surfactant or non-ionic detergent as described herein, optionally excluding a formulation with polyoxyethylene sorbitan 20 or 80 at 0.001%.

Administration of rhASB at doses below 1 mg/kg per week, e.g. at 0.2 mg/kg per week, has been found to have a beneficial effect. The invention contemplates doses of at least 0.1 mg/kg, 0.2 mg/kg, 0.5 mg/kg, 0.75 mg/kg, 1 mg/kg, or 1.5 mg/kg per week, and may range up to 2 mg/kg, 4 mg/kg, 5 mg/kg or higher per week. The preferred dose is 1 mg/kg/week. Such doses are preferably delivered once weekly but optionally may be divided in equal amounts over more frequent time periods such as biweekly or daily. A variety of parenteral or nonparenteral routes of administration, including oral, transdermal, transmucosal, intrapulmonary (including aerosolized), intramuscular, subcutaneous, or intravenous that deliver equivalent dosages are contemplated. Administration by bolus injection or infusion directly into the joints or CSF is also specifically contemplated, such as intrathecal, intracerebral, intraventricular, via lumbar puncture, or via the cisterna magna. A variety of means are known in the art for achieving such intrathecal administration, including pumps, reservoirs, shunts or implants. Preferably the doses are delivered via intravenous infusions lasting 1, 2 or 4 hours, most preferably 4 hours, but may also be delivered by an intravenous bolus.

Other means of increasing ASB activity in the human subjects are also contemplated, including gene therapy that causes the patient to transiently or permanently increase expression of exogenous or endogenous ASB. Transfer of an exogenous hASB gene or a promoter that increases expression of the endogenous hASB gene is possible through a variety of means known in the art, including viral vectors, homologous recombination, or direct DNA injection.

In a second aspect, the present invention features novel pharmaceutical compositions comprising an N-acetylgalactosamine-4-sulfatase (ASB) or a biologically active fragment, mutant or analog thereof useful for treating a disease caused all or in part by a deficiency in N-acetylgalactosamine-4-sulfatase (ASB). In the preferred embodiment, the N-acetylgalactosamine-4-sulfatase is precursor N-acetylgalactosamine-4-sulfatase. Such compositions may be suitable for administration in a number of ways such as parenteral, topical, intranasal, inhalation or oral administration. Within the scope of this aspect are embodiments featuring nucleic acid sequences encoding all or a part of an N-acetylgalactosamine-4-sulfatase (ASB) which may be administered in vivo into cells affected with an N-acetylgalactosamine-4-sulfatase (ASB) deficiency.

In a third aspect, the present invention features a method to produce an N-acetylgalactosamine-4-sulfatase (ASB) or a biologically active fragment, mutant or analog thereof in amounts which enable using the enzyme therapeutically. In a broad embodiment, the method comprises the step of transfecting a cDNA encoding for all or a part of a N-acetylgalactosamine-4-sulfatase (ASB) or a biologically active mutant or analog thereof into a cell suitable for the expression thereof. In the preferred embodiment, the cells are grown in a constant or continuous culture or in perfusion. In another embodiment, the cells are grown in a medium that lacks G418. In some embodiments, a cDNA encoding for a complete N-acetylgalactosamine-4-sulfatase (ASB) is used, preferably a human N-acetylgalactosamine-4-sulfatase (ASB). However, in other embodiments, a cDNA encoding for a biologically active fragment or mutant thereof may be used. Specifically, one or more amino acid substitutions may be made while preserving or enhancing the biological activity of the enzyme. In other preferred embodiments, an expression vector is used to transfer the cDNA into a suitable cell or cell line for expression thereof. In one particularly preferred embodiment, the cDNA is transfected into a Chinese Hamster Ovary (CHO) cell, such as the CHO-K1 cell line. In yet other preferred embodiments, the production procedure comprises the following steps: (a) growing cells transfected with a DNA encoding all or a biologically active fragment or mutant of a human N-acetylgalactosamine-4-sulfatase in a suitable growth medium to an appropriate density, (b) introducing the transfected cells into a bioreactor, (c) supplying a suitable growth medium to the bioreactor, and (d) separating the transfected cells from the media containing the enzyme.

In a fourth aspect, the present invention provides a transfected cell line which features the ability to produce N-acetylgalactosamine-4-sulfatase (ASB) in amounts which enable using the enzyme therapeutically. In a preferred embodiment, the N-acetylgalactosamine-4-sulfatase is precursor N-acetylgalactosamine-4-sulfatase. In preferred embodiments, the present invention features a recombinant CHO cell line such as the CHO K1 cell line that stably and reliably produces amounts of an N-acetylgalactosamine-4-sulfatase (ASB) or a biologically active fragment, mutant or analog thereof which enable using the enzyme therapeutically. Especially preferred is the transgenic CHO-K1, cell line designated CSL4S-342. In some preferred embodiments, the transgenic cell line contains one or more copies of an expression construct. Preferably, the transgenic cell line contains about 10 or more copies of the expression construct. In even more preferred embodiments, the cell line expresses the recombinant N-acetylgalactosamine-4-sulfatase (ASB) or a biologically active fragment, mutant or analog thereof in amounts of at least about 20–40 micrograms per $10^7$ cells per day.

In a fifth aspect, the present invention provides novel vectors suitable to produce N-acetylgalactosamine-4-sulfatase (ASB) or a biologically active fragment, mutant or analog thereof in amounts which enable using the enzyme therapeutically.

In a sixth aspect, the present invention provides novel N-acetylgalactosamine-4-sulfatase (ASB) or a biologically active fragment, mutant or analog thereof produced in accordance with the methods of the present invention and thereby present in amounts which enable using the enzyme therapeutically. The specific activity of the N-acetylgalactosamine-4-sulfatase (ASB) according to the present invention is preferably in the range of 20–90 units, and more preferably greater than about 50units per mg protein. In the preferred embodiment, the N-acetylgalactosamine-4-sulfatase is highly purified precursor N-acetylgalactosamine-4-sulfatase.

In a seventh aspect, the present invention features a novel method to purify N-acetylgalactosamine-4-sulfatase (ASB) or a biologically active fragment, mutant or analog thereof. According to a first embodiment, a transfected cell mass is grown and removed leaving recombinant enzyme. Exogenous materials should normally be separated from the crude bulk to prevent fouling of the columns. Preferably, the growth medium containing the recombinant enzyme is passed through an ultrafiltration step. In another preferred embodiment, the method to purify the precursor N-acetylgalactosamine-4-sulfatase comprises: (a) obtaining a fluid containing precursor N-acetylgalactosamine-4-sulfatase; (b) reducing the proteolytic activity of a protease in said fluid able to cleave the precursor N-acetylgalactosamine-4-sulfatase, wherein said reducing does not harm said precursor N-acetylgalactosamine-4-sulfatase; (c) contacting the fluid with a Cibracon blue dye interaction chromatography resin; (d) contacting the fluid with a copper chelation chromatography resin; (e) contacting the fluid with a phenyl hydrophobic interaction chromatography resin; (f) recovering said precursor N-acetylgalactosamine-4-sulfatase. Preferably, steps (c), (d) and (e) can be performed sequentially. Those skilled in the art readily appreciate that one or more of the chromatography steps may be omitted or substituted, or that the order of the chromatography steps may be changed within the scope of the present invention. In other preferred embodiments, the eluent from the final chromatography column is ultrafiltered/diafiltered, and an appropriate step is performed to remove any remaining viruses. Finally, appropriate sterilizing steps may be performed as desired.

DESCRIPTION OF THE FIGURES

FIGS. 8A–8C depicts profiles obtained for the Blue Sepharose Column (FIG. 8A), Copper Chelating Sepharose Column (FIG. 8B) and Phenyl Sepharose Column (FIG. 8C). In FIG. 8B, cathepsin activity is indicated by the red line.

DETAILED DESCRIPTION OF THE INVENTION

Figure 1:
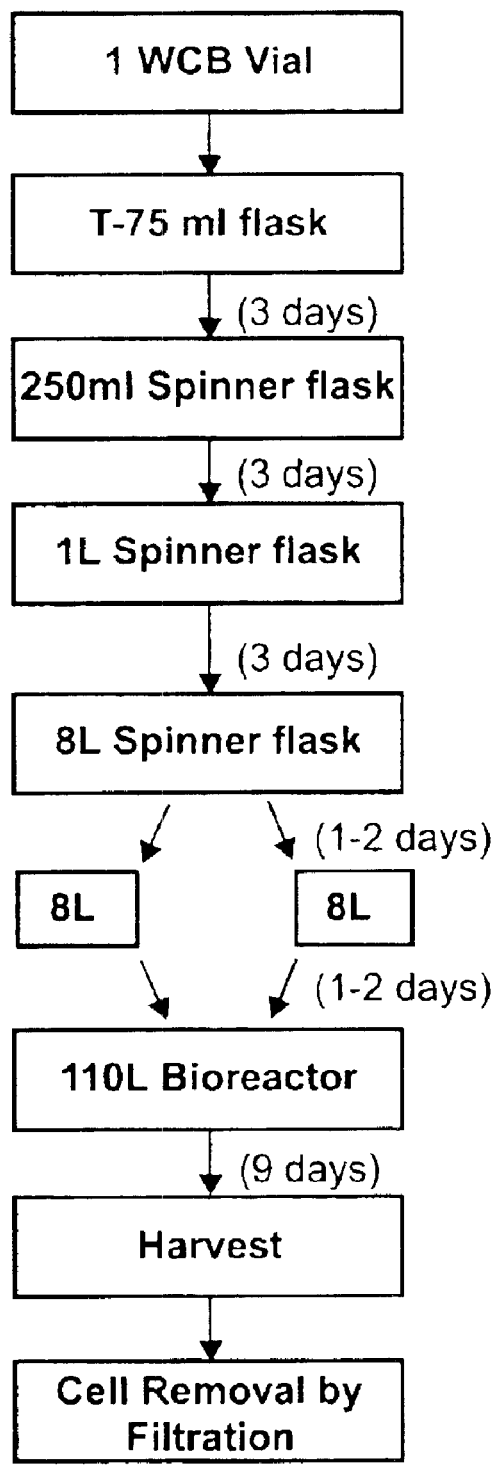
FIG. 1 provides a flow diagram of the method for producing a human N-acetylgalactosamine-4-sulfatase (ASB) according to the present invention.

The present invention encompasses the production, purification, and the use of a composition comprising a highly purified N-acetylgalactosamine-4-sulfatase in the precursor form. The purity of N-acetylgalactosamine-4-sulfatase in the precursor form is at least equal to or greater than 95, 96, 97 or 98% by total protein as determined by the reverse-phase HPLC method. Preferably, the purity is at least equal to or greater than 99%. More preferably, the purity is at least equal to or greater than 99.1, 99.2, 99.3 or 99.4%. Even more preferably, the purity is at least equal to, or greater than 99.5, 99.6, 99.7 or 99.8%. Even much more preferably, the purity is at least equal to or greater than 99.9%. The purity of precursor N-acetylgalactosamine-4-sulfatase is measured using the reverse-phase HPLC method (see Example 9). The purity of precursor N-acetylgalactosamine-4-sulfatase is that whereby the composition essential free of any contaminating cell proteins or degraded or mature or processed N-acetylgalactosamine-4-sulfatase that is detectable by the reverse-phase HPLC method. All percent purity is based on total protein as determined by the reverse-phase HPLC method. The consistently repeatable high purity obtainable using the purification process disclosed herein makes it possible to treat these patients that require long-term, chronic treatment with high purity rhASB preparations administered at every treatment, e.g., weekly. Thus, the invention contemplates administering precursor rhASB of such high purity over a long period of time, e.g. 12 weeks, 24 weeks, 48 weeks, 96 weeks or more.

In a first aspect, the present invention features novel methods of treating diseases caused all or in part by a deficiency in N-acetylgalactosamine-4-sulfatase (ASB). In one embodiment, this method features administering a recombinant N-acetylgalactosamine-4-sulfatase (ASB) or a biologically active fragment, mutant or analog thereof alone or in combination with a pharmaceutically suitable carrier. In other embodiments, this method features transferring a nucleic acid encoding, all or a part of an N-acetylgalactosamine-4-sulfatase (ASB) or a biologically active mutant thereof into one or more host cells in vivo. Preferred embodiments include optimizing the dosage to the needs of the organism to be treated, preferably mammals or humans, to effectively ameliorate the disease symptoms. In preferred embodiments the disease is mucopolysaccharidosis VI (MPS V1), Maroteaux-Lamy syndrome.

The purity of precursor N-acetylgalactosamine-4-sulfatase is that whereby the composition is essentially free of any contaminating cell proteins which can cause an immunological or allergic reaction by the subject who is administered precursor N-acetylgalactosamine-4-sulfatase. A composition is essentially free of such contaminating host cell proteins if the composition, when administered to a subject, does not cause any immunological or allergic reaction. The high purity of the precursor N-acetylgalactosamine-4-sulfatase is important for avoiding an immunological or allergic reaction by the subject to the impurities present in the pharmaceutical composition. This is especially true of proteins of the cells from which the precursor N-acetylgalactosamine-4-sulfatase is purified. When recombinant precursor N-acetylgalactosamine-4-sulfatase is expressed and purified from Chinese Hamster Ovary cells, the Chinese Hamster Ovary proteins can cause immunological or allergic reactions (e.g. hives) in the subject. The only means to avoid this type of reaction is to ensure that the precursor N-acetylgalactosamine-4-sulfatase is sufficiently pure so that the contaminating Chinese Hamster Ovary proteins are not of sufficient amount to cause such reaction(s). The purity of the pharmaceutical composition is especially important as subjects include patients suffering from MPS VI and are thus already immunologically compromised.

Also preferably the purity of the precursor N-acetylgalactosamine-4-sulfatase (ASB) is such that the composition has only trace amounts of processed or degraded forms. Proteases present in the host cells cleave the N-acetylgalactosamine-4-sulfatase into lower molecular weight forms. While some of these forms may also be enzymatically active, the precursor form is preferable for cellular uptake and lysosomal targeting and thus a higher amount of non-processed precursor ASB in the final preparation is desirable. Moreover, degraded forms of ASB in the drug product may also engender higher incidence or amounts of antibodies to ASB itself, which is highly undesirable in cases such as this where long-term therapy of patients is required. The perfusion purification process described herein results in a highly pure preparation that is essentially free of contaminating host cell proteins or processed/aggregated forms of ASB as assayed by the combination of SDS-PAGE, RPHPLC and SEC-HPLC. When administered to humans, the product produced by this process appears to have a longer half-life.

The indication for recombinant human N-acetylgalactosamine-4-sulfatase (rhASB) is for the treatment of MPS VI, also known as Maroteaux-Lamy Syndrome. According to preferred embodiments, an initial dose of 1 mg/kg (~50 U/kg) is provided to patients suffering from a deficiency in N-acetylgalactosamine-4-sulfatase. Preferably, the N-acetylgalactosamine-4-sulfatase is administered weekly by injection. According to other preferred embodiments, patients who do not demonstrate a reduction in urinary glycosaminoglycan excretions of at least fifty percent are changed to a dosage of 2 mg/kg (~100 U/kg) within about three months of initial dosage. Preferably, the N-acetylgalactosamine-4-sulfatase (rhASB) or a biologically active fragment, mutant or analog thereof is administered intravenously over approximately a four-hour period once weekly preferably for as long as significant clinical symptoms of disease persist. Also, preferably, the N-acetylgalactosamine-4-sulfatase (rhASB) is administered by an intravenous catheter placed in the cephalic or other appropriate vein with an infusion of saline begun at about 30 cc/hr. Further, preferably the N-acetylgalactosamine-4-sulfatase (rhASB) is diluted into about 250 cc of normal saline.

In a second aspect, the present invention features novel pharmaceutical compositions comprising human N-acetylgalactosamine-4-sulfatase (rhASB) or a biologically active fragment, mutant or analog thereof useful for treating a deficiency in N-acetylgalactosamine-4-sulfatase. The recombinant enzyme may be administered in a number of ways in addition to the preferred embodiments described above, such as parenteral, topical, intranasal, inhalation or oral administration. Another aspect of the invention is to provide for the administration of the enzyme by formulating it with a pharmaceutically-acceptable carrier which may be solid, semi-solid or liquid or an ingestable capsule. Examples of pharmaceutical compositions include tablets, drops such as nasal drops, compositions for topical application such as ointments, jellies, creams and suspensions, aerosols for inhalation, nasal spray, liposomes. Usually the recombinant enzyme comprises between 0.05 and 99% or between 0.5 and 99% by weight of the composition, for example between 0.5 and 20% for compositions intended for injection and between 0.1 and 50% for compositions intended for oral administration.

To produce pharmaceutical compositions in this form of dosage units for oral application containing a therapeutic enzyme, the enzyme may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes and compressed to form tablets or cores for dragees. If dragees are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the composition of soft gelatine capsules consisting of gelatine and, for example, glycerol as a plasticizer, or similar closed capsules, the active substance may be admixed with a Carbowax or a suitable oil as e.g., sesame oil, olive oil, or arachis oil. Hard gelatine capsules may contain granulates of the active substance with solid, pulverulent carriers such as lactose, saccharose, sorbitol, mannitol, starches such as potato starch, corn starch or amylopectin, cellulose derivatives or gelatine, and may also include magnesium stearate or stearic acid as lubricants.

Therapeutic enzymes of the present invention may also be administered parenterally such as by subcutaneous, intramuscular or intravenous injection either by single injection or pump infusion or by sustained release subcutaneous implant, and therapeutic enzymes may be administered by inhalation. In subcutaneous, intramuscular and intravenous injection the therapeutic enzyme (the active ingredient) may be dissolved or dispersed in a liquid carrier vehicle. For parenteral administration the active material may be suitably admixed with an acceptable vehicle, preferably of the vegetable oil variety such as peanut oil, cottonseed oil and the like. Other parenteral vehicles such as organic compositions using solketal, glycerol, formal, and aqueous parenteral formulations may also be used.

For parenteral application by injection, compositions may comprise an aqueous solution of a water soluble pharmaceutically acceptable salt of the active acids according to the invention, desirably in a concentration of 0.5–10%, and optionally also a stabilizing agent and/or buffer substances in aqueous solution: Dosage units of the solution may advantageously be enclosed in ampoules.

When therapeutic enzymes are administered in the form of a subcutaneous implant, the compound, is suspended or dissolved in a slowly dispersed material known to those skilled in the art, or administered in a device which slowly releases the active material through the use of a constant driving-force such as an osmotic pump. In such cases administration over an extended period of time is possible.

For topical application, the pharmaceutical compositions are suitably in the form of an ointment, cell, suspension, cream or the like. The amount of active substance may vary, for example between 0.05–20% by weight of the active substance. Such pharmaceutical compositions for topical application may be prepared in known manner by mixing, the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are, e.g., dimethylacetamide (U.S. Pat. No. 3,472,931), trichloro ethanol or trifluoroethanol (U.S. Pat. No. 3,891,757), certain alcohols and mixtures thereof (British Patent No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the therapeutic enzyme containing pharmaceutical compositions are administered may vary within a wide range and will depend on various factors such as for example the severity of the disease, the age of the patient, etc., and may have to be individually adjusted. As a possible range for the amount of therapeutic enzyme which may be administered per day be mentioned from about 0.1 mg- to about 2000 mg or from about 1 mg to about 2000 mg.

The pharmaceutical compositions containing the therapeutic enzyme may suitably be formulated so that they provide doses within these ranges either as single dosage units or as multiple dosage units. In addition to containing a therapeutic enzyme (or therapeutic enzymes), the subject formulations may contain one or more substrates or cofactors for the reaction catalyzed by the therapeutic enzyme in the compositions. Therapeutic enzyme containing, compositions may also contain more than one therapeutic enzyme. Likewise, the therapeutic enzyme may be in conjugate form being bound to another moiety, for instance PEG. Additionally, the therapeutic enzyme may contain one or more targeting moieties or transit peptides to assist delivery to a tissue, organ or organelle of interest.

The recombinant enzyme employed in the subject methods and compositions may also be administered by means of transforming patient cells with nucleic acids encoding the N-acetylgalactosamine-4-sulfatase or a biologically active fragment, mutant or analog thereof. The nucleic acid sequence so encoding may be incorporated into a vector for transformation into cells of the patient to be treated. Preferred embodiments of such vectors are described herein. The vector may be designed so as to integrate into the chromosomes of the subject, e.g., retroviral vectors, or to replicate autonomously in the host cells. Vectors containing encoding N-acetylgalactosamine-4-sulfatase nucleotide sequences may be designed so as to provide for continuous or regulated expression of the enzyme. Additionally, the genetic vector encoding the enzyme may be designed so as to stably integrate into the cell genome or to only be present transiently. The general methodology of conventional genetic therapy may be applied to polynucleotide sequences encoding-N-acetylgalactosamine-4-sulfatase. Reviews of conventional genetic therapy techniques can be found in Friedman, *Science* 244:1275–1281 (1989); Ledley, *J. Inherit. Aletab. Dis.* 13:587–616 (1990); and, Tososhev, et al., *Curr. Opinions Biotech.* 1:55–61 (1990).

A particularly preferred method of administering the recombinant enzyme is intravenously. A particularly preferred composition comprises recombinant N-acetylgalactosamine-4-sulfatase, normal saline, phosphate buffer to maintain the pH at about 5–7, and human albumin. The composition may additionally include polyoxyethylenesorbitan, such as polysorbate 20 or 80 (Tween-20 or Tween-80) to improve the stability and prolong shelf life. Alternatively, the composition may include any surfactant or non-ionic detergent known in the art, including but not limited to polyoxyethylene sorbitan 40 or 60; polyoxyethylene fatty acid esters; polyoxyethylene sorbitan monoisostearates; poloxamers, such as poloxamer 188 or poloxamer 407; octoxynol-9 or octoxynol 40.

Preferably the surfactant or non-ionic detergent is present at a concentration of at least 0.0001%, or at least 0.0005%, or at least 0.001%, 0.002%, 0.003%, 0.004% or 0.005% (w/v). Preferably the concentration is the lowest necessary to achieve the desired stability, but may be up to 0.005%, 0.006%, 0.007%, 0.008% 0.009%, 0.01%, or 0.02% (w/v). Most preferably the composition comprises a polysorbate at a concentration of 0.005%±0.003% (e.g. 0.002% to 0.008%). These composition ingredients may preferably be provided in the following amounts:

| | |
|---|---|
| N-acetylgalactosamine-4-sulfatase | 1–5 mg/ml or 50–250 units/ml |
| Sodium chloride solution | 150 mM in an 1V bag, 50–250 cc total volume |
| Sodium phosphate buffer | 10–100 mM, pH 5.8, preferably 10 mM |
| Human albumin, optional | 1 mg/mL |
| Tween −20 or Tween −80 | 0.001%–0.005% (w/v) |

In a preferred embodiment, the ASB is formulated as 1 mg/mL in 150 mM NaCl, 10 mM NaPO$_4$, pH 5.8, 0.005% polysorbate 80.

In a third aspect, the present invention features a method to produce N-acetylgalactosamine-4-sulfatase (ASB) or a biologically active fragment, mutant or analog thereof in amounts which enable using the enzyme therapeutically. In a broad embodiment, the method comprises the step of transfecting a cDNA encoding for all or a part of a N-acetylgalactosamine-4-sulfatase (ASB) or a biologically active mutant or analog thereof into a cell suitable for the expression thereof. In some embodiments, a cDNA encoding for a complete N-acetylgalactosamine-4-sulfatase (ASB) is used, preferably a human N-acetylgalactosamine-4-sulfatase (ASB). However, in other embodiments, a cDNA encoding for a biologically active fragment or mutant thereof may be used. Specifically, one or more amino acid substitutions may be made while preserving or enhancing the biological activity of the enzyme.

In other preferred embodiments, an expression vector is used to transfer the cDNA into a suitable cell or cell line for expression thereof. In one particularly preferred embodiment, the cDNA is transfected into a Chinese hamster ovary cell, such as the CHO-K1 cell line. In yet other preferred embodiments, the production procedure comprises the following steps: (a) growing cells transfected with a DNA encoding all or a biologically active fragment or mutant of a human N-acetylgalactosamine-4-sulfatase a suitable growth medium to an appropriate density, (b) introducing the transfected cells into a bioreactor, (c) supplying a suitable growth medium to the bioreactor, (d) harvesting said medium containing the recombinant enzyme, and (e) substantially removing the transfected cells from the harvest medium.

A suitable medium for growing the transfected cells is a JRH Excell 302 medium supplemented with L-glutamine, glucose and hypoxanthine/thymidine, optionally with or without G418. In a preferred medium, the JRH Excell 302 medium is further supplemented with folic acid, serine, and asparagine, and there is no G418 present in the medium. Using this preferred medium to culture cells provides a higher purity precursor rhASB compared to using the medium supplemented with G418 but not with folic acid, serine, and asparagine (see lane 2 of FIG. 6). It is preferred to grow the cells in such a medium to achieve a cell density of about 1×10$^7$ cells/ml resulting in 10–40 mg/ml of active enzyme. Moreover, it is preferable to grow the transfected cells in a bioreactor for about 5 to 15 days. More preferably, it is about 9 days. Preferably, the transfected cells are grown in a bioreactor using a perfusion-based process with collections continuing up to 35 days. More preferably, the transfected cells are grown in a bioreactor using a perfusion-based process with collections continuing up to 45 days. Even more preferably, the transfected cells are grown in a bioreactor using a perfusion-based process with collections continuing up to 60 days. Even much more preferably, the transfected cells are grown in a bioreactor using a perfusion-based process with collections continuing up to 90 days.

According to preferred embodiments, the transfected cells may be substantially removed from the bioreactor supernatant by filtering them through successive membranes such as a 10 μm membrane followed by a 1 μm membrane followed by a 0.2 μm. Any remaining harvest medium may be discarded prior to filtration.

Recombinant human N-acetylgalactosamine-4-sulfatase may be produced in Chinese. hamster ovary cells (Peters, et al. *J. Biol. Chem.* 265:3374–3381). Its uptake is mediated by a high affinity mannose-6-phosphate receptor expressed on most, if not all, cells (Neufeld et al, "The mucopolysaccharidoses" *The Metabolic Basis of Inherited Disease,* eds. Scriver, et al. New York:McGraw-Hill (1989) p. 1565–1587). Once bound to the mannose-6-phosphate receptor, the enzyme is endocytosed through coated pits and transported to the lysosomes. At the pH of lysosomes, the enzyme is active and begins removing sulfate residues from accumulated dermatan sulfate. In MPS VI fibroblasts, the clearance of storage is rapid and easily demonstrated within 92 hours of enzyme exposure (Anson, et al., *J. Clin. Invest.* 99:651–662 (1997)). The recombinant enzyme may be produced at a 110-L (approximately 90 L working volume) fermentation scale according to a process according to the flow diagram outlined in FIG. 1.

The recombinant enzyme can be produced using the following method as set forth in Table 1A–C.

TABLE 1A

Cell Culture Process by the Fed Batch Process

| Step | Process | In-Process Testing |
|---|---|---|
| 1. Thawing of the Working Cell Bank (WCB) | Inoculate the thawed cells into one T-75 flask with 25 mL of JRH Exell 302 medium supplemented with 4 mM L-glutamine, 4.5 g/L glucose and 10 mg/L hypoxanthine/thymidine; further supplemented with folic acid, serine and asparagine (no G418) Culture for 3 days to achieve 1 × 10$^{10}$ cell density ↓ | Cell count Cell viability |
| 3. 250 mL Spinner Flask | Add cells to 175 mL of supplemented medium (no G418) Culture for 3 days ↓ | Cell count Cell viability |

TABLE 1A-continued

Cell Culture Process by the Fed Batch Process

| Step | Process | In-Process Testing |
|---|---|---|
| 4. 1 L Spinner Flask | Add cells to 800 mL of supplemented medium (no G418) Culture for 1–2 days ↓ | Cell count Cell viability |
| 5. 8 L Spinner Flask | Add cells to 4 L of supplemented medium (no G418) Culture for 1–2 days ↓ | Cell count Cell viability |
| 6. 2x 8 L Spinner Flask | Split working volume into 28 L Spinner Flasks Add cells to 5.5 L of supplemented medium (no G418) to each 8 L Spinner Flask Culture for 1–2 days ↓ | Cell count Cell viability |
| 7. Inoculation of 110 L Bioreactor | Add cells to 7 mL of supplemented medium Culture 9 days ↓ | Cell count Cell viability |
| 8. Production | Approximately 9 days of growth in bioreactor ↓ | Cell Count Cell viability Activity |
| 9. Harvest Supernatant | Harvest is pumped into 100 L bag, refrigerated overnight ↓ | |
| 10. Cell Removal | Cells are removed from the harvest medium by filtration through a 10 μm membrane cartridge followed by 1 μm and 0.2 μm cartridges. Since the cells have been allowed to settle overnight the final 5 to 10% of the harvest medium is discarded prior to filtration. | QC Release Point Activity Bioburden Endotoxin Mycoplasma In vitro advent. Agents |

In one embodiment, the transfected cells are grown in a cell culture process that is a perfusion-based process with collections continuing for up to 35 or more days with a collection rate of approximately 400 L per day from one 110 L bioreactor. Preferably, the collection rate is approximately 800 L per day from one 110 L bioreactor. A process flow diagram comparing the perfusion cell culture process with the batch cell culture process is shown in Table 1B. Comparisons to the fed batch process as well as details of the specific changes implemented for the perfusion-based cell culture process are summarized in Table 1C.

TABLE 1B

Cell Culture Process Comparison Between Fed Batch and Perfusion Processes

| Batch Process | Perfusion Process |
|---|---|
| 1 Working Cell Bank (WCB) Vial | 1 WCB Vial |
| ↓ | ↓ |
| T75 cm² flask | T75 cm² flask |
| ↓ | ↓ |
| 250 mL Spinner Flask | 250 mL Spinner Flask |
| ↓ | ↓ |
| 2 × 250 mL Spinner Flask | 2 × 250 mL Spinner Flask |
| ↓ | ↓ |
| 2 × 3 L Spinner Flask | 2 × 3 L Spinner Flask |
| ↓ | ↓ |
| 2 × 8 L Spinner Flask | 2 × 8 L Spinner Flask |
| ↓ | ↓ |
| 2 × 110 L bioreactors (80–95 L working volume) Batch Mode 11–12 days | 1 × 110 L bioreactors (75–85 L working volume) Batch Mode 1–3 days 1 × 110 L bioreactors (75–85 L working volume) Culture duration up to 35 days |
| ↓ | ↓ |
| Harvest Collection stored in 200 L Polyethylene Bags | Harvest Collection stored in 200 L Polyethylene Bags |

TABLE 1C

Summary Description of the Differences between the Fed Batch and Perfusion Processes

| Production Step | Description (Batch) | Description (Perfusion) |
|---|---|---|
| CELL CULTURE | One batch is the result of one production run with two 110 L bioreactors. | Change: One batch is the result of one production run with one 110 L bioreactor |
| Thawing of WCB vial | One vial for each production batch. Tests: Expected cell viability >95% Expected ≧1 × 10$^6$ cells recovered | Change: Cell Viability: >90% Viability of >90% on thaw has proven to yield successful runs and product that meets. specifications |
| T75 cm$^2$ flasks | Approximately 5 × 10$^6$ cells plated into 1 flask. Length of step: ~3 days Tests: Expected cell viability >90% Expected ≧2 ×10$^7$ cells recovered | No Change |
| 250 mL Spinner Flask | Cells from T75 is split onto a 250 mL spinner flask. Length of step: ~2 days Tests: Expected cell viability >90% Expected ≧2 × 10$^8$ cells recovered | No Change |
| 2 × 250 mL Spinner Flask | Cells from 1 × 250 mL spinner flask are split into two 250 mL spinner flask. Length of step: ~3 days Tests: Expected cell viability >90% Expected ≧4 × 10$^8$ cells recovered | No Change |
| 2 × 3 L Spinner Flask | Cells from 2 × 250 mL spinner flasks are split into two 3 L spinner flask Length of step: ~4 days Tests: Expected cell viability >90% Expected ≧4.8 × 10$^9$ cells recovered | No Change |
| 2 × 8 L Spinner Flask | Cells from 2 × 3 L spinner flasks are split into two 8 L spinner flask. Length of step: ~2 days Expected cell Viability >90% Expected ≧1.6 × 10$^{10}$ cells recovered | No Change |
| Inoculation of culture flask | Inoculum of ≧0.8 × 10$^{10}$ cells are added to each of two bioreactors containing 32 L culture medium each. Culture monitored with PC-interfaced control system. | Change: Inoculum of ≧1.6 × 10$^{10}$ cells added to one bioreactor containing 64 L culture medium. (Reflects the use of one bioreactor versus two.) |
| Production | Growth: 3 days of growth until culture reaches density of >3.2 × 10$^{10}$ cells. Vertical Split: Culture media added to final volume of 95 L. Harvesting: Supernatant was harvested at day 11 or when cell viability fell below 70% Supernatant is filtered and stored. | Changes: Growth/Transition/Harvesting: When cell density reaches >8 × 10$^{10}$ cells/mL, perfusion is started. The perfusion rate is gradually increased to 5 vessel volumes per day based on glucose levels. When the cell density is >1.28 × 10$^{12}$ the pH set point is adjusted to 7.35. Once increases in perfusion rates cease, glucose level is maintained by reducing cell density with a cell bleed. Harvested supernatant is collected and filtered. |
| Termination | Run is terminated at harvest. | Change: Run is terminated after 35 or more days is reached, or activity falls below 2 mg/L for three consecutive days or after adequate harvested supernatant is collected. |

The inoculum preparation for scale-up process is the same for the fed batch and perfusion processes. In one embodiment, the rhASB cell culture is initiated by thawing a single vial from the Working Cell Bank and transferring its contents (approximately 1 mL) to approximately 25 mL of EX-CELL 302 Medium (Modified w/L-Glutamine, No Phenol Red) in a T75 cm$^2$ cell culture flask. In each expansion step, the cell culture is incubated until a viable cell count of approximately 0.8×10$^6$ cells/mL is achieved. Each cell expansion step is monitored for cell growth (cell density) and viability (via trypan blue exclusion). All additions of EX-CELL 302 Medium (Modified w/L-Glutamine, No Phenol Red) medium and cell transfers are preformed aseptically in a laminar flow hood. The cell culture is expanded sequentially from the T75 cm$^2$ flask to a 250 mL spinner flask, to two 250 mL spinner flasks, to two 3 L spinner flasks, and finally to two 8 L spinner flasks. The entire scale-up process lasts approximately 14 days. When the two 8 L spinner flasks are at a density of at least 1.0×10$^6$ cells/mL, the flasks are used to seed one 110 L bioreactor.

It is preferred that bioreactor operations for rhASB expression or production or manufacture utilize a perfusion-based cell culture process. Preferably, the bioreactor, using the perfusion process, can control cell densities up to as high as 37 million cells per mL; compared to 4–5 million cells per mL using the fed batch process.

The perfusion-based process runs longer (35 days) than the fed batch process (11–12 days) and produces a greater volume of harvested cell culture fluid (approximately 400 L/day at a perfusion rate of 5 vessel volumes per day) compared to the fed batch process (190 L/run). Preferably, harvesting is performed up to 35 days for a total collection of approximately 8400 L of supernatant.

End of Production Cells (EPC) are evaluated for genetic stability, identity, sterility and adventitious agent contamination per ICH guideline. Preferably, EPC results, obtained from a 35-day long bioreactor run, AC60108, produced under cGMP conditions, show no growth or negative results or no detection of the presence of bacteria and fungi, mycoplasma, adventitious viral contaminants, murine viruses, or like contaminants or particles.

In a fourth aspect, the present invention provides a transgenic cell line which features the ability to produce N-acetylgalactosamine-4-sulfatase (ASB) or a biologically active fragment, mutant or analog thereof in amounts which enable using the enzyme therapeutically. In preferred embodiments, the present invention features a recombinant Chinese hamster ovary cell line such as the CHO K1 cell line that stably and reliably produces amounts of N-acetylgalactosamine-4-sulfatase (ASB) which enable using the enzyme therapeutically. Especially preferred is the CHO-K1 cell line designated CSL4S-342. In some preferred embodiments, the cell line contains one or more of an expression construct. More preferably, the cell line contains contains about 10 or more copies of the expression construct. In even more preferred embodiments, the cell line expresses recombinant N-acetylgalactosamine-4-sulfatase (ASB) in amounts of at least about 20–80 or 40–80 micrograms per 10$^7$ cells per day.

Recombinant human N-acetylgalactosamine-4-sulfatase (rhASB) may be produced from a stable transfected CHO-K1 (Chinese hamster ovary) cell line designated CSL4S-342 The cell line is described in the literature (Crawley, *J.Clin. Invest.* 99:651–662 (1997)). Master Cell Bank (MCB) and Working Cell Bank (WBC) were prepared at Tektagen Inc. (Malvern, Pa.). The cell banks have been characterized per ICH recommended guidelines for a recombinant mammalian cell line.

In a fifth aspect, the present invention provides novel vectors suitable to produce N-acetylgalactosamine-4-sulfatase (ASB) or a biologically active fragment, mutant or analog thereof in amounts which enable using the enzyme therapeutically.

In a sixth aspect, the present invention provides novel N-acetylgalactosamine-4-sulfatase (ASB) or a biologically active fragment, mutant or analog thereof produced in accordance with the methods of the present invention and thereby present in amounts which enable using the enzyme therapeutically. The preferred specific activity of the N-acetylgalactosamine-4-sulfatase (ASB) according to the present invention is about 20–90 Unit, and more preferably greater than 50 units per milligram protein: Preferably, the enzyme has a deglycosylated weight of about 55 to 56 kDa, most preferably about 55.7 kDa. Preferably, the enzyme has a glycosylated weight of about 63 to 68 kDa, most preferably about 64 to 66 kDa. The present invention also includes biologically active fragments including truncated molecules, analogs and mutants of the naturally-occurring human N-acetylgalactosamine-4-sulfatase.

The human cDNA for N-acetylgalactosamine-4-sulfatase predicts a protein of 533 amino acids with a signal peptide of 41 amino acids (Peters, et al. *J. Biol. Chem.* 265:3374–3381). The predicted molecular weight is about 55.9 kDa after signal peptide cleavage. The recombinant enzyme has an apparent molecular weight of 64 kDa on SDS-PAGE due to carbohydrate modifications. The predicted protein sequence contains six potential N-linked oligosaccharide modification sites of which four may be used based on a 2,000 kDa average 1.0 mass and 8,000 kDa difference between predicted and apparent mass. A mature form of the intracellular protein has three peptides attached by cystine bonds. The largest peptide has a molecular weight of 47 kDa; the other two has a molecular weight of 6 and 7 kDa respectively.

A description of a drug product produced and purified according to the methods of the present invention is provided in Table 2.

TABLE 2

Drug Product Preliminary Specifications

| Test | Procedure | Specification |
| --- | --- | --- |
| Activity | Fluorescence assay | 20,000–120,000 mUnits |
| Adventitious Viruses* | In Vitro Assay | Pass |
| Appearance | Visual | Clear, colorless to pale yellow solution |
| Bacterial Endotoxin | LAL | ≦2 EU/mL |
| Chloride | Atomic Absorption | Report Value |
| ASB fibroblast Uptake Assay | TBD | ≦40 nmol |
| Mycoplasma* | Points to Consider 1993 | Pass |
| Particulates | USP | ≦600/vial at 25 μm & ≦6000/vial at 10 μm |
| PH | USP | 5.5–6.8 |
| Phosphate | Atomic Absorption | Report Value |
| Protein Concentration | UV 280 | 0.8–1.2 mg/ml |
| Purity | SDS PAGE | 1 major band between 65–70 kDa |
|  | RP-HPLC | >95% |
| Residual Blue Dye | TBD | Report Value |
| Residual Copper | TBD | Report Value |
| Sodium | Atomic Absorption | Report Value |
| Specific Activity | Calculation | 40,000–80,000 mUnits/mg |
| Sterility | 21 CFR 610 | Pass |

*Tested on harvested supernatant from bioreactor (after cell removal by filtration).

In a seventh aspect, the present invention features a novel method to purify N-acetylgalactosamine-4-sulfatase (ASB) or a biologically active fragment, mutant or analog thereof.

Figure 2:
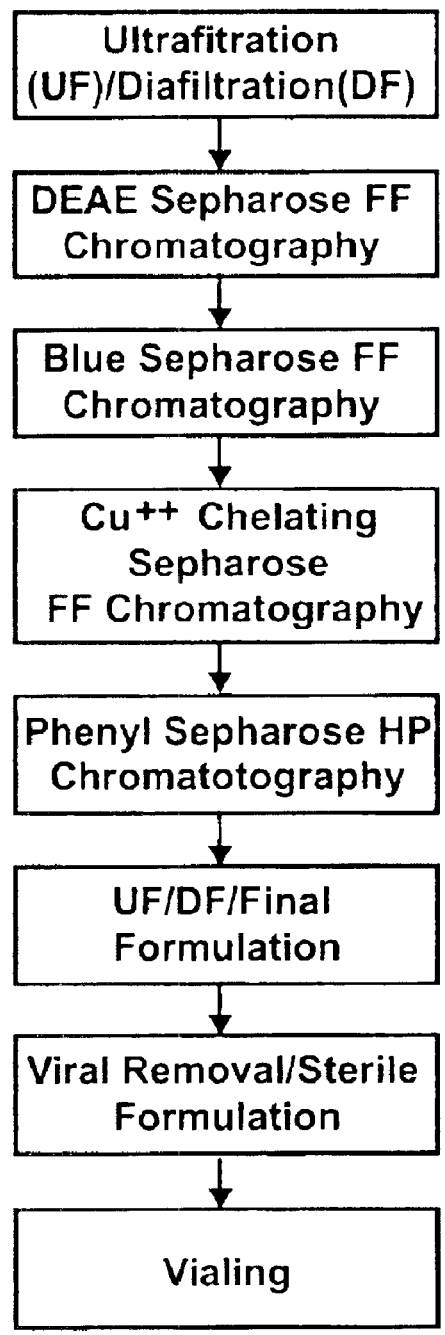
FIG. 2 provides a flow diagram of the method for purifying a human N-acetylgalactosamine-4-sulfatase (ASB) according to the batch process method (Table 14).

According to a first embodiment, a transfected cell mass is grown and removed leaving recombinant enzyme. Exogenous materials should normally be separated from the crude bulk to prevent fouling of the columns. Preferably, the growth medium containing the recombinant enzyme is passed through an ultrafiltration and diafiltration step. In one method, the filtered solution is passed through a DEAE Sepharose chromatography column, then a Blue Sepharose chromatography column, then a Cu++ Chelating Sepharose chromatography column, and then a Phenyl Sepharose chromatography column. Such a four step column chromatography including using a DEAE Sepharose, a Blue Sepharose, a Cu++ Chelating Sepharose and a Phenyl Sepharose chromatography column sequentially results in especially highly purified recombinant enzyme. Those of skill in the art appreciate that one or more chromatography steps may be omitted or substituted or the order of the steps altered within the scope of the present invention. In other preferred embodiments, the eluent from the final chromatography column is ultrafiltered/diafiltered, and an appropriate step is performed to remove any remaining viruses. Finally, appropriate sterilizing steps may be performed as desired. The recombinant enzyme may be purified according to a process outlined in FIG. 2. The quality of the recombinant enzyme is key to patients. The rhASB produced by this method is substantially pure (>95%).

In a preferred embodiment, the ultrafiltration/diafiltration step is performed with a sodium phosphate solution of about 10 mM and with a sodium chloride solution of about 100 mM at a pH of about 7.3. In another embodiment, the DEAE Sepharose chromatography step is performed at a pH of about 7.3 wherein the elute solution is adjusted with an appropriate buffer, preferably a sodium chloride and sodium phosphate buffer. In additional preferred embodiments, the Blue Sepharose chromatography step is performed at a pH of about 5.5 wherein the elute solution is adjusted with an appropriate buffer, preferably a sodium chloride and sodium acetate buffer. Also, in preferred embodiments, the Cu++ Chelating Sepharose chromatography step is performed with an elution buffer including sodium chloride and sodium acetate. In especially preferred embodiments, a second ultrafiltration/diafiltration step is performed on the eluate from the chromatography runs wherein the recombinant enzyme is concentrated to a concentration of about 1 mg/ml in a formulation buffer such as a sodium chloride and sodium phosphate buffer to a pH of about 5.5 to 6.0, most preferably to a pH of 5.8. Phosphate buffer is a preferred buffer used in the process because phosphate buffer prevents critical degradation and improves the stability of the enzyme.

A more detailed description of particularly preferred purification methods within the scope of the present invention is set forth in Table 3.

TABLE 3

Purification Process Overview

| Step | | Process |
|---|---|---|
| 1. UF/DF | | Filtered harvest fluid (HF) is concentrated ten fold and then diafiltered with 5 volumes of 10 mM Sodium Phosphate, 100 mM NaCl, pH 7.3 using a tangential flow filtration (TFF) system. ↓ |
| 2. DEAE Sepharose FF (flow through) | Pre-wash 1 buffer: | 0.1 N NaOH |
| | Pre-wash 2 buffer: | 100 mM NaPO4 pH 7.3 |
| | Equilibration buffer: | 100 mM NaCl, 10 mM NaPO4, pH 7.3 |
| | Load: | Product from Step 1 |
| | Wash buffer: | 100 mM NaCl, 10 mM NaPO4, pH 7.3 |
| | Strip buffer: | 1 M NaCl, 10 mM NaPO4, pH 7.3 |
| | Sanitization buffer: | 0.5 N NaOH |
| | Storage buffer: | 0.1 N NaOH ↓ |
| 3. Blue Sepharose FF | Pre-wash 1: | 0.1. N NaOH |
| | Pre-wash 2: | H$_2$O |
| | Pre-wash 3: | 1 M NaAc, pH 5.5 |
| | Equilibration buffer: | 150 mM NaCl, 20 mM NaAc, pH 5.5 |
| | Load: | DEAE flow through |
| | Wash buffer: | 150 mM NaCl, 20 mM NaAc, pH 5.5 |
| | Elution buffer: | 500 mM NaCl, 20 mM NaAc, pH 5.5 |
| | Regeneration buffer: | 1 M NaCl, 20 mM NaAc, pH 5.5 |
| | Sanitization buffer: | 0.1 N NaOH, 0.5–2 hours |
| | Storage buffer: | 500 mM NaCl, 20 mM NaAc, pH 5.5, 20% ETOH ↓ |
| 4. Cu++ Chelating Sepharose FF | Sanitization buffer: | 0.1 N NaOH |
| | Wash buffer: | H$_2$O |
| | Charge Buffer: | 0.1 M Copper Sulfate |
| | Equilibration buffer: | 20 mM NaAc, 0.5 M NaCl, 10% Glycerol, pH 6.0 |
| | Load: | Blue Sepharose Eluate |
| | Wash Buffer 1: | 20 mM NaAc, 0.5 M NaCl, 10% Glycerol, pH 6.0 |
| | Wash Buffer 2: | 20 mM NaAc, 1 M NaCl, 10% Glycerol, pH 4.0 |
| | Wash Buffer 3: | 20 mM NaAc, 1 M NaCl, 10% Glycerol, pH 3.8 |
| | Elution Buffer: | 20 mM NaAc, 1 M NaCl, 10% Glycerol, pH 3.6 |
| | Strip Buffer: | 50 mM EDTA, 1 M NaCl |
| | Sanitization Buffer: | 0.5 N NaOH, 0.5–2 hours |
| | Storage Buffer: | 0.1 N NaOH ↓ |

TABLE 3-continued

Purification Process Overview

| Step | Process | |
|---|---|---|
| 5. Phenyl Sepharose HP | Pre-wash 1 Buffer: | 0.1 N NaOH |
| | Pre-wash 2 Buffer: | H$_2$O |
| | Equilibration buffer: | 3 M NaCl, 20 mM NaAc, pH 4.5 |
| | Load: | Cu$^{++}$Chelating Sepharose Eluate |
| | Wash Buffer 1: | 3.0 M NaCl, 20 mM NaAc, pH 4.5 |
| | Wash Buffer 2: | 1.5 M NaCl, 20 mM NaAc, pH 4.5 |
| | Elution buffer 1: | 1.0 M NaCl, 20 mM, NaAc, pH 4.5 |
| | Strip Buffer: | 0 M NaCl, 20 mM NaAc, pH 4.5 |
| | Sanitization Buffer: | 0.5 N NaOH |
| | Storage Buffer: | 0.1 N NaOH |
| 6. UF/DF | The purified rhASB is concentrated and diafiltered to a final concentration of 1.5 mg/ml in formulation buffer (150 mM NaCl, 10 mM NaPO4, pH 5.8) using a TFF system. | |
| 7. Formulation (if necessary) | Dilute with additional formulation buffer to 1.0 mg/ml | |
| 8. Viral Reduction/ Sterile filtration | 0.02 μm filtration into sterile container | |
| 9. Vialing | Product filled into 5 cc Type 1 glass vials, manually stoppered, crimped and labeled. | |

The formulated bulk drug substance can be sterilized through a 0.04 micron or preferably a 2 micron filter in a class 100 laminar flow hood into Type 1 glass vials. The vials may be filled to a final volume of about 5 mL using a semi-automatic liquid filling machine. The vials may then be manually stoppered, sealed and labeled.

A more preferred method to purify a precursor N-acetylgalactosamine-4-sulfatase comprises: (a) obtaining a fluid containing precursor N-acetylgalactosamine-4-sulfatase; (b) reducing the proteolytic activity of a protease in said fluid able to cleave the precursor N-acetylgalactosamine-4-sulfatase, wherein said reducing does not harm said precursor N-acetylgalactosamine-4-sulfatase; (c) contacting the fluid with a Cibracon blue dye interaction chromatography resin; (d) contacting the fluid with a copper chelation chromatography resin (e) contacting the fluid with a phenyl hydrophobic interaction chromatography resin; and (f) recovering said precursor N-acetylgalactosamine-4-sulfatase. Preferable, steps (c), (d) and (e) are performed sequentially. This method requires no more than three chromatography steps or columns. In order to obtain highly purified precursor N-acetylgalactosamine-4-sulfatase, no further chromatography steps or columns are required. This method does not comprise the fluid contacting a DEAE Sepharose resin. The recovered precursor N-acetylgalactosamine-4-sulfatase has a purity of at least equal to or greater than 99%. The overall recovery yield can be at least about 40–60%.

Preferably, obtaining the fluid containing the precursor N-acetylgalactosamine-4-sulfatase comprises growing a culture of cells transformed with a gene encoding N-acetylgalactosamine-4-sulfatase; preferably, the gene encodes human N-acetylgalactosamine-4-sulfatase. Preferably, the cells are mammalian cells. More preferably, the mammalian cells are Chinese Hamster Ovary cells. The obtaining step can further comprise harvesting the fluid from said culture of cells. The obtaining step can further comprise concentrating said fluid to about 20×.

A feature of this method is an early separation of protease activity and the precursor N-acetylgalactosamine-4-sulfatase. This separation can comprise either (1) the reduction, inhibition, or inactivation of the protease activity, or (2) the physical separation of the protease(s) from the precursor N-acetylgalactosamine-4-sulfatase. Preferably, this separation occurs as early as possible during the purification process. The purpose is to keep to a minimum the number of molecules of precursor N-acetylgalactosamine-4-sulfatase being cleaved into the mature or processed form and/or other degraded form(s). The precursor form of N-acetylgalactosamine-4-sulfatase is the preferred form, as opposed to the mature or processed form, because it is more readily taken up into the target tissue and for subsequent targeting to the lysosome. The earlier or sooner the protease activity is separated from the precursor N-acetylgalactosamine-4-sulfatase: the fewer the number of molecules of the precursor form would be cleaved into the mature or processed form.

The activity of the protease is reduced or inhibited by adjusting the fluid to a pH value between about 4.8 to 8.0. Preferably, the pH value is between about 4.8 to 5.5. More preferably, the pH value is between about 4.8 and 5.2. The specific protease activity that is desired to be reduced is protease activity that specifically cleaves precursor form of N-acetylgalactosamine-4-sulfatase into the mature or processed forms. The protease activity is found in one or more cysteine protease. A cysteine protease that specifically cleaves precursor N-acetylgalactosamine-4-sulfatase is cathepsin L. This cathepsin L has a molecular weight, of about 36 kDa in its inactive form that is converted to its active forms of 21–29 kDa in size upon exposure to pH of less than 5.0 (see FIG. 9C). The pH can be adjusted into any value whereby the protease(s) is not converted from its inactive form to its active form and the desired precursor N-acetylgalactosamine-4-sulfatase, or biological activity thereof, is not harmed or not irreversibly harmed.

Preferably, step (c) comprises passing the fluid through a Cibracon blue dye interaction chromatography column. More preferably, the Cibracon blue dye interaction chromatography column is a Blue Sepharose 6 Fast Flow column. Preferably, step (d) comprises passing the fluid through a copper chelation chromatography column. More preferably, the copper chelation chromatography column is a Chelating Sepharose Fast Flow column. Preferably, step (e) comprises passing the fluid through a phenyl hydrophobic interaction chromatography column. More preferably, the phenyl hydrophobic interaction chromatography column is a Phenyl Sepharose 6 Fast Flow High Sub column. Preferably, the temporal sequence of steps (c), (d) and (e) is step (c), step (d) and step (e).

The recovering step can comprise ultrafiltration and/or diafiltration of the fluid. The recovering can comprise filtering the fluid to remove DNA and/or filtering the fluid to remove virus. The filtering, for removing virus, can comprise passing said fluid through a 0.02 μm filter.

This method can also be used to purify a N-acetylgalactosamine-4-sulfatase or biologically active fragment, analog or mutant thereof.

The purity of rhASB is measured or determined using reverse-phase high performance liquid chromatography ("RP-HPLC"), which separates proteins based on differences in hydrophobicity. This assay uses a C4 column (Phenomenex Jupiter) as the stationary phase and a gradient of water:acetonitrile as the mobile phase. The protein samples are initially injected onto the column in water; under these conditions, all proteins will bind to the column. A gradually increasing concentration of acetonitrile is then infused through the column. This acetonitrile gradient increases the hydrophobicity of the mobile phase, to the point where individual proteins become soluble in the mobile phase and elute from the column. These elution times are accurately reproducible for each individual protein in a mixture. Proteins are detected as peaks on a chromatogram by ultraviolet absorbance at 210 nm. The areas of each peak are calculated, and the sample purity can be calculated as the ratio of the rhASB peak are to the total area of all peaks in the chromatogram. RP-HPLC is a proven high-resolution, reproducible method of determining the purity of rhASB.

Studies prior to this application indicate that the purity of ASB was determined by performing an impurity protein ELISA. This method of using impurity protein ELISA (the details of which are not disclosed) probably used antibodies raised against a mixture of potential host-cell impurity proteins. The ELISA would likely be performed using a standard curve of the same mixture of potential impurity proteins used to generate the antibodies. Test samples would likely be quantitated for impurity levels, relative to this standard mixture. These assays are valuable tools in protein purification, but are less accurate than RP-HPLC for determining the product purity for the following reasons:

(1) In the RP-HPLC assay, the proportions of rhASB and impurities are both determined by the same measurement (UV absorbance). In the ELISA, the impurity concentration is determined by antibody binding whereas the target protein content is determined by another assay method (usually UV absorbance or Bradford). The "percent purity" value should be calculated as the ratio of two quantities with the same units, experimentally determined by the same method.

(2) For the ELISA to work well, the sample detected by the antibody should have the same protein composition as the standard. This is very unlikely to be the case in an impurity protein ELISA. The assay standard for this type of assay would be a mixture of many individual proteins, against which the antibodies were generated. However, only a small subset of impurity proteins should be present in purified rhASB product. Therefore, the antibody reagent will now be detecting a different mixture of proteins, and the response versus the standard will probably be quite nonlinear. When this occurs, the assay yields a different net value for each sample dilution, so one does not know which dilution (if any) is giving the correct value.

(3) In addition, not all potential impurity proteins are immunogenic or immunogenic to the same degree in animals such as rabbits, used to generate the antibodies. Therefore, the impurity level determined by ELISA may only reflect a subset of the impurities present in the purified products. It is entirely possible to have one or more major impurities in the product that are totally undetectable. In contrast, RP-HPLC detects all proteins because UV absorbance is a universal property of protein molecules.

(4) Finally, there are two types of impurities in a purified drug product: product-unrelated impurities (host cell proteins as discussed above) and product-related impurities (degradation products including processed forms and aggregates). The latter cannot be detected by the impurity ELISA but can be readily detected by RP-HPLC.

Therefore, actual numbers obtained from the impurity protein ELISA are open to question, and RP-HPLC numbers are based on a firmer foundation.

In addition, SDS-PAGE analysis permits detection of both host cell impurities and processed or degraded forms of the desired drug protein product. When used in conjunction with Western blot, product-unrelated impurities from host cell-contaminants can be differentiated from product-related impurities. Finally, SEC-HPLC permits a level of quantification of product-related impurities because it can detect impurities of different molecular weights, including lower molecular weight processed or degraded forms of the protein as well as monomers, dimers and other multimers.

An embodiment of this method of purification is depicted in Table 4.

TABLE 4

| Method of Purification | |
|---|---|
| Step | Process |
| Harvest Filtration | Filtration through Clarification filters, 0.45 μm filters and finally 0.2 μm filter. Filtered polled harvests are stored in polypropylene bags |
| UF Concentration | Equilibration and flush: 100 mM sodium phosphate, pH 7.3 Load: filtered harvest fluid Concentration: Concentration to 20X Filtration: Filter the diluted product through a 0.2 μm filter into storage container |

TABLE 4-continued

Method of Purification

| Step | Process |
| --- | --- |
| pH adjustment and filtration | pH adjustment: Add 10% glacial acetic acid to pooled 20X concentrates to a final pH of equal to or less than about 7.3; preferably, the pH is about 4.0 to 7.3; more preferably, the pH is about 4.5 to 5.5; even more preferably, the pH is about 5.0<br>Load: pooled 20X concentrates<br>Rinse: Water-for Injection (WFI)<br>Filtration through Clarification filters and 0.2 μm filter.<br>Flush: 20 mM sodium acetate, 120 mM sodium chloride, pH 5.0<br>The recovery yield can be at least about 83% |
| Cibracon blue dye interaction chromatography column (Blue Sepharose 6 FF) (Blue, Blue Sepharose) | Pre-Wash: 0.1 N sodium hydroxide<br>Wash: Water-for-Injection (WFI)<br>Equilibration: 10 mM sodium phosphate, pH is less than about 6.5; preferably, pH is about 5.0 to 6.5; more preferably, pH is about 6.45<br>Load: pH adjusted and filtered pooled 20X concentrates<br>Wash: 10 mM sodium phosphate, pH 6.45<br>Elution: 10 mM sodium phosphate, 125 mM sodium chloride, pH 6.45<br>Regeneration: 10 mM sodium phosphate, 1.0 M sodium chloride, pH 6.45<br>Sanitization: 0.1 N sodium hydroxide<br>Wash 1: Water-for-Injection (WFI)<br>Wash 2: 10 mM sodium phosphate, 1.0 M sodium chloride, pH 6.45<br>Storage: 20% Ethanol<br>The recovery yield can be at least about 84% |
| Copper chelation chromatography column (Chelating Sepharose FF) (Copper, CC, Copper-Chelating) | Pre-Wash: 0.1 N sodium hydroxide<br>Wash: Water-for-Injection (WFI)<br>Charge Buffer: 0.1 M cupric sulfate<br>Equilibration: 20 mM sodium acetate, 0.5 M sodium chloride, 10% glycerol, pH is less than about 6.0; preferably, pH is about 3.6 to 5.5; more preferably, pH is about 5.5<br>Load: Adjust glycerol content of pooled Blue Eluates to 10%, by adding 100 mM sodium acetate, 2.0 M sodium chloride, 50% glycerol, pH 5.2<br>Wash 1: 20 mM sodium acetate, 0.5 M sodium chloride, 10% glycerol, pH 5.5<br>Wash 2: 20 mM sodium acetate, 0.5 M sodium chloride, 10% glycerol, pH 3.9<br>Elution: 20 mM sodium acetate, 0.5 M sodium chloride, 10% glycerol, pH 3.6<br>Eluate hold for 30–120 minutes prior to adjustment to pH 4.5 with 0.5 M NaOH<br>Regeneration: 50 mM EDTA, 1.0 M sodium chloride, pH 8.0<br>Sanitization: 0.5 M sodium hydroxide<br>Storage: 0.1 M sodium hydroxide<br>The recovery yield can be at least about 86% |
| Phenyl hydrophobic interaction chromatography column (Phenyl Sepharose 6 FF High Sub) (Phenyl, Phenyl High Sub) | Pre-Wash: 0.1 N sodium hydroxide<br>Wash: Water-for-Injection (WFI)<br>Equilibration: 20 mM sodium acetate, 2.0 M sodium chloride, pH is about 4.5 to 7.1; preferably, pH is about 4.5<br>Load: Adjust sodium chloride content of Copper Eluate to 2 M, by adding 20 mM sodium acetate, 5 M sodium chloride, pH 4.5<br>Wash 1: 10 mM sodium phosphate, 2.0 M sodium chloride, pH 7.1<br>Wash 2: 20 mM sodium acetate, 2.0 M sodium chloride, pH 4.5<br>Elution: 20 mM sodium acetate, 250 mM sodium chloride, pH 4.5<br>Regeneration: 20 mM sodium acetate, pH 4.5<br>Sanitization: 0.5 N sodium hydroxide<br>Storage: 0.1 N sodium hydroxide<br>The recovery yield can be at least about 88% |
| UF/DF, DNA Filtration, Viral Filtration, Formulation | Equilibration: 10 mM sodium phosphate, 150 mM sodium chloride, pH 5.8<br>Concentration: Concentration to NMT 1.5 mg/mL<br>Diafiltration: 10 mM sodium phosphate, 150 mM sodium chloride, pH 5.8<br>DNA Filtration: Product filtered through a DNA filter<br>Viral Filtration/Dilution: Product filtered through a 0.02 μm filter and diluted to 1.0 mg/ml<br>Formulation: Polysorbate 80 at a concentration of 50 μg/mL is added<br>Filtration: Filter the diluted product through a 0.2 μm filter into storage container |

The components of the drug product thus obtained are set forth in Table 5. The components of the drug product composition within the scope of the present invention are set forth in Table 6.

TABLE 5

Drug Product Component

| Component | Description |
| --- | --- |
| Active Ingredient | Recombinant human N-acetylgalactosamine-4-sulfatase |
| Excipients | Sodium Phosphate, Monobasic, 1 H$_2$0<br>Sodium Phosphate, Dibasic, 7 H$_2$0<br>Sodium Chloride |
| Container | Kimble Glass, Type I 5 ml clear glass vial, Borosilitcate<br>West pharmaceuticals, S-127 4432150 Grey stopper |

TABLE 6

Drug Product Composition

| Component | Amount |
| --- | --- |
| RhASB | 1 mg/mL |
| Sodium Phosphate, Monobasic, 1 H$_2$0 | 9 mM |
| Sodium Phosphate, Dibasic, 7 H$_2$0 | 1 mM |
| Sodium Chloride | 150 mM |

The invention having been described, the following examples are offered to illustrate the subject invention by way of illustration, not by way of limitation.

EXAMPLE 1

Clinical Evaluation with Recombinant Human N-acetylgalactosamine-4-sulfatase Summary The indication for recombinant human N-acetylgalactosamine-4-sulfatase (rhASB) is the treatment of MPS VI, also known as Maroteaux-Lamy Syndrome. We propose a clinical development program for rhASB consisting of an initial open-label clinical trial that will provide an assessment of weekly infusions of the enzyme for safety, pharmacokinetics, and initial response of both surrogate and defined clinical endpoints. The trial will be conducted for a minimum of three months to collect sufficient safety information for 5 evaluable patients. At this time, should the initial dose of 1 mg/kg not produce a reasonable reduction in excess urinary glycosaminoglycans or produce a significant direct clinical benefit, the dose will be doubled and maintained for an additional three months to establish safety and to evaluate further efficacy.

Objectives

Our primary objective is to demonstrate safety of a weekly infusion of rhASB in patients with MPS VI for a minimum of a three-month period. Measurements of safety will include adverse events, immune response and allergic reactions (complement activation, antibody formation to recombinant enzyme), complete clinical chemistry panel (kidney and liver function), urinalysis, and CBC with differential.

One secondary objective is to evaluate efficacy by monitoring changes in several parameters known to be affected in MPS VI. These include a six-minute walk test (as a measure of exercise tolerance), full pulmonary function (PFT) evaluation, reduction in levels of urinary glycosaminoglycans and hepatomegaly (as measures of kidney and liver GAG storage), growth velocity, joint range of motion, Children's Health Assessment Questionnaire (CHAQ), visual acuity, cardiac function, sleeping studies, and two different global assessments; one performed by the investigator, one performed by the patient/caregiver. A second secondary objective is to determine pharmacokinetic parameters of infused drug in the circulation, and general distribution and half-life of intracellular enzyme using leukocytes and buccal tissue as sources of tissue. It is anticipated that these measures will help relate dose to clinical response based on the levels of enzyme delivered to the lysosomes of cells.

Methods

We will conduct a single center, open-labeled study to demonstrate safety and to evaluate clinical parameters of treatment with rhASB in patients with MPS VI. Patients will be admitted for a two week baseline evaluation that will include a medical history and physical exam, psychological testing, endurance testing (treadmill), a standard set of clinical laboratory tests (CBC, Panel 20, CH50, UA), a MRI or CAT scan of the body (liver and spleen volumetric, determination, bone and bone marrow evaluation, and lymph node and tonsillar size), a cardiology evaluation (echocardiogram, EKG, CXR), an airway evaluation (pulmonary function tests), a sleep study to evaluate for obstructive events during sleep, a joint restriction analysis (range of motion will be measured at the elbows and interphalangeal joints), a LP with CNS pressure, and biochemical studies (buccal N-acetylgalactosamine-4-sulfatase activity on two occasions, leukocyte N-acetylgalactosamine-4-sulfatase activity on two occasions, urinary GAG on three occasions, serum generation for ELISA of anti-rhASB antibodies and 24 hour urine for creatinine clearance). In addition to the above evaluations, each patient will be photographed and videotaped performing some physical movements such as attempting to raise their hands over their heads and walking. Patients will be titrated with antihistamines such that pretreatment with these agents could be effectively employed prior to infusion of enzyme. The proposed human dose of 1 mg/kg (50 U/kg) will be administered weekly by i.v. infusion over 4 hours. The patient will remain in the hospital for the first two weeks, followed by short stays for the next four weeks. Treatment for the final six weeks will be conducted at a facility close to the patient's home. Patients will return to the hospital for a complete evaluation at three months. Should dose escalation to 2 mg/kg be required, the patients will follow the same schedule outlined above for the first twelve weeks. Under either scenario, a complete evaluation will also occur at 6 months from the time of entering the trial. Safety will be monitored throughout the trial. Patients completing the trial will be continued on therapy following an extended protocol for as long as safety and efficacy conditions warrant it until BLA approval.

Patient Number and Enrollment Rate

A single patient will be enrolled at the onset of the trial, with two additional patients one month later, and two more patients two weeks later barring any unforeseen complications related to treatment. Additional patients will be admitted should any of the enrolled patients become critically ill, or if a child is in need of an acute clinical procedure for life threatening or harmful conditions.

Diagnosis and Inclusion/Exclusion Criteria

The patient may be male or female, aged five years or older with a documented diagnosis of MPS VI confirmed by measurable clinical signs and symptoms of MPS VI, and supported by a diminished fibroblast or leukocyte ASB enzyme activity level. Female patients of childbearing potential must have a negative pregnancy test (urine β-hCG) just prior to each dosing and must be advised to use a medically accepted method of contraception throughout the study. A patient will be excluded from this study if the patient has previously undergone bone marrow transplantation; is pregnant or lactating; has received an investigational drug within 30 days prior to study enrollment; or has a medical condition, serious intercurrent illness, or other extenuating circumstance that may significantly decrease study compliance.

Dose, Route, and Regimen

Patients will receive rhASB at a dose of 1 mg/kg (~50 U/kg) for the first 3 months of the study. In the event that excess urine GAGs are not decreased by a reasonable amount and no clinical benefit is observed, the dose will be doubled. Dose escalation will occur only after all 5 patients have undergone 3 months of therapy. This rhASB dosage form will be administered intravenously over approximately a four-hour period once weekly for a minimum of 12 consecutive weeks. A peripheral intravenous catheter will be placed in the cephalic or other appropriate vein and an infusion of saline begun at 30 cc/hr. The patient will be premedicated with up to 1.25 mg/kg of diphenylhydramine i.v. based on titration experiments completed prior to the trial. rhASB will be diluted into 100 cc of normal saline supplemented with 1 mg/ml human albumin. The diluted enzyme will be infused at 1 mg/kg (about 50 units per kg) over a 4 hour period with cardiorespiratory and pulse oximeter monitoring. The patients will be monitored clinically as well as for any adverse reaction to the infusion. If any unusual symptoms are observed, including but not limited to malaise, shortness of breath, hypoxemia, hypotension, tachycardia, nausea, chills, fever, and abdominal pain, the infusion will be stopped immediately. Based on clinical symptoms and signs, an additional dose of diphenylhydramine, oxygen by mask, a bolus of i.v. fluids or other appropriate clinical interventions such as steroid treatment may be administered. If an acute reaction does occur, an assessment for the consumption of complement in the serum will be tested. A second i.v. site will be used for the sampling required for pharmacokinetic analysis.

Evaluable Patients

The data from any given patient will be considered evaluable as long as no more than two non-sequential infusions are missed during the 12 weeks of therapy. The initial, midpoint and final evaluations must be completed.

Safety

The enzyme therapy will be determined to be safe if no significant acute reactions occur that cannot be prevented by altering the rate of administration of the enzyme, or acute antihistamine or steroid use. The longer-term administration of the enzyme will be determined to be safe if no significant abnormalities are observed in the clinical examinations, clinical labs, or other appropriate studies. The presence of antibodies or complement activation will not by themselves be considered unsafe, but such antibodies will require monitoring by ELISA, and by clinical assessments of possible immune complex disease.

Efficacy

One purpose of this study is to evaluate potential endpoints for the design of a pivotal trial. Improvements in the surrogate and clinical endpoints are expected as a result of delivery of enzyme and removal of glycosaminoglycan storage from the body. Dose escalation will be performed if mean excess urinary glycosaminoglycan levels are not reduced by a reasonable amount over three months and no significant clinical benefit is observed at 3 months. Improvements are expected to be comparable to those observed in the recently completed MPS I clinical trial and should include improved airway index or resolution of sleep apnea, improved joint mobility, and increased endurance.

EXAMPLE 2

A comprehensive review of the available information for the MPS VI cat and relevant pharmacology and toxicology studies is presented below: Enzyme replacement therapy has been established as a promising treatment for a variety of inherited metabolic disorders such as Gaucher Disease, Fabry Disease and Mucopolysaccharidosis I. In some of these disorders a natural animal model offers the ability to predict the clinical efficacy of human treatment during pre-clinical studies. This was found to be true in MPS I (canine model). With this in mind, studies have been performed with the MPS VI cat prior to the commencement of human studies for this disease. Sufficient safety and efficacy data exist to proceed with a clinical trial in human MPS VI patients.

Studies of rhASB MPS VI cats indicate that no cat has died as a result of drug administration. As predicted, experiments in MPS VI cats also indicate that rhASB uptake is dependent on the presence of mannose 6-phosphate modified carbohydrate sidechains. RhASB in MPS VI cats has also been shown to clear storage from a variety of major organs and moderately alters bone density. Long-term dose-ranging efficacy studies suggest that a dose of 1 mg/kg/week is the lowest concentration to see significant clinical benefits. Studies has also been performed to compare enzyme distribution, clearance of tissue glycosaminoglycan storage, and decrease of urinary glycosaminoglycan levels after bolus and slow (2 hour) infusion. Studies in progress continue to evaluate the safety of weekly infusions of the projected clinical dose of 1 mg/kg of rhASB in cats suffering from MPS VI.

A spontaneous form of MPS VI in several families of Siamese cats was identified in the 1970's (Jezyk, Science 198:834–36 (1977)), and detailed reports of the pathological changes in these animals have been published (Haskins, et al., Am. J. Pathol. 101:657–674 (1980); Haskins, et al., J. Am. Vet. Med. Assoc. 182:983–985 (1983); Konde, et al, Vet. Radiol. 28:223–228 (1987)). Although the clinical presentation of these cats is somewhat variable, they all exhibit general changes that have been reported in the literature (Jezyk, et. al., Science 198:834–36 (1977); Konde, et al., Vet. Radiol. 28:223–228 (1987); Crawley, "Enzyme replacement therapy in a feline model of mucopolysaccharidosis type VI" PhD thesis, University of Adelaide, Adelaide, S. Australia, (1998)). Table 6 has been constructed from these sources to provide the "average" changes one would expect to observe in an untreated MPS VI cat:

TABLE 7

MPS VI Cat Model

| Clinical Observation | Timing of Onset | Changes Relative to Human disease (independent of time) |
|---|---|---|
| Facial dysmorphia: Small head, Broad maxilla, Small ears | 2 months | Similar to human disease |
| Diffuse corneal clouding | 2 months | Similar to human disease |
| Bone abnormalities: Epiphyseal dysplasia, Subluxations, Pectus excavatum | First signs at 2 months — progressive | Similar to human disease — alterations in enchondral calcification |
| Reduced body weight | 3 months | Similar to human disease |

TABLE 7-continued

MPS VI Cat Model

| Clinical Observation | Timing of Onset | Changes Relative to Human disease (independent of time) |
|---|---|---|
| Reduced cervical spine flexibility | Normal cat value is 180° at all ages. In MPS VI: 3 months: 130–170° 5 months: 45–130° 6 months: 30–100° 11 months: 20–80° | Similar to human disease |
| Osteoporosis/ Degenerative Joint Disease | 1 year or more | Similar to human disease |
| Hind limb gait defects | See table below | Carpal tunnel syndrome |
| Hind limb paresis or paralysis (thoracolumbar cord compressions) | | $C_1$–$C_2$ subluxation, Cervical cord compression secondary to thickened dura more typical |
| Grossly normal liver and spleen | | Liver and spleen enlarged in humans |
| Thickened cardiac valves | | Similar to human disease |
| No CNS lesions — mild lateral ventricle enlargement | | May be comparable to hydrocephalus in human disease |

Other biochemical/morphological determinations indicate that by 35 days, organs of untreated cats have maximal storage of glycosaminoglycans in tissues (Crawley, et al., *J. Clin. Invest.* 99:651–662 (1997)). Urinary glycosaminoglycan levels are elevated at birth in both normal and MPS VI cats but after approximately 40 days, normal cats have decreased levels. MPS VI cats urinary glycosaminoglycans remain elevated or continue to increase until reaching steady state after approximately 5 months.

Variability in clinical presentation is seen in affected littermates. In addition to some variability in the timing of onset of particular abnormalities, the time course of progression for some of the clinical and pathological changes is also variable. In general, the bone lesions are typically progressive (Konde et al., *Vet. Radiol.* 28:223–228 (1987)), while the corneal clouding is not. In addition, some paralyzed cats have been noted to improve to severe paresis with time. Studies detailing disease progression in individual cats are limited to clinical (or radiographic) observations. Some of these have distinct pathological correlations, such as neurological deficit and cord compression secondary to proliferation of bony tissue in the thoracolumbar region (Haskins, et al., *J. Am. Vet. Med. Assoc.* 182:983–985 (1983)).

A six-month efficacy study enzyme replacement therapy using recombinant feline ASB in newborn MPS VI cats was conducted. This was prompted by the observation that several treated MPS VI cats developed antibodies to the human enzyme (refer to section 6.5). These antibodies may alter uptake and stability of the enzyme (Brooks, et al., *Biochim. Biophys. Acta* 1361:203–216 (1997)). Feline enzyme was infused at 1 mg/kg weekly. The major conclusions of the study were that urinary GAG, body weight/ growth, bone morphometry and clearance of stored material from several tissues was improved relative to the same dose of human recombinant enzyme used in the previous study, that antibodies were not detected beyond the range observed in normal cats, and that the feline enzyme dose at 1 mg/kg was comparable in reversing disease as the human enzyme dose at 5 mg/kg in a head-to-head comparison (Bielicki, et al., *J. Biol. Chem.*, 274:36335–43 (1999)). These studies indicate that an incremental improvement in endpoints and immunogenicity is possible when the cat-derived enzyme is given to cats. This provides additional support to dosing human patients with the human enzyme at 1 mg/kg/week. The results of this study are set forth in Table 7.

TABLE 8

Efficacy of Weekly Bolus Injections of CHO-derived Recombinant Feline ASB in Newborn MPS VI Cats

| | Results | |
|---|---|---|
| Dose | 1 mg/kg | |
| Duration | 6 months (n = 2) | 3 months (n = 3) |
| Urinary GAGS | Decreased to 2x normal | Decreased to 2x normal |
| Antibody titers | Within range observed in normal cats | To be completed |
| Clinical | | |
| Appearance | Persistent corneal clouding | Persistent corneal clouding |
| | Some resolution of facial dysmorphia | Some resolution of facial dysmorphia; |
| | Improved body shape | Improved body shape |
| Weight | Heavier than normal | Slightly, lighter than normal |
| Spine Flexibility (normal = 180°) | 160°–180° | Not examined |
| Neurological | Normal | Normal |
| Radiology | Improved quality Density and dimensions of bone (similar to 1 mg/kg rh4S in ref. 10) | Not examined |
| Gross | | |
| Bone/Cartilage Thickness | Variable; decreased cartilage thickness more uniform subchondral bone (similar to 1 mg/kg rh4S[a]) | Not examined |
| Spinal Cord | No compressions present | Not examined |
| Cellular Level | | |
| Liver (Kupffer) | Complete lysosomal storage clearing | Complete lysosomal storage clearing |
| Skin | Almost complete reduction is storage | Mild reduction |
| Cornea/Cartilage (ear, articular) | No clearance of lysosomal storage compared with untreated MPS VI controls | No clearance of lysosomal storage |
| Heart Valves | Significant reduction in lysosomal storage | To be completed |
| Aorta | Almost complete reduction in lysosomal storage | Mild reduction in lysosomal storage |

Table 9 provides a summary of all studies performed using recombinant human ASB in the MPS VI cat model.

TABLE 9

RhASB Study Results

| No. Cat | Dose | Duration (Mo.) | Route of Administration | Urinary GAGS | Histopathology |
|---|---|---|---|---|---|
| 1 | 0/8 mg/kg/14 d | 7–22 | Bolus i.v. | Decreased 50% compared to untreated cat | Normalization of vacuolization in liver |
|   | 1.5 mg/kg/7d | 22–27 | Bolus i.v. |   | Significant reduction in kidney and skin |
| 1 | 0.5 mg/kg/14 d | 12–23 | Bolus i.v. | Decreased to near normal | No correction in cornea and chondrocytes |
|   | 1.4 mg/kg/7 d | 23–27 | Bolus i.v. |   | No kidney immune complex deposition |
| 1 | 0.8 mb/kg/14 d | 2–15 | Bolus i.v. |   |   |
| 1 | 0.2 mg/kg/8 d | 6 | Bolus i.v. | Marginal reduction compared to untreated | N/A |
| 4 | 1 mg/kg/7 d | 5/6 | Bolus i.v. | Decreased and maintained at 3 × normal compared to untreated at 10 × normal | Complete lysosomal storage clearing in liver cells<br>No evidence or renal impairment or glomerular immune complex deposition<br>Significant reduction of lysosomal storage in heart valves<br>Gradient storage content from media to adventia in aorta |
| 1 |   | 11 | Bolus i.v. |   | Mild reduction of lysosomal storage of skin (hip joint, dura, kidney)<br>No evidence of renal impairment or glomerular deposition<br>No significant changes in lysosomal storage of cornea/cartilage |
| 2 | 5 mg/kg/7 d | 5/6 | Bolus i.v. | Decreased and maintained at 2 × normal compared to untreated at 10 × normal | Complete lysosomal storage in clearing in liver and skin (hip joint, dura, kidney)<br>No evidence of renal impairment or glomerular deposition<br>Near complete reduction in lysosomal storage in heart valves<br>Thin band of vacuolated cells in outer tuncia media |
| 1 |   | 11 | Bolus i.v. |   | No evidence of renal impairment or glomerular deposition<br>Near complete reduction of lysosomal storage in heart valves<br>Thin band of vacuolated cells in outer tuncia media |
| 2 | 0.5 mg/kg | 6 | Bolus i.v. | Decreased to 3 × normal | Complete lysosomal clearing in liver |
| 2 | 2 × weekly |   |   |   | Mild to moderate reduction in skin<br>Variable reduction of lysosomal storage of heart valves<br>Mild reduction of lysosomal storage in aorta |
| 2 | 1 mg/kg/7 d | 1 | Long infusion (2 hr) | Reduced after first or second infusion to below untreated MPS VI cats | Reduction of lysosomal storage in reticuloendothelial cells and very mild in heat valve and aorta after 5 infusion |
| 2 |   |   | Short infusion (10 min) |   |   |
| 5 | 1 mg/kg/7 d | 6 | Long infusion (2 hr) |   |   |

EXAMPLE 3

Distribution and Feasibility

An initial study was performed to document enzyme uptake and distribution, and to serve as a pilot study of potential endpoints for future efficacy studies (Crawley, et al., *J.Clin.Invest.* 97:1864–1873 (1996)). Recombinant human ASB was administered by bolus injection to affected cats once per week or once every two weeks at 0.5 up to 1.5 mg/kg. Evaluation of one untreated MPS VI cat (Cat D), and one normal cat provided the values from which comparisons were drawn. The data from the one untreated cat was further supported by historical assessment of 38 additional untreated cats. The acute uptake and distribution studies were conducted in normal cats using an immune assay technique that allowed the detection of human ASB in the presence of normal cat enzyme.

The major conclusions of these studies demonstrated wide uptake of enzyme with the expected predominance of liver and spleen uptake as observed in other enzyme replacement studies in MPS animal models. The uptake efficiency was dependent on the presence of mannose 6-phosphate modified carbohydrate side-chains on the enzyme. The half-life of the enzyme was determined to be 2–4 days. Therapeutically, the enzyme did clear storage from a variety of major organs and did moderately alter bone density. The cornea, bone morphology and cartilage defects were not effectively treated in older MPS VI cats. The study results are summarized in Table 10.

TABLE 10

Summary: Distribution/Feasibility MPS VI Cat Study

| Parameter | Findings | | |
|---|---|---|---|
| Cat | A | B | C |
| Dose | Treated MPS VI 0.8 mg/kg per 14 d  1.5 mg/kg per 7 d | Treated MPS VI 0.5 mg/kg per 14 d  1.4 mg/kg per 7 d | Treated MPS VI 0.8 mg/kg per 14 d |

TABLE 10-continued

Summary: Distribution/Feasibility MPS VI Cat Study

| Parameter | Findings A | B | C |
|---|---|---|---|
| Cat | | | |
| Age at dose (mo.) | 7*–22   22–27 | 12*–33   23–27 | 2*–15 |
| Infusion Parameters | 2–10 ml (PBS) via cephalic v. for 5–20 minutes | | |
| Plasma $t_{1/2}$ (i.v. bolus) | 13.7 ± 3.2 min @ 1 mg/kg | | |
| | 45 min @ 7.5 mg/kg | | |
| | All values relative to endogenous feline ASB enzyme four hours after infusion of 1 mg/kg rhASB in normal cats | | |
| | Liver: 495x | | |
| | Spleen: 6x | | |
| | Lung: 22.3x | | |
| | Heart: 4.3x | | |
| | Aorta: 4x | | |
| | Skin: 31x | | |
| | Cartilage: 0x | | |
| | Cornea: 0x | | |
| Tissue $t_{1/2}$ | 2–4 days @ 1 mg/kg in most organs (detectable enzyme in most tissues of cat B, but only in liver of A after 7 days) | | |
| Neurological | Ambulation fluctuated, but improved on higher dose | N/A | Marginal progression to paretic gate by end of study |
| Corneal Opacity | Did not change with therapy (slit lamp exam 3x late in rx) | | |
| Skeletal (x-rays) | Lesions progressed (no radiographic improvement | | |
| 4 views every 3 mo. | Increased bone volume/trabecular # in cat C (received earlier rx) | | |
| | Vertebral compression in cat C | | |
| Anaphylaxis | No anaphylaxis, minimal distress on infusion; | | |
| Antibody response (Ig titers) Untreated MPS VI = 4,000–32,000 | $1 \times 10^6$ (plasma could inhibit enzyme activity in vitro) | 64,000 | 64,000 |
| Urinary GAGS (at ~400 days) | Decreased 50% compared to untreated cat | Decreased to near normal | |
| Urinary dermatan sulfate (~400 days) | Midway for all 3 cats (relative to untreated control D and normal) | | |
| Body Weight | 2.5–3.0 kg vs. normal 4–7 kg | | |
| Liver/Spleen | Grossly normal | | |
| Heart Valves | Grossly normal | | |
| Cartilage | Abnormal thickness and formation | | |
| Microscopy (vacuolization) | Normalization of vacuolization in liver, Significant reduction in kidney and skin, No correction in cornea and chondrocytes | | |
| Kidney immune complex deposition | Absent | | |

EXAMPLE 4

Efficacy in MPS VI Cats Treated from Birth

A long term dose-ranging efficacy study was performed in MPS VI cats starting at birth (Crawley, et al., *J. Clin. Invest.* 99:651–662 (1997)), and is summarized in Table 10. MPS VI cats were treated weekly with bolus i.v. injections of 0.2, 1 and 5 mg/kg of rhASB beginning at birth. A total of 9 cats were treated for 5, 6 or 11 months. In addition, 12 MPS VI and 9 normal cats were included as untreated controls. The major conclusions are that 0.2 mg/kg dose did not alter disease progression in the one cat studied, and the only documented clinical benefit was a reduction in the storage in liver Kupffer cells. Urinary GAG levels decreased to near normal during the trial in the higher dose groups. In addition to improvements in the major organs, the higher doses of therapy from birth were able to prevent or ameliorate the bony deformity of the spine and the abnormal form of many bones. There was a dose-dependent effect on improvement in L-5 vertebral bone mineral volume, bone trabecular thickness, and bone surface density between the 1 and 5 mg/kg doses, although both were equivalent in improving bone formation rate at 5 to 6 months of ERT (Byers, et al., *Bone* 21:425–431 (1997)). The mitral valve and aorta was dependent on dose and was less complete at 1 mg/kg but nearly complete at 5 mg/kg. No improvement of storage in cartilage and cornea was observed at any dose. The study suggests that the 1 mg/kg/week dose is the lowest concentration to see significant clinical benefit. The study results are summarized in Table 11.

TABLE 11

Efficacy of Weekly Bolus Injections of CHO-derived Recombinant Human ASB in Newborn MPS VI Cats (Study PC-BM102-002)

| | Results | | | |
|---|---|---|---|---|
| Dose | 1 mg/kg | | 5 mg/kg | |
| Duration | 5/6 mo | 11 mo | 5/6 mo | 11 mo |
| N | 4 | 1 | 2 | 1 |
| Biochemical | | | | |
| Urinary GAGs | Decreased and maintained at 3 × normal compared to untreated at 10 × normal | | Decreased and maintained at 2 × normal compared to untreated at 10 × normal | |
| Clinical | | | | |
| Appearance | Variable changes; Persistent corneal clouding by slit lamp | | Variable changes; Persistent corneal clouding by slit lamp | |
| Weight | Intermediate (no rx vs. normal) | | Intermediate (no rx vs. normal) | |
| Spine Flexibility (normal = 180) (untreated MPS VI = 90°) | 130–160° | 90° | 180° | 160° |
| Neurological | 1 of 4 mild hindlimb paralysis | No deficits | No deficits | No deficits |
| Radiology | Improved bone quality, density and dimensions | | Improved bone quality, density and dimensions Possibly superior to 1 mg/kg | |
| Gross | | | | |
| Bone/Cartilage Thickness | Variability, but improved | Degenerative joint disease present | Variability, but improved | Degenerative joint disease present |
| Spinal Cord | 1 of 4 with several mild compressions | No compressions | No cord compressions | |
| Cellular Level | | | | |
| Liver (Kupffer) | Complete lysosomal storage clearing | Maintained | Complete lysosomal storage clearing | Maintained |
| Skin (hip Joint, Dura, Kidney) | No evidence of renal impairment or glomerular immune complex deposition | Mild reduction in lysosomal storage No evidence of renal impairment or glomerular deposition | Complete lysosomal storage clearing No evidence of renal impairment or glomerular deposition | Maintained No evidence of renal impairment or glomerular deposition |
| Cornea/Cartilage (ear, articular) | NA | No significant changes in lysosomal storage | NA | No significant changes in lysosomal storage |
| Heart Valves | Significant (Variable) reduction in lysosomal storage | Significant (variable) reduction in lysosomal storage near complete | Near complete reduction in lysosomal storage | |
| Aorta | Gradient of storage content from media to adventitia | | Thin band of vacuolated cells in outer tunica media | |

EXAMPLE 5

Efficacy of Twice Weekly Infusions of Recombinant Human ASB in Newborn-MPS VI Cats A six-month study was performed in newborn cats to evaluate a 0.5 mg/kg infusion given twice weekly. In addition, the enzyme used in this study was derived exclusively from the CSL-4S-342 cell line. The major conclusions of the study include that compared with the previously reported 1 mg/kg weekly dose, this study produced similar improvements in physical, biochemical, neurological and radiographic parameters. The most notable differences were slightly worsened cervical spine flexibility, and less clearance of lysosomal storage in the denser connective tissues such as the heart valves and aorta. The results are summarized in Table 12.

TABLE 12

Efficacy of Twice Weekly Bolus Injections of CHO-derived Recombinant Human ASB in Newborn MPS VI Cats

| Parameter | Results |
|---|---|
| Dose | 0.5 mg/kg |
| Duration | 2x weekly: 6 months (n = 2; cats 225 f, 226 m) |
| Urinary GAGs | Decreased to 3x normal |
| Antibody titres | Within range observed in normal cats |
| Clinical | |
| Appearance | Persistent corneal clouding |
| | Some resolution of facial dysmorphia |
| | Improved body shape |
| Weight | Intermediate (between no treatment and normal) |
| Spine Flexibility (normal = 180°) | 90°–150° |
| Neurological | No hind limb paralysis |
| Radiology | Improved quality, density and dimensions of bone (similar to 1 mg/kg rh4S in ref. 110 |
| Gross | |
| Bone/Cartilage Thickness | Variable; decreased cartilage thickness and more uniform subchondral bone (similar to 1 mg/kg rh4S$^a$) |
| Spinal Cord | No compressions present |
| Cellular Level | |
| Liver (Kupffer) | Complete lysosomal clearing |
| Skin | Mild to moderate reduction in storage |
| Cornea/Cartilage (ear, articular) | No clearance of lysosomal storage compared with untreated MPS VI controls |
| Heart Valves | Variable reduction in lysosomal storage (complete in 225 f; no change from untreated in 226 m) |
| Aorta | Mild reduction in lysosomal storage |

EXAMPLE 6

Evaluation of Enzyme Uptake and Distribution as a Function of the Rate of Enzyme Infusion in MPS VI Cats The primary goal of this study was to compare enzyme distribution, clearance of tissue GAG storage, and decrease of urinary GAG levels after bolus infusion and after slow (2 hour) infusion of an identical 1 mg/kg dose. The slow administration proposal is based on experience from preclinical and clinical studies of α-L-iduronidase for the treatment of MPS I. In addition, the study provided the first data that enzyme produced at BioMarin from cell line CSL4S-342 is biologically active and safe. Major conclusions of the study include that all four cats (two per group) treated in this study showed no acute adverse reaction to either the slow or fast infusion, and no detrimental effects of repeated enzyme infusions. However, bolus infusion results in high liver uptake which is not preferred. Slow infusion provides better distribution into tissues and therefore is a preferred method for clinical trial.

The tissue distribution of rhASB obtained in the study suggested that 2-hour infusions might increase enzyme levels in other organs apart from the liver, including increased activity in the brain. Reduction in urinary GAG was observed immediately after the first or second infusion to levels below the range observed in untreated MPS VI cats. Correction of lysosomal storage was observed in reticuloendothelial cells and very mild in some fibroblasts (heart valve) and smooth muscle cells (aorta) after 5 infusions. No other significant clinical response to infusions was observed in either group, however this was not unexpected due to the short duration of the study, and due to therapy starting after significant disease changes had already developed. The extended 2-hour infusion was safe and well tolerated relative to the shorter protocols used in previous studies. The 2-hour infusion may provide improvement in enzyme distribution based on the one cat that was evaluable for enzyme tissue distribution.

EXAMPLE 7

Month Safety Evaluation of Recombinant Human N-acetylgalactosamine-4-sulfatase in MPS VI Affected Cats Two 6 month studies in MPS VI cats have been initiated using the enzyme produced by the manufacturing process according to the present invention. The purpose of these studies is to evaluate the safety and efficacy of weekly infusions of the projected human clinical dose of rhASB in cats suffering from MPS VI. Study 6 involves kittens dosed initially at 3 to 5 months of age. Study 7 involves kittens treated from birth with weekly infusions of the projected human clinical dose of rhASB. The studies are intended to access potential toxicology. Cats will be observed for changes in behavior during infusion of the recombinant enzyme to assess possible immune responses. Serum will be monitored for complement depletion and for the formation of antibody directed against the recombinant enzyme. General organ function will be monitored by complete clinical chemistry panels (kidney and liver function), urinalysis, and complete blood counts (CBC) with differential Urinary glycosaminoglycan levels will be monitored on a weekly basis at a set time points relative to enzyme infusion. Evidence of clinical improvements in disease will be documented. These data will provide additional assessment of the potential efficacy of the treatment and will validate the activity and uptake of the enzyme in vivo. The studies have and will be conducted in a manner consistent with the principles and practices of GLP regulations as much as possible.

Preliminary results of the first study indicate that administration of rhASB has not had any detrimental effects on any of the animals, with bodyweights and clinical chemistries generally maintained within reference ranges. However, both of the cats with significantly elevated antibody titers developed abnormal clinical signs during infusions, however both animals behaved normally once enzyme infusions ceased and did not appear to suffer any longer tern ill effects. Extended infusion times (4 hours) and increased premedication antihistamines have allowed continued therapy in the cats without any abnormal clinical signs. Mild reduction in urinary GAG levels suggest some efficacy of therapy in reducing stored glycosaminoglycans in tissues or circulation, however fluctuations in these levels were observed over time making interpretation difficult. None of the 5 cats have shown obvious clinical improvements in response to ERT, but this will require at least 6 month treatment based on previous studies[23]. Antibody titers have developed in four out of the five cats, with noticeable increases in titers observed after 2 months of ERT. Two of these cats have developed significantly elevated titers after 2 or 3 months.

EXAMPLE 8

Safety Profile for MPS VI, Cats Treated with rhASB

A study has commenced enrolling affected cats that were treated within 24 hours of birth. Forty-one MPS VI cats have been treated using rhASB. Administration of enzyme to normal cats has been restricted to one to two cats to confirm acute safety of new batches prior to exposure of the valuable affected animals to therapy. In summary, no MPS VI cat has died as a result of drug administration, although four cats have died as a result of viral infection or an underlying congenital abnormality. Enzyme for the studies was produced according to the production methods of the present invention. The preliminary data are set forth in Table 13

TABLE 13

MPS VI Cat Efficacy Study Summary from Hopwood Laboratory

| Study # | # of Cats | Dose/wk (mg/kg) | Rx Length (mos.) | Mortality |
|---|---|---|---|---|
| 1 | 2 | Variable | 13–21 | None |
|  | 1 |  |  |  |
| 2 | 1 | 0.2 | 5 | None |
| 2 | 1 | 0.2 | 1 | Died: congenital heart defect |
| — | 2 | 0.5 | 3–5 | 1 died parvovirus |
| 2 | 4 | 1 | 3–11 | 1 died parvovirus |
|  | 2 |  |  |  |
| — | 1 | 1 | 6 (s.c.) | None |
| — | 4 | 1 | 6 | None |
| 2 | 2 | 5 | 3–11 | 1 died parvovirus |
|  | 2 |  |  |  |
| 4 | 2 | 0.5 (twice) | 5 | None |
| — | 3 | 0.5 (twice) | 5 | None |
| 5 | 4 | 1 | 1 | None |
| 6 | 5 | 1 | Started | None |
| 7 | 5 | 1 | Started | None |

EXAMPLE 8A

Tissue Distribution with Slow Infusion

A separate study was undertaken to compare the rate of uptake and tissue distribution of rhASB in young MPS VI cats (<10 weeks old at initiation) using a long (two hours) or a short-infusion (10–15 minutes) protocol (ASB-PC-004). Seven normal cats (12–24 months old) were sedated and had femoral artery cannulae implanted to allow blood sampling. rhASB at a dose of 1.0 mg/kg or 7.3 mg/kg was infused into the cephalic vein in a volume of 7 mL over 40 seconds. Serial heparinized arterial blood samples were obtained at approximately 2, 4, 6, 8, 10, 20, 30, 40, 60 and 120 minutes post-dose. Plasma was collected by centrifugation and frozen until analysis. After four hours, animals were euthanized and tissues were collected, weighed and frozen until analysis.

In a separate study, three normal cats (8–66 months old) received a 1.0 mg/kg IV bolus dose of rhASB in a 7 mL dose volume. One cat per time point was euthanized at 2, 4 or 7 days post-dose. Selected tissues were collected, weighed and frozen until analysis. One additional normal cat, not exposed to rhASB, was euthanized to provide feline ASB levels in tissues for analytical comparisons. rhASB or feline ASB were quantitated in plasma and tissues was performed using an ELISA assay technique. rhASB in samples was adsorbed to an immobilized anti-rhASB monoclonal antibody and feline ASB was absorbed to a polyclonal anti-rhASB antibody that cross-reacts with feline ASB. The absorbed ASB was then quantitated using afluorescent substrate.

Plasma concentration analyses showed that the t½ of rhASB at the 1.0 mg/kg dose was 13.7±3.2 minutes and was ≅45 minutes for the 7.3 mg/kg dose. Tissue t½ following the 1.0 mg/kg dose ranged from 2.4–4.2 days in the liver, spleen, lung, kidney and heart. Low, but detectable levels were seen in these tissues (except heart) up to seven days following dosing. Four hours after a dose of 1.0 mg/kg ASB, the majority of the dose delivered to the liver, was detected in all tissues measured except cartilage and cornea, with the majority in the liver. With the exception of the cerebrum and cerebellum, levels were 4-(aorta) to 495-(liver) fold higher than those of feline ASB in the untreated control cat. The tissue half-lives determined in this study (2.4–4.2 days at 1.0 mg/kg) support the weekly clinical dosing frequency.

The primary objective of this study was to evaluate the effects of infusion rate on enzyme distribution, clearance of tissue GAG storage, and decrease of urinary GAG levels. Groups (n=2/group) of 10-week-old MPS VI cats were administered short (10–15 minutes) or long (two hours) IV infusions of rhASB, 1.0 mg/kg once weekly for five weeks. Animals were euthanized two days after the last infusion and selected tissues (liver, spleen, heart, lung, kidney, skin, aorta, cerebrum, cerebellum, cartilage, cornea and lymph nodes) were collected for determination of ASB activity and for histopathological evaluation. Tissues were stored frozen until analysis. The study employed the same immune assay to determine the tissue ASB levels as described above (ASB-PC-001). One cat in the two-hour infusion group had reduced tissue enzyme levels compared to the other treated cats. High levels of enzyme were detected around the catheterization site following the last dose while low levels were seen in the contralateral limb. These findings suggest that the catheter had dislodged prematurely and had contributed to the low tissue levels of ASB seen in the tissues from this animal. Comparison of enzyme activities in the remaining three cats showed increased enzyme activity in the liver, lung, kidney, cerebrum and cerebellum and reduced activity in the mesenteric lymph nodes of the two-hour infusion cat relative to the 10-minute infusion animals. No enzyme was found in the skin, cartilage and corneas. Although the data from this study is limited; the findings from this study suggest that two-hour infusions may result in increased enzyme levels in the tissues (apart from the liver) relative to 10-minute infusions, indicating that the extended infusions provide better tissue distribution.

EXAMPLE 9

Method of Manufacture and Purification (Perfusion Process)

A process flow diagram comparing the purification processes for the fed batch and perfusion-based cell culture processes is provided in Table 14. Comparisons to the fed batch purification process as well as details of the specific changes implemented for the purification of the perfusion process material are summarized in Table 15. Table 16 depicts the purification method used for the perfusion-based cell cultures.

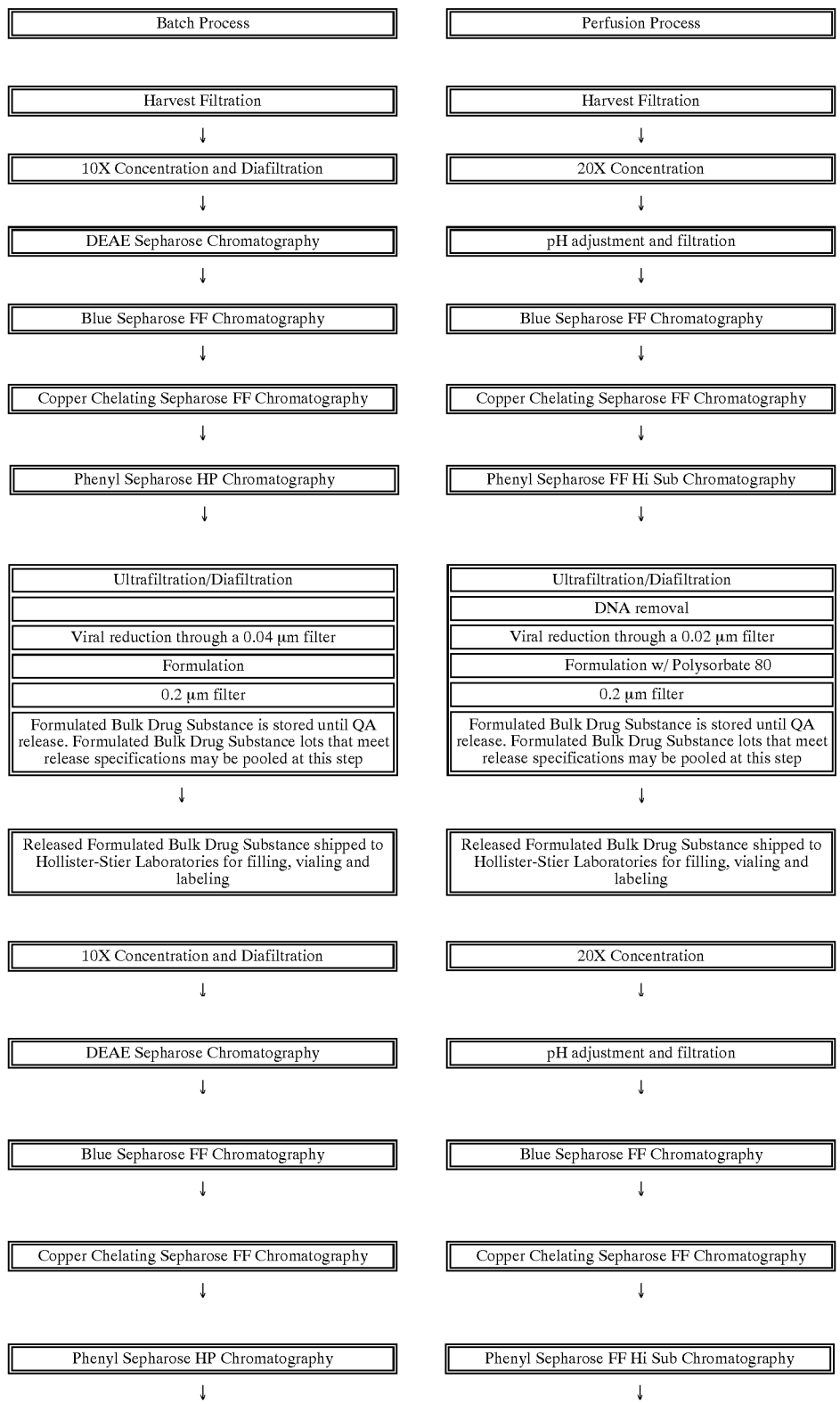

Purification Process Comparison between Batch and Perfusion Processes

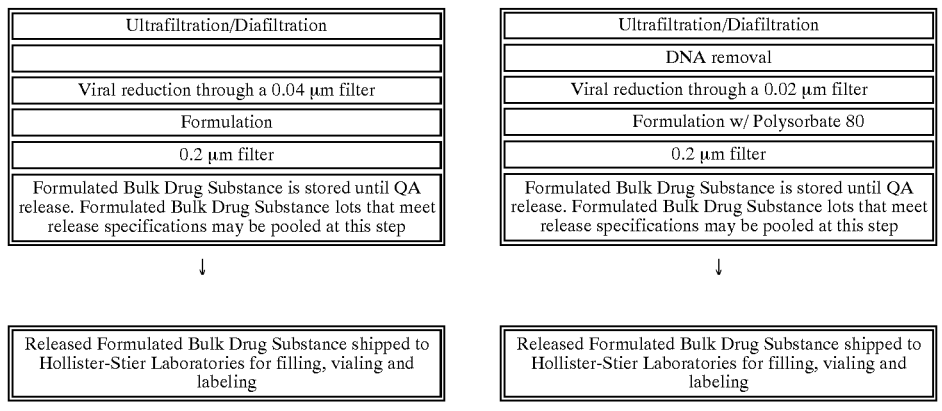

TABLE 15

Summary Description of Purification Changes

| Production Step | Description (Batch) | Description (Perfusion) |
|---|---|---|
| PURIFICATION PROCESS | | |
| Concentration/ Diafiltration | Tangential Flow Filtration: 2.8 m$^2$ Albumin retentive MWCO filters Operation: Concentration to 10X Diafiltered against 5 volumes 10 mM sodium phosphate, 100 mM sodium chloride, pH 7.3 | Changes: Tangential Flow Filtration: 5.6 m2 Albumin retentive MWCO filters Operation: Concentration to 20X No diafiltration, system rinsed with 100 mM sodium phosphate, pH 7.3 Rationale: Reduction of volume for storage at 4° C. |
| | ↓ | |
| DEAE Sepharose FF Flow-Through Chromatography | Column: 2 × 30 cm diameter × 33 cm height Pre-Wash: 0.1 N sodium hydroxide Wash: Water-for-Injection (WFI) Neutralize: 100 mM sodium phosphate, pH 7.3 Equilibration: 10 mM sodium phosphate, 100 mM sodium chloride; pH 7.3 Load: concentrated/diafiltered harvest Wash: 10 mM sodium phosphate, 100 M sodium chloride, pH 7.3 Strip: 10 mM sodium phosphate, 1.5 M sodium chloride, pH 7.3 Regeneration: 10% glacial acetic acid Wash: Water-for-Injection (WFI) Sanitization: 0.5 N sodium hydroxide Storage: 0.1 N sodium hydroxide | Step deleted |
| | ↓ | |
| pH adjustment and filtration | | pH adjustment: addition of 10% glacial acetic acid to pooled 20X concentrates to a final pH 5.0 Load: pooled 20X concentrates to a Filtration through clarification filters and 2 μm filter Flush: 20 mM sodium acetate, 120 mM sodium chloride, pH 5.0 Rationale: Increases rhASB binding capacity of the subsequent Blue Sepharose resin column. |
| | | ↓ |

TABLE 15-continued

Summary Description of Purification Changes

| Production Step | Description (Batch) | Description (Perfusion) |
|---|---|---|
| Blue Sepharose FF Chromatography | Column 20 cm diameter × 11 cm height Pre-Wash: 0.1 N sodium hydroxide Wash: Water-for-Injection (WFI) Neutralization: 1 M sodium acetate, pH 5.5 Equilibration: 20 mM sodium acetate, 150 mM sodium chloride, pH 5.5 Load: DEAE flow through adjusted to 20 mM sodium acetate, 150 mM sodium chloride, pH 5.5 Wash: 20 mM sodium acetate, 150 mM sodium chloride, pH 5.5 Elution: 20 mM sodium acetate, 500 1.0 M sodium chloride, pH 5.5. Regeneration: 20 mM sodium acetate, 1.0 M sodium chloride, pH 5.5 Sanitization: 0.1 N sodium hydroxide Wash 1: Water-for-Injection Wash 2: 1 M sodium acetate, pH 5.5 Storage: 20% Ethanol ↓ | Change: Column: 45 cm diameter × 16 cm height Neutralization: omitted Equilibration: 10 mM sodium phosphate, pH 6.45 Load: pooled 20X concentrates, pH adjusted to 5.0 and filtered. Wash: 10 mM sodium phosphate, pH 6.45 Elution: 10 mM sodium phosphate, 125 mM sodium chloride, pH 6.45 Regeneration: 10 mM sodium phosphate, 1.0 M sodium chloride, pH 6.45 Wash 2: 10 mM sodium phosphate, 1.0 M sodium chloride, pH 6.45 Rationale: Conditions allow improved removal of potential CHO impurities allowing for the deletion of DEAE Sepharose Chromatography. |
| Copper Chelating Sepharose FF Chromatography | Column: 14 cm diameter × 9 cm height Pre-Wash: 0.1 N sodium hydroxide Wash: Water-for-Injection (WFI) Charge Buffer: 0.1 M cupric sulfate Equilibration: 20 mM sodium acetate, 0.5 M sodium chloride, 10% glycerol, pH 6.0 Load: Adjust glycerol content of Blue Eluate to 10%, by adding 20 mM sodium acetate, 500 mM sodium chloride, 50% glycerol, pH 6.0 Wash 1 20 mM sodium acetate, 0.5 M sodium chloride, 10% glycerol, pH 6.0 Wash 2:20 mM sodium acetate, 0.5 M sodium chloride, 10% glycerol, pH 4.0 Wash 3:20 mM sodium acetate, 0.5 M sodium chloride, 10% glycerol, pH 3.8 Elution: 20 mM sodium acetate, 0.5 M sodium chloride, 10% glycerol, pH 3.6 Regeneration: 50 mM EDTA, 1.0 M sodium chloride, pH 8.0 Sanitization: 0.5 M sodium hydroxide Storage: 0.1 M sodium hydroxide ↓ | Changes: Column: 40 cm diameter × 16 cm height Equilibration: 20 mM sodium acetate, 0.5 M sodium chloride, 10% glycerol, pH 5.5 Load: Adjust glycerol content of pooled Blue Eluate to 10%, by adding 100 mM sodium acetate, 2.0 M sodium chloride, 50% glycerol, pH 5.2 Wash 1: 20 mM sodium acetate, 0.5 M sodium chloride, 10% glycerol pH 5 5 Wash 2: 20mM sodium acetate 0 5 M sodium chloride, 10% glycerol pH 3 9 Wash 3: omitted Rationale Consistent and reproducible product purity obtained with m6dified step |
| Viral Inactivation | Pooled Eluate fractions held for 30–120 minutes prior to adjustment to pH 4.5 with 0.5 M NaOH ↓ | No Change, |
| Phenyl Sepharose Chromatography | Column: 10 cm diameter × 16 cm height Resin: Phenyl Sepharose High Performance Pre-Wash: 0.1 N sodium hydroxide Wash: Water-for-Injection (WFI) Equilibration: 20 mM sodium acetate, 3.0 M sodium chloride; pH 4.5 Load: Adjust sodium chloride content of Copper Eluate to 3 M, by adding 20 mM sodium acetate 5 M sodium chloride, pH 4.5 Wash 1:20 mM sodium acetate, 3.0 M sodium chloride, pH 4.5 Wash 2:20 mM sodium acetate, 1.6 M sodium chloride, pH 4.5 Elution: 20 mM sodium acetate, 1 M sodium chloride, pH 4.5 Regeneration: 20 mM sodium acetate, pH 4.5 Sanitization: 0.5 N sodium hydroxide Storage: 0.1 N sodium hydroxide ↓ | Change: Column: 40 cm diameter × 16 cm height Resin: Phenyl Sepharose High Sub Fast Flow Equilibration: 20 mM sodium acetate, 2.0 M sodium chloride, pH 4.5 Load: Adjust sodium chloride content of Copper Eluate to 2 M, by adding 20 mM sodium acetate, 5 M sodium chloride, pH 4.5 Wash 1:10mM sodium phosphate, 2.0 M sodium chloride, pH 7.1 Wash 2:20 mM sodium acetate, 2.0 M sodium chloride, pH 4.5 Elution: 20 mM sodium acetate, 250 mM sodium chloride, pH 4.5 Rationale: Alternate resin has more favorable flow characteristics and capacity for rhASB. Wash 1 allows more robust clearance of potential protein impurities. |

TABLE 15-continued

Summary Description of Purification Changes

| Production Step | Description (Batch) | Description (Perfusion) |
|---|---|---|
| UF/DF Final | Tangential Flow Filtration: <0.4 m² MWCO 10 kDa Filters.<br>Equilibration: 10 mM sodium phosphate; 150 mM sodium chloride, pH 5.8<br>Concentration: Concentration to NMT 1.5 mg/mL<br>Diafiltration: 10 mM sodium phosphate, 150 mM sodium chloride, pH 5.8 | Change:<br>Tangential Flow Filtration: 2.8 m² MWCO 10 kDa Filters. |
| DNA Removal | Not Done | New Step:<br>DNA Filtration: Product filtered through an ion exchange-based DNA filter<br>Rationale:<br>Additional DNA clearance to compensate for deletion of DEAE Flow-Through Chromatography step. |
| Formulation | Diluted to 1.0 mg/ml with 10 mM sodium phosphate, 150 mM sodium chloride, pH 5.8 | |
| Viral filtration | Viral Filtration: Product filtered through a 0.04 μm filter | Change:<br>Viral Filtration: Product filtered through a 0.02 μm filter<br>Rationale:<br>Use of smaller pore size to enhance viral clearance. |
| Formulation | Step occurs earlier in process (Prior to viral filtration) 5.8 | Change:<br>Diluted to 1.0 mg/ml with 10 mM sodium phosphate, 150 mM sodium chloride, pH 5.8<br>Formulation: Polysorbate 80 is added to a concentration of 50 μg/mL. |
| Filtration | Filtration: Filter the diluted product through a 0.2 μm filter into storage container | No Change |

TABLE 16 rhASB Purification Method (Perfusion Process)

| Step | Process |
|---|---|
| Harvest Filtration | Filtration through Clarification filters, 0.45 μm filters and finally 0.2 μm filter. Filtered polled harvests are stored in polypropylene bags |
| UF Concentration | Equilibration and flush: 100 mM sodium phosphate, pH 7.3<br>Load: filtered harvest fluid<br>Concentration: Concentration to 20X<br>Filtration: Filter the diluted product through a 0.2 μm filter into storage container |
| pH adjustment and filtration | pH adjustment: Add 10% glacial acetic acid to pooled 20X concentrates to a final pH of 5.0<br>Load: pooled 20X concentrates<br>Rinse: Water-for Injection (WFI)<br>Filtration through Clarification filters and 0.2 μm filter:<br>Flush: 20 mM sodium acetate, 120 mM sodium chloride, pH 5.0 |
| Blue Sepharose 6 FF (Blue, Blue Sepharose) | Pre-Wash: 0.1 N sodium hydroxide<br>Wash: Water-for-Injection (WFI)<br>Equilibration: 10 mM sodium phosphate, pH 6.45<br>Load: pH adjusted and filtered pooled 20X concentrates<br>Wash: 10 mM sodium phosphate, pH 6.45<br>Elution: 10 mM sodium phosphate, 125 mM sodium chloride, pH 6.45<br>Regeneration: 10 mM sodium phosphate, 1.0 M sodium chloride, pH 6.45<br>Sanitization: 0.1 N sodium hydroxide<br>Wash 1: Water-for-Injection (WFI)<br>Wash 2: 10 mM sodium phosphate, 1.0 M sodium chloride, pH 6.45<br>Storage: 20% Ethanol |

TABLE 16-continued rhASB Purification Method (Perfusion Process)

| Step | Process |
|---|---|
| Chelating Sepharose FF (Copper, CC, Copper-Chelating) | Pre-Wash: 0.1 N sodium hydroxide<br>Wash: Water-for-Injection (WFI)<br>Charge Buffer: 0.1 M cupric sulfate<br>Equilibration: 20 mM sodium acetate, 0.5 M sodium chloride, 10% glycerol, pH 5.5<br>Load: Adjust glycerol content of pooled Blue Eluates to 10%, by adding 100 mM sodium acetate, 2.0 M sodium chloride, 50% glycerol, pH 5.2<br>Wash 1: 20 mM sodium acetate, 0.5 M sodium chloride, 10% glycerol pH 5.5<br>Wash 2: 20 mM sodium acetate, 0.5 M sodium chloride, 10% glycerol pH 3.9<br>Elution: 20 mM sodium acetate, 0.5 M sodium chloride, 10% glycerol, pH 3.6<br>Eluate hold for 30–120 minutes prior to adjustment to pH 4.5 with 0.5 M NaOH<br>Regeneration: 50 mM EDTA, 1.0M sodium chloride, pH 8.0<br>Sanitization: 0.5M sodium hydroxide<br>Storage: 0.1M sodium hydroxide |
| Phenyl Sepharose 6 FF High Sub (Phenyl, Phenyl High Sub) | Pre-Wash: 0.1 N sodium hydroxide.<br>Wash: Water-for-Injection (WFI)<br>Equilibration: 20 mM sodium acetate, 2.0 M sodium chloride, pH 4.5<br>Load: Adjust sodium chloride content of Copper Eluate to 2 M, by adding 20 mM sodium acetate, 5 M sodium chloride, pH 4.5<br>Wash 1: 10 mM sodium phosphate, 2.0 M sodium chloride, pH 7.1<br>Wash 2: 20 mM sodium acetate, 2.0M sodium chloride, pH 4.5<br>Elution: 20 mM sodium acetate, 250 mM sodium chloride, pH 4.5<br>Regeneration: 20 mM sodium acetate, pH 4.5<br>Sanitization: 0.5 N sodium hydroxide<br>Storage: 0.1 N sodium hydroxide |
| UF/DF, DNA Filtration, Viral Filtration, Formulation | Equilibration: 10 mM sodium phosphate, 150 mM sodium chloride, pH 5.8<br>Concentration: Concentration to NMT 1.5 mg/mL<br>Diafiltration: 10 mM sodium phosphate, 150 mM sodium chloride, pH 5.8<br>DNA Filtration: Product filtered through a DNA filter<br>Viral Filtration/Dilution: Product filtered through a 0.02 μm filter and diluted to 1.0 mg/ml<br>Formulation: Polysorbate 80 at a concentration of 50 μg/mL is added<br>Filtration: Filter the diluted product through a 0.2 μm filter into storage container |

All purification columns are regenerated prior to use, sanitized after use and stored in the appropriate buffers as indicated in Tables 15 and 16.

Purification Raw Materials

All materials are supplied by qualified vendors.

TABLE 17

Raw Materials for Purification

| Ingredient | Grade |
|---|---|
| Glacial Acetic Acid | USP |
| Cupric Sulfate Pentahydrate | USP |
| Edetate Disodium | USP |
| Dehydrated Alcohol, USF (Ethanol, 200 Proof) | USP |
| Glycerine | USP |
| Sodium Acetate, Trihydrate | USP |
| Sodium Chloride | USP |
| Sodium Hydroxide 50% w/w Solution | Reagent Grade |
| Sodium Phosphate, Dibasic, Heptahydrate | USP/EP |
| Sodium Phosphate, Monobasic, Monohydrate | USP |
| Hydrochloric Acid, 6 N Volumetric Solution | Reagent Grade |
| Polysorbate 80, MF/EP (CRILLE 4 HP) | NF/EP |
| Water-for-Injection, Packaged in Bulk | USP |

The glycerine to be utilized is to be derived from a synthetic process. All raw materials used are to be in compliance with the latest version of the CPMP/CVMP Note for Guidance entitled, "Minimising the Risk of Transmitting Animal Spongiform Encephalopathy Agents Via Human and Veterinary Medicinal Products," in which tallow derivatives such as glycerol and fatty acids manufactured by rigorous processes involving high temperatures and pressure conditions or chemical reactions known to be terminally hostile to the bovine spongiform encephalopathic (BSE) agent are thought unlikely to be infectious. Thus, the risk of BSE transmission from the glycerine is considered to be low.

The viral safety of rhASB is confirmed by a combination of selection and qualification, of vendors, raw material testing, cell bank characterization studies, viral removal studies and inactivation capacity of the rhASB purification process, and routine lot release testing. Relevant US, EU, and ICH regulations and guidelines have been referenced to ensure the viral safety of rhASB.

Column Chromatography, DNA Removal and Viral Filtration

RhASB is now purified using a series of chromatography and filtration steps. The harvest fluid is concentrated to 20× by ultrafiltration, pH adjusted, filtered and loaded onto a Blue Sepharose Fast Flow chromatography column (45 cm×16 cm). The Blue Sepharose Fast Flow eluate is filtered prior to loading on to a Copper Chelating Sepharose column. The Copper eluate is filtered prior to loading on to a Phenyl Sepharose Fast Flow High Sub column. All three column chromatography purification steps are run in a bind and elute mode. The Phenyl Sepharose column eluate is passed through an anion exchange filter and viral reduction filter prior to concentration and buffer exchange by ultrafiltration.

Viral Removal/Inactivation Studies

Two studies were conducted to assess the viral reduction capacity of the modified rhASB purification process. Studies were performed at BioReliance (Rockville, Md.) using two model virus systems, Xenotropic murine leukemia virus (XMuLV) and Murine Minute Virus (MMV). XMuLV is an enveloped single-stranded RNA retrovirus with low resistance to physico-chemical inactivation. MMV is a small, non-enveloped single-stranded DNA virus with high resistance to physico-chemical agents.

These studies evaluated two chromatographic steps (Copper Chelating Sepharose FF and Phenyl Sepharose FF High Sub) and the viral filter (0.02 μm) used in the rhASB purification process. Spike and recovery studies were performed using scaled down versions of the process steps. The critical parameters maintained were retention times and matrix-solution interactions. This was achieved by replicating the buffers, linear flow rates and column heights but adjusting for column diameter. Materials used in the study (product and buffers) were collected from actual full scale production.

Chromatography columns (Copper Chelating Sepharose and Phenyl Sepharose) were packed and pre-run with either typical rhASB loads (blank) or loads spiked with viral buffer prior to shipping to BioReliance. Chromatograms and product yields in the presence of viral buffers were comparable to blank runs. Identical column loads were spiked with either XMuLV or MMV, immediately prior to chromatography. The amount of viral reduction for each of the evaluated steps was determined by comparing the viral burden in the column loads and eluates. A summary of the results for this study are shown in Table 18.

TABLE 18

Reduction Factors for XmuLV and MMV

| Process Step | XMuLV Log Reduction | MMV Log Reduction |
| --- | --- | --- |
| Blue Sepharose | not tested | not tested |
| Copper Chelating (+ low pH hold) | ≧3.51 ± 0.52 | ≧2.71 ± 0.52 |
| Phenyl Sepharose | ≧3.54 ± 0.36 | ≧1.72 ± 0.64 |
| DNA Filtration | not tested | not tested |
| Viral Filtration | ≧5.51 ± 0.43 | ≧4.76 ± 0.00 |
| Total log Reduction | ≧12.56 | ≧9.19 |

In-Process Testing

Figure 3:
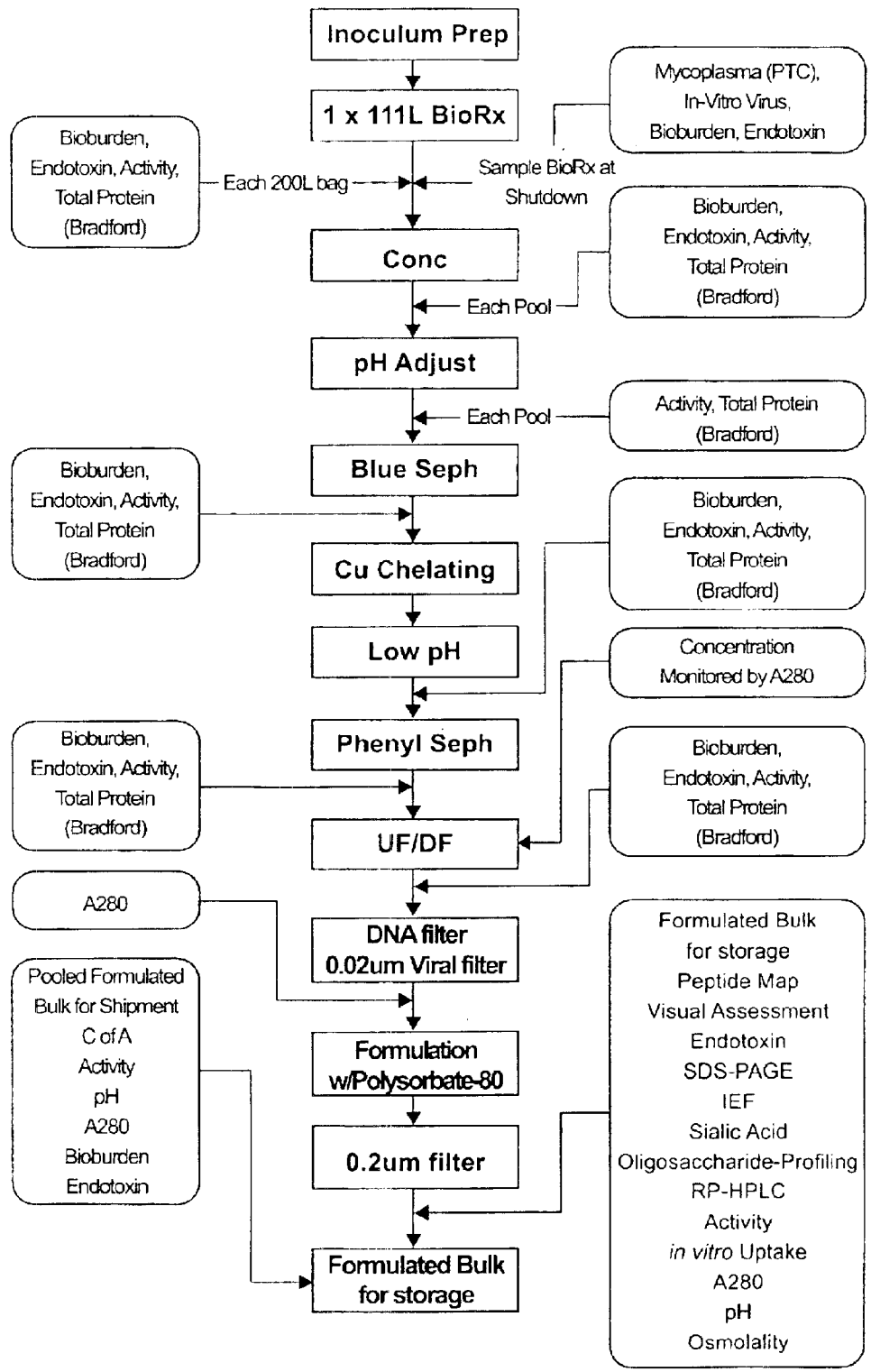
FIG. 3 provides the flow diagram of the method for purifying a human N-acetylgalactosamine-4-sulfatase (ASB) according to the perfusion process method (Tables 14 and 15).

In-process testing is performed throughout the process and is illustrated in FIG. 3. In-process testing of the harvest cell culture fluid and the purification intermediates is described in Tables 19 and 20.

TABLE 19

In-Process Testing of the Harvested Cell Culture Fluid

| Test | Action Levels |
| --- | --- |
| Bacterial Endotoxin by LAL (USP/EP) | ≧2 EU/mL |
| Bioburden (USP/EP) | ≧1 cfu/10 mL |
| Total Protein by Bradford and Activity | Results used for the calculation of the Blue Sepharose column load |
| Mycoplasma[1] | Negative (Release Specification) |
| In vitro Assay For The Presence of Viral Contaminants[1] | Negative (Release Specification) |

[1]Sampling is performed at multiple time points during the cell culture harvest stage of manufacturing. The last sample removed prior to the termination of the cell culture process is tested and a negative result is required for lot release.

TABLE 20

In-Process Testing of Purification Intermediates

| Test | Action Levels |
| --- | --- |
| Bacterial Endotoxin by LAL (USP/EP) | ≧3 EU/mL in column eluates[1] |

TABLE 20-continued

In-Process Testing of Purification Intermediates

| Test | Action Levels |
| --- | --- |
| Bioburden (USP/EP) | ≧20 cfu/mL pre-filtration[1] |
| | ≧1 cfu/100 mL in Formulated Bulk Drug Substance (FBDS)[2] |
| Activity | Result used for the calculation of the Copper Chelating and Phenyl Sepharose column loads |
| Total Protein by UV-Vis Spectrophotometry | Result used for the calculation of the protein concentration for the UF/DF |

[1]Results exceeding action levels are investigated per standard operating procedures.
[2]If results exceed action level, the FBDS will be 0.2 μm filtered into appropriate sterile storage containers and then quarantined pending release for shipment to filling sites.

Results of Perfusion Method of Purifying Precursor rhASB

Table 21 provides data on the degree of purity of rhASB obtained using the purification methods described in Tables 15 and 16. The "Purity by RP-HPLC" column indicates the degree of purity obtained for the combined amount of both the precursor and mature forms of rhASB.

TABLE 21 rhASB Lot Release Results

| Lot | Purity by RP-HPLC | Presence of the processed forms* | Manufacturing process |
| --- | --- | --- | --- |
| AP60028 | 99.6 | − | Batch process |
| AP60029 | 98.8 | + | Batch process |
| AP60030 | 98.7 | + | Batch process |
| AP60031 | 99.1 | − | Batch process |
| AP60032 | 99.8 | − | Batch process |
| AP60033 | 99.4 | − | Batch process |
| AP60035 | 98.7 | − | Batch process |
| AP60036 | 99.4 | − | Batch process |
| AP60038 | 99.6 | − | Batch process |
| AP60039 | 99.3 | − | Batch process |
| AP60040 | 99.1 | − | Batch process |
| AP60101 | 99.3 | − | Batch process |
| AP60102 | 98.9 | − | Batch process |
| AP60103 | 99.0 | − | Batch process |
| AP60104 | 99.0 | + | Batch process |
| AP60105 | 99.0 | − | Batch process |
| AP60106 | 99.2 | − | Batch process |
| AP60107 | 99.4 | − | Batch process |
| AP60108 | 99.7 | − | Perfusion process |
| AP60109 | 99.8 | − | Perfusion process |
| AP60201 | 99.0 | N/A | Perfusion process |
| AP60202 | 100 | − | Perfusion process |

* "+" indicates the presence of the processed forms (estimated at 1–15%) in the formulated bulk drug substance; "−" indicates the absence of the processed forms.

Figure 4A:
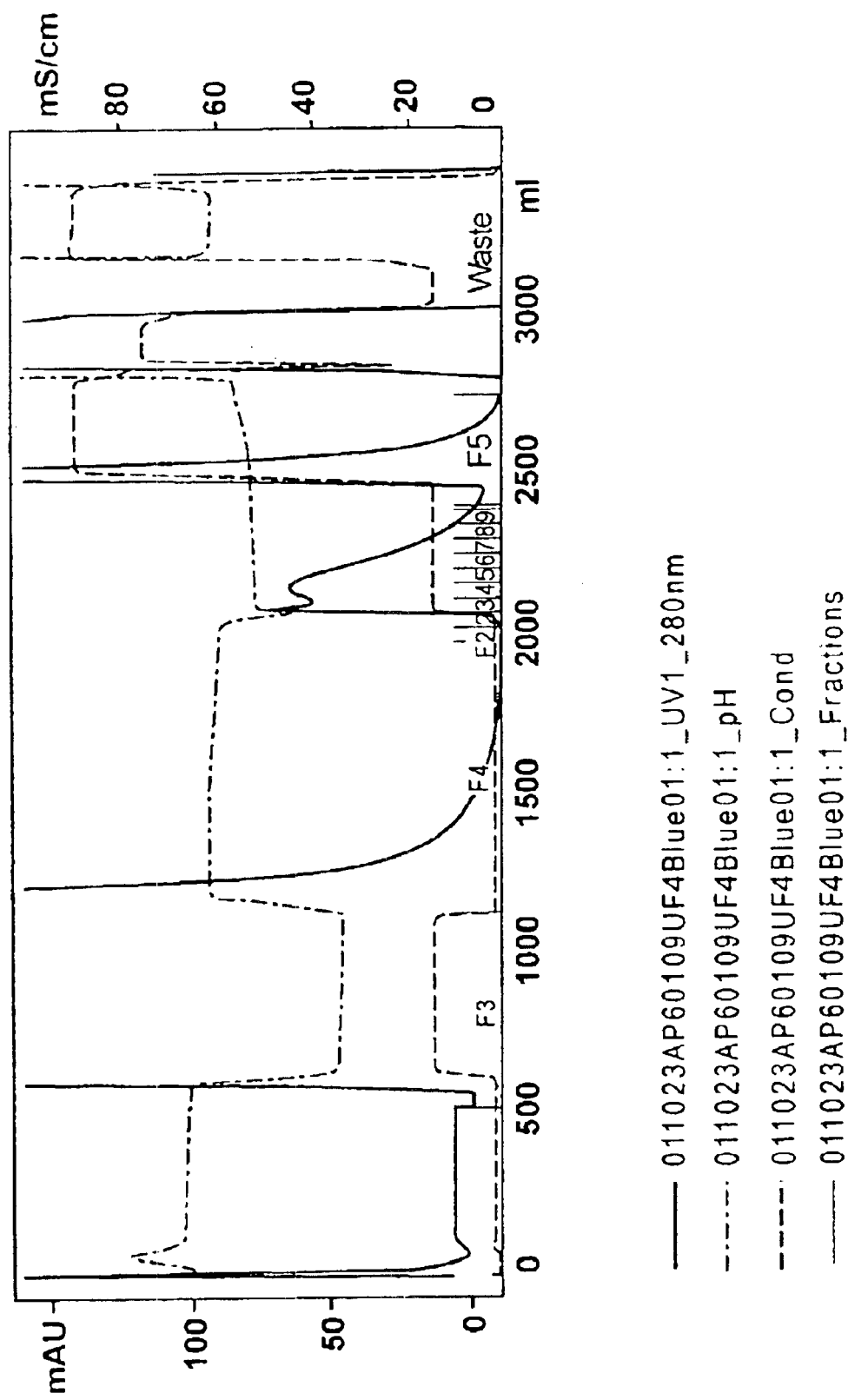
FIGS. 4A–4C depicts results obtained for the chromatograms of the Blue Sepharose Column (FIG. 4A), Copper Chelating Sepharose Column (FIG. 4B) and Phenyl Sepharose Column (FIG. 4C).
Figure 4B:
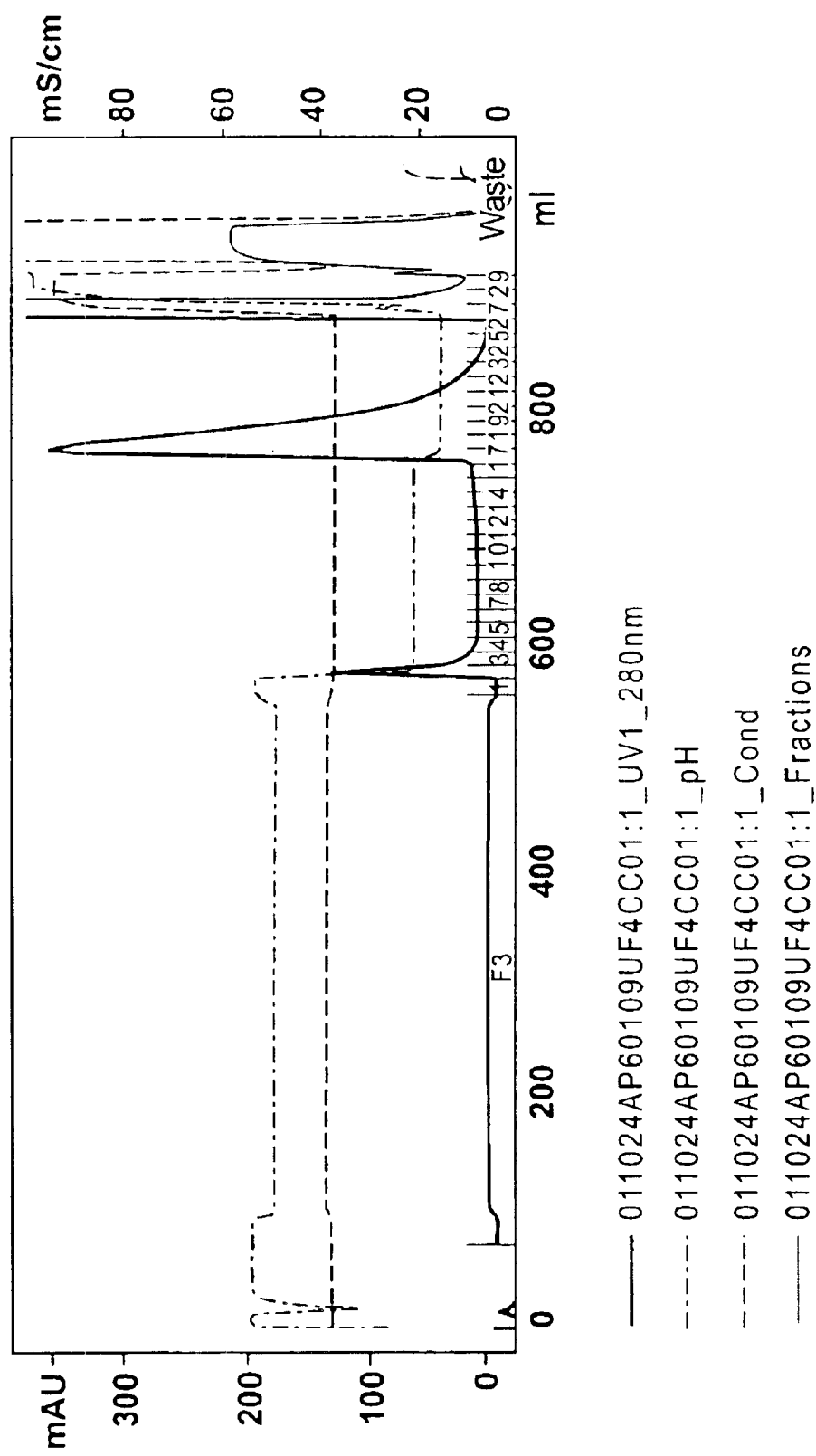
Figure 4C:
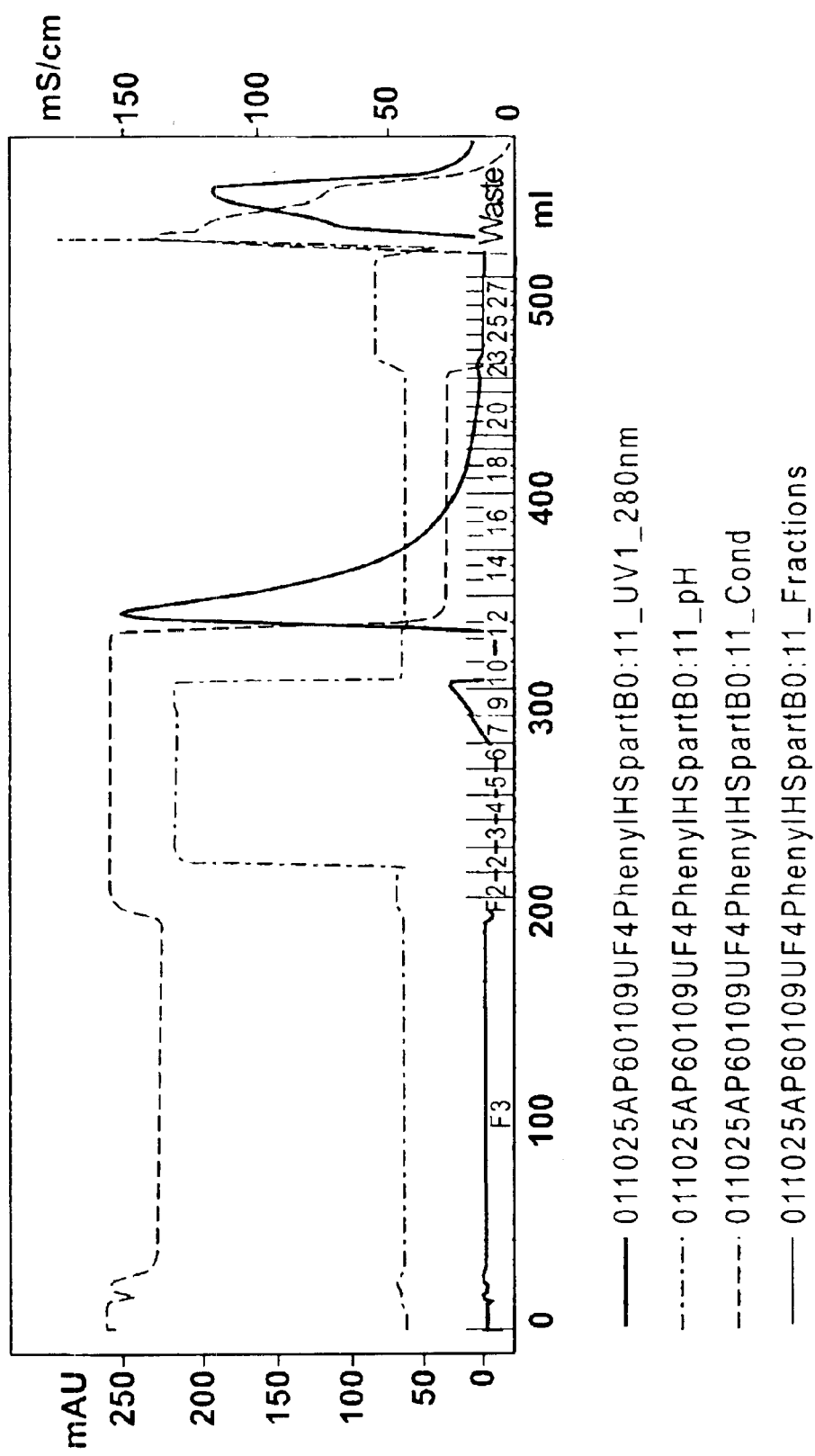
Figure 5:
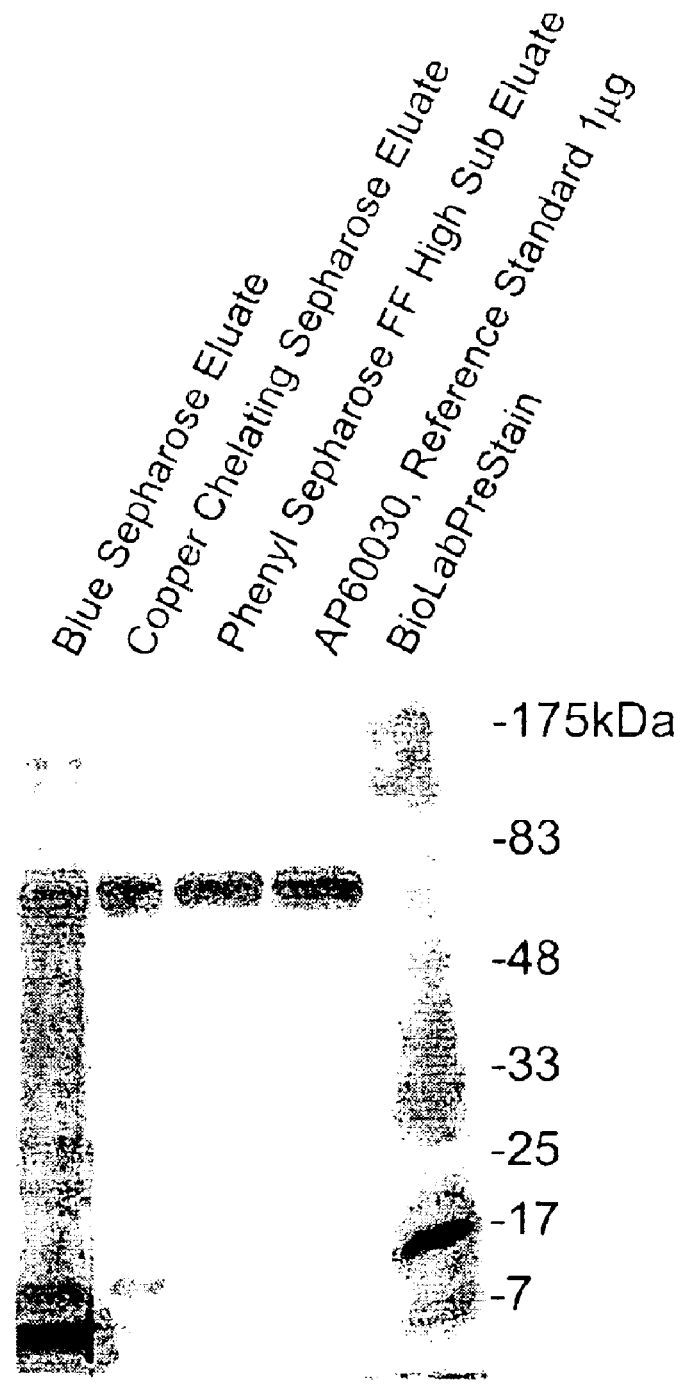
FIG. 5 depicts a 4–20% polyacrylamide gradient gel showing the result of a silver-stained SDS-PAGE of the perfusion process purification method (Tables 14 and 15).

FIGS. 4A–4C provide the representative chromatograms of the three chromatographic steps of the perfusion method of purification (Table 16). Table 22 provides the average recoveries of precursor rhASB for each of these three chromatographic steps. FIG. 5 provides the data for the purity analysis of in-process samples at each chromatographic step and of the purified final product (precursor rhASB).

TABLE 22

Summary of Purification Recoveries.

| Step | Average Recovery (%) |
| --- | --- |
| pH Adjustment to 5.0 | 83 |
| Blue Sepharose Column | 84 |
| Copper Chelating Sepharose Column | 86 |
| Copper to Phenyl Transition | 86 |
| Phenyl Sepharose Column | 88 |
| Overall | 50 |

Figures 6A, 6B, 6C, 6D:
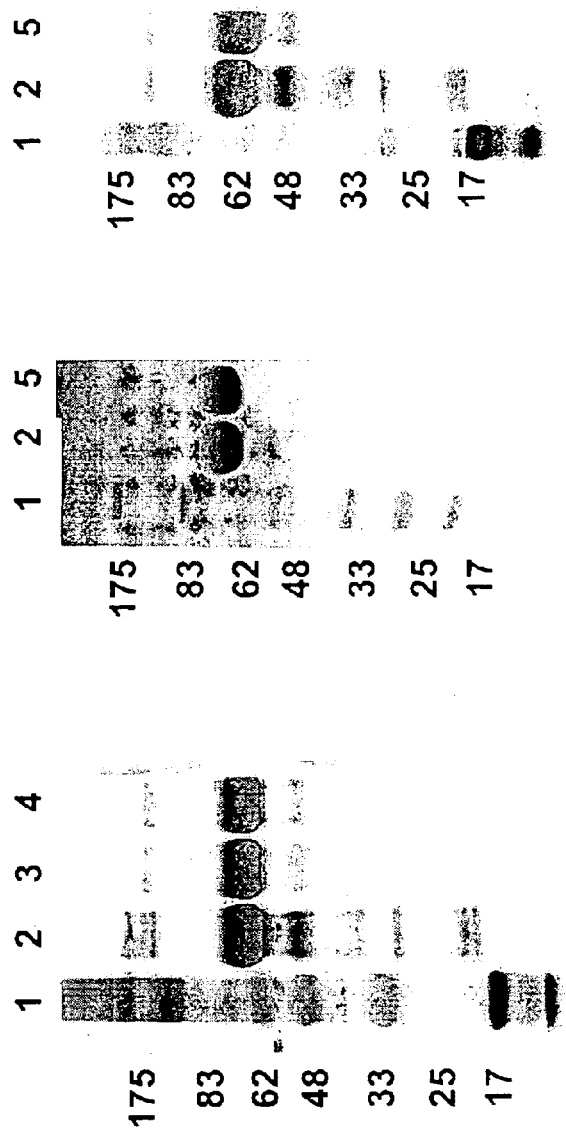
FIGS. 6A–6F depicts the results on 4–20% polyacrylamide gradient SDS gels of the following samples: lane 1, NEB broad range prestained molecule weight standards (MW in kDa); lane 2, 5 µg ASB from lot AS60001 (old batch process); lane 3, 5 µg ASB from lot AP60109 UF4 (perfusion process); lane 4, 5 µg ASB from lot AP60109 UF10 (perfusion process); lane 5, 5 µg ASB from lot AP60109 UF15 (perfusion process); lane 6, 5 µg ASB from lot AP60109 AUF18 (perfusion process); lane 7, 5 µg ASB from lot AP60109 AUF22 (perfusion process); lane 8, 5 µg ASB from lot AP60109 AUF25 (perfusion process); and, lane 9, 5 µg ASB from lot AP60109 AUF27 (perfusion process). The gels are stained either with Coomassie R-250 or silver-stained.
Figure 6F:
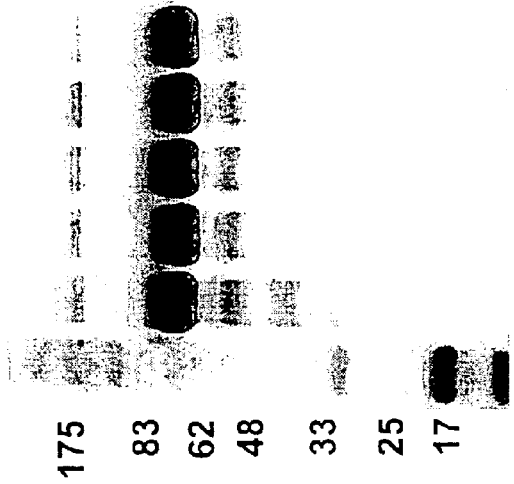
Figure 6E:
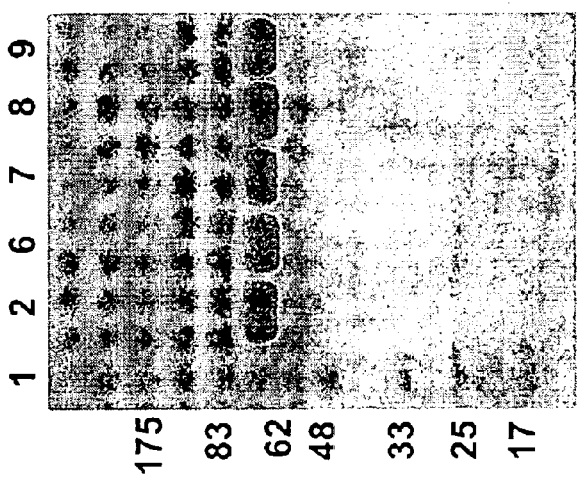
Figure 7A:
FIG. 7A depicts the results on silver-stained 4–20% polyacrylamide gradient SDS gels.
Figure 7B:
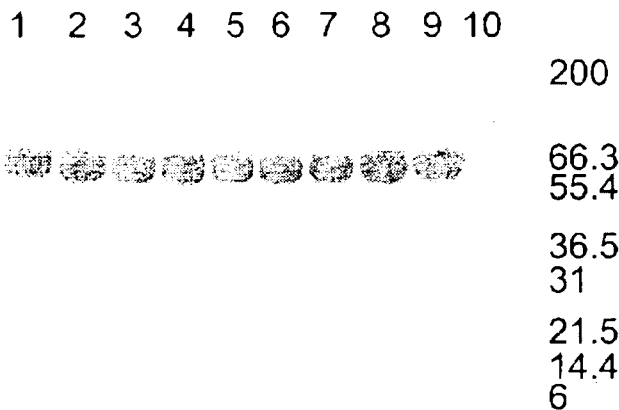
FIG. 7B depicts the results on Coomassie stained 4–20% polyacrylamide gradient SDS gels. Lane 1, lot AP60202 LF4; lane 2, lot AP60202 UF10; lane 3, lot AP60202 UF18; lane 4, lot AP60202 (BMK); lane 5, lot 102PDO0139× B3; lane 6, lot 102PD0139× B5; lane 7, perfusion reference standard rhASB-202-002; lane 8, lot 102PD0139 P1; lane 9, lot 102PD0139 P2; and, lane 10, Mark 12 standard (MW in kDa).

When purified products obtained using the batch process and the perfusion process are compared, the perfusion process clearly produces a purer precursor rhASB. Even attempts to further optimize the batch processes by selecting different wash fractions or varying the conditions did not result in the consistently pure product obtainable by the perfusion process. The perfusion process is able to produce consistent precursor rhASB purity of 99% or more, while the batch process does not (Table 21). FIG. 6 provides a comparison between the products obtained using the old batch method wherein the cell culture is cultured using a medium that is supplemented with G418 and not supplemented with folic acid, serine and asparagine (lane 2), and the purified products purified using the perfusion process (lanes 3–9)). The samples of rhASB were denatured in SDS with a reducing agent and subjected to electrophoresis through 4–20% PAGE in SDS running buffer. The batch process purified products clearly contain far more impurities (especially near the 48 kDa size) than the perfusion process purified products. The batch process rhASB appear to detectable amounts of processed forms (estimated at 1–15%) (lane 2). The perfusion process purified lots are highly comparable to each other and are significantly less complex than the batch process purified rhASB standard, indicating a higher degree of purity for the perfusion process material.

Table 23 provides percent purity of precursor rhASB purified using the perfusion process purification method.

TABLE 23

Purity of Final Product.

| Lot | Purity by RP-HPLC (% main peak) |
| --- | --- |
| AC60109 UF #4 | 99.8 |
| AC60109 UF #10 | 99.6 |
| AC60109 UF #1 | 99.7 |
| AC60109 UF #18 | 99.9 |
| AC60109A UF #22 | 99.7 |
| AC60109A UF #25 | 99.8 |
| AC60109A UF #27 | 100 |
| AC60109 BMK Manufacturing | 99.8 |
| AC60202 UF #4 | ND |
| AC60202 UF #10 | ND |
| AC60202 UF #18 | ND |
| AC60202 BMK Manufacturing | 100 |
| Average | 99.8 |

ND = not determined.

Table 24 provides percent purity of lots of precursor rhASB purified using the perfusion process purification method, where purity has been evaluated by RP-HPLC and SEC-HPLC (which allows quantification of impurities of different molecular weights such as processed forms or multimers).

TABLE 24

Purity by RP-HPLC and SEC-HPLC

| Lot | Purity by RP-HPLC (% Main Peak) | Purity by SEC-HPLC (% Main Peak) |
| --- | --- | --- |
| AP60109 | 99.8 | 99.8 |
| AP60202 | 100 | >99 |
| AP60204 | 99.7 | 99.8 |
| AP60206 | 100 | 99.8 |
| AP60301 | 100 | 99.6 |
| AP60302 | 100 | 99.6 |
| AP60303 | 100 | 99.5 |
| AP60304 | 100 | ND* |
| Average | 99.9 | 99.6 |

*Not Determined

Protease Removal in the Perfusion Process

At the 180 L batch scale two relatively large 24 L DEAE Sepharose runs are required per lot. The perfusion process generates 10-fold larger harvest volumes that impose severe impractical DEAE Sepharose column sizes and buffer volumes for practical large scale purification. Therefore, elimination of the particularly untenable DEAE Sepharose step was evaluated in an effort to streamline the new perfusion purification train. As a consequence, the three column train (as described in Table 16) overcomes this large scale production obstacle.

Figure 8A:
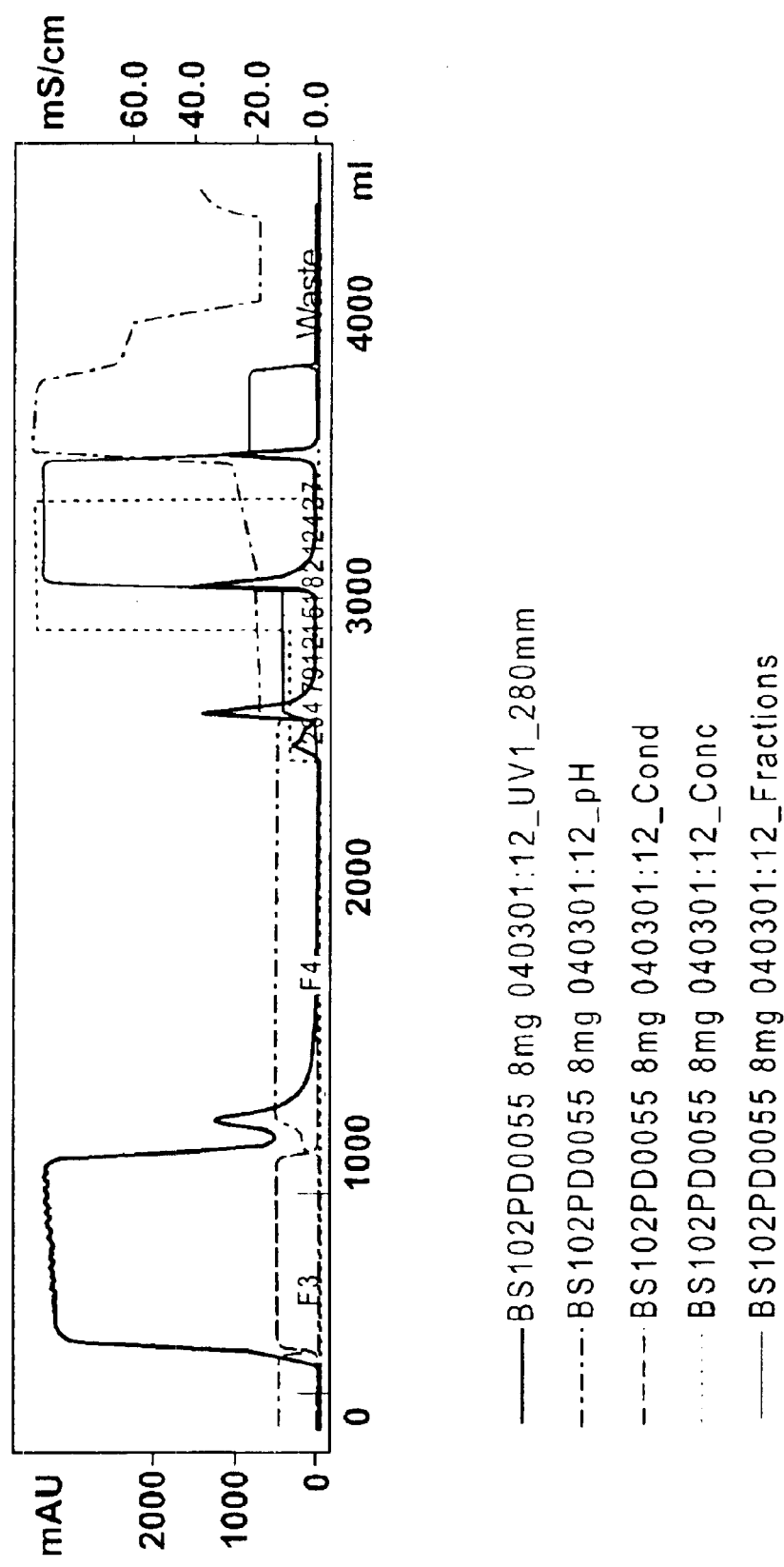
Figure 8B:
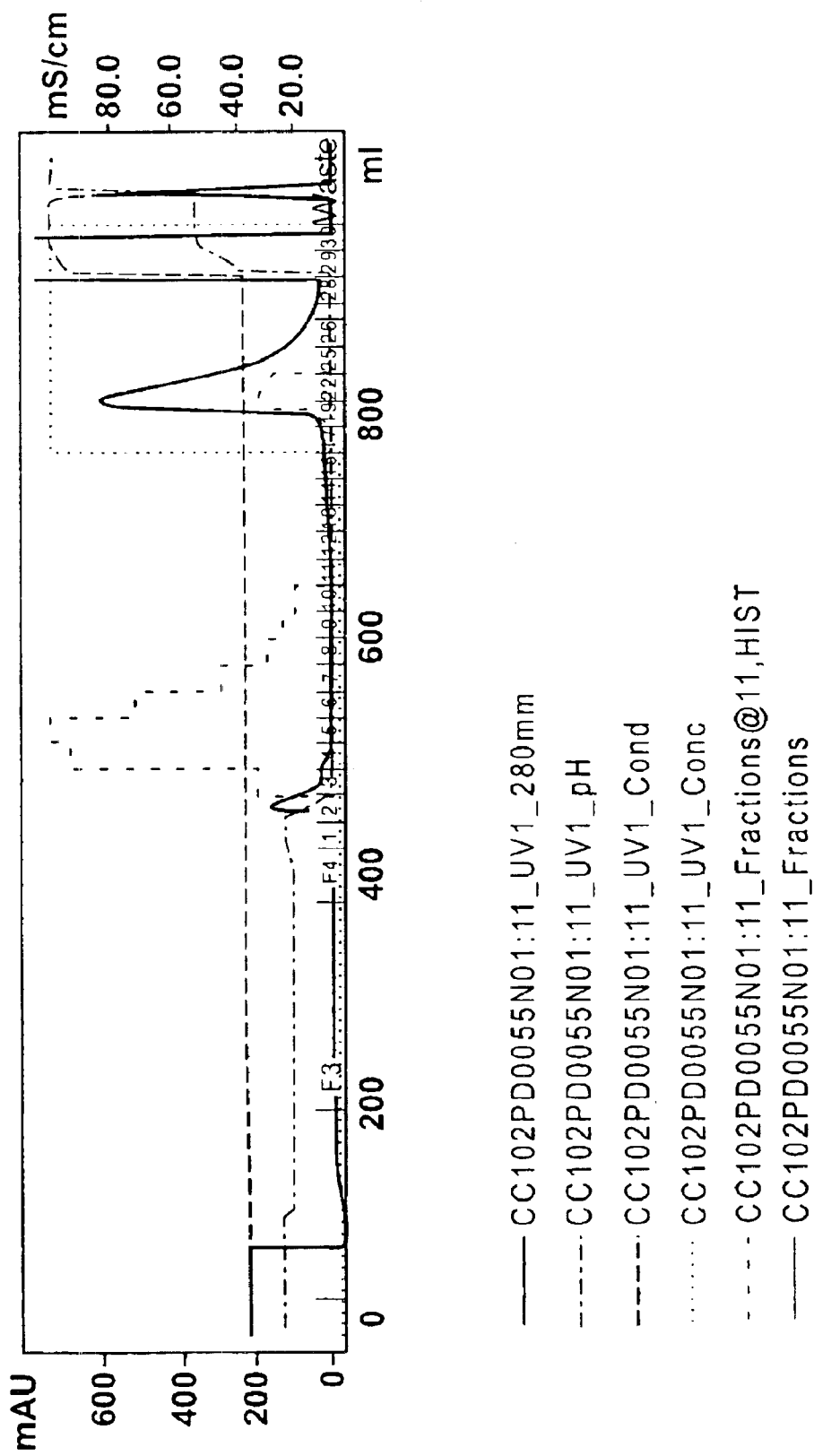

The DEAE Sepharose chromatography step in the batch process (described in Table 15) was employed primarily to remove total protein (including proteases) and the pH indicator dye, Phenol Red. The latter issue is addressed in the new process by removal of Phenol Red from the 302 media formulation. The removal of total protein by DEAE sepharose step resulted in higher Blue sepharose capacity at pH 5.5. In the new process, Blue Sepharose conditions needed to be identified that balanced high rhASB capacity while limiting protease activity. Both capacity and proteolysis are enhanced at low pH. In addition, clearance of proteases should be demonstrable to improve the robustness of the subsequent Copper Chromatography step, where clearance of the protease, cathepsin, has been found problematic in the Batch process. Conditions were found which yielded the desired results, whereby, loading was performed at low pH, while wash and elution conditions were at higher pH, conditions that efficiently clear the protease, cathepsin, with an acceptable load of 0.8 mg rhASB/ml resin. Removal of the protease activity (e.g. cathepsin) is demonstrated in the chromatograms of FIG. 8.

Figure 9B:
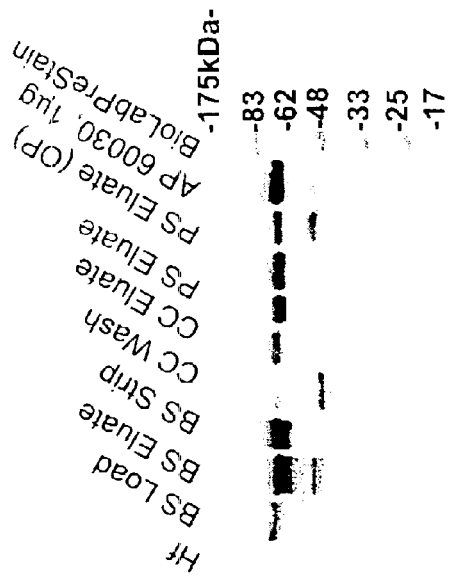
FIG. 9B depicts the results of the proteins transferred from the gel of FIG. 9A transferred onto nitrocellulose and probed by anti-rhASB antibodies.
Figure 9A:
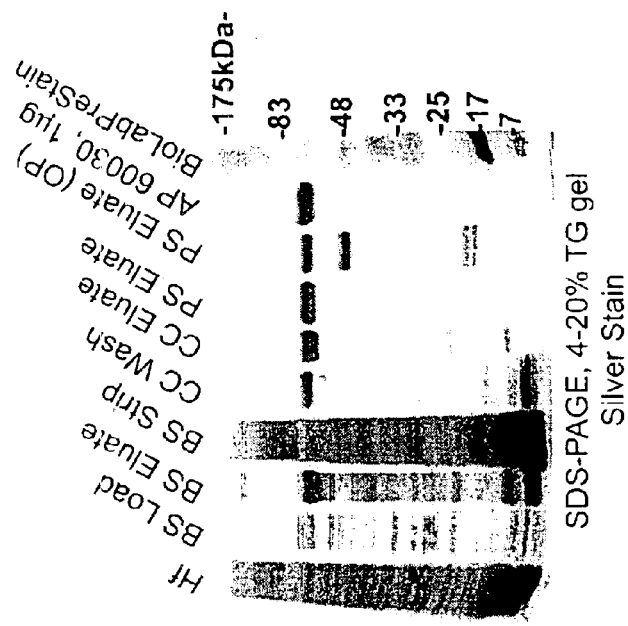
FIG. 9A depicts the results of a silver-stained 4–20% polyacrylamide gradient SDS gels.
Figure 9C:
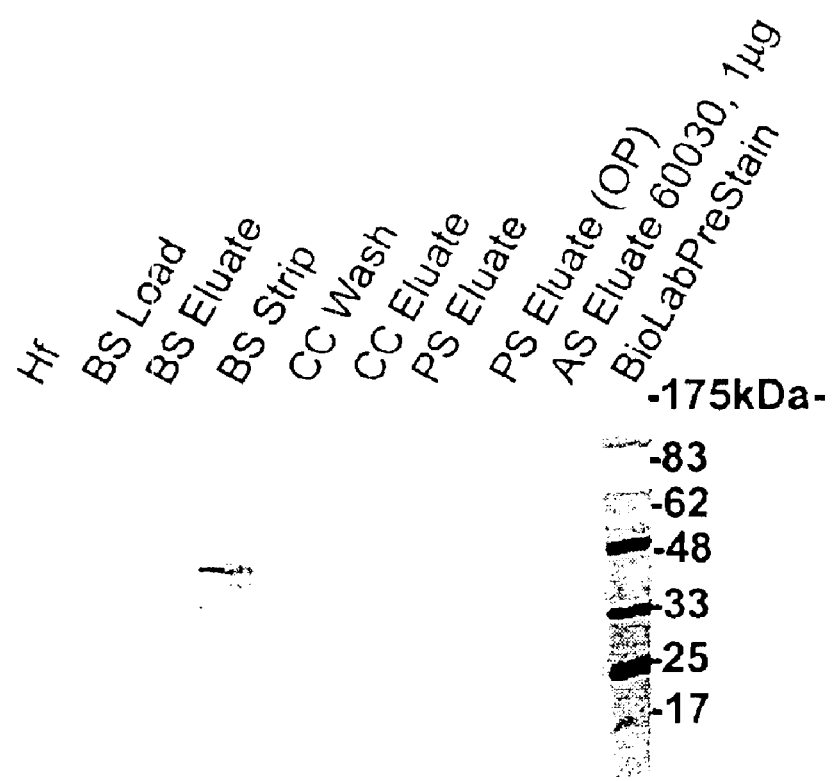
FIG. 9C depicts the results of the proteins transferred from the gel of FIG. 9A transferred onto nitrocellulose and probed by anti-cathepsin antibodies. BioLab-PreStain indicates molecular weight standards (MW in kDa).

Comparison of rhASB purified from perfusion run, 102PD0055, using either the new process (without DEAE FT chromatography) or old Batch purification process (PS Eluate (OP) indicate that the old process material purified (using the batch method) from the same reactor run, lane PS Eluate (OP), has significant more proteolysis, as demonstrated by the additional bands on silver-stained gel and detectible by anti-ASB antibodies (see FIG. 9). The new process is much purer relative to the batch standard. The cathepsin protease is cleared by Blue-chromatography. Anti-cathepsin cross-reactive material is seen in the Blue Strip fraction using the new process.

The pharmacokinetic results described below in Example 11 show that the purer rhASB preparation results in a longer half-life than the previous batch standard.

EXAMPLE 10

Surfactant Effects on Particle Formation

An experimental protocol was carried out to determine the effect of Polysorbate-80 on particle generation in vials of rhASB made with the new perfusion cell culture process. Visual and particle count assays were employed to determine the extent of particle generation. In addition, activity testing, polyacrylamide gel electrophoresis (PAGE), immunoblotting and size exclusion chromatography (SEC) were performed to confirm product quality in the presence of Polysorbate-80 and/or shaking relative to untreated controls. Vials and stoppers used for the rhASB batch process (Old, Wheaton 5 ml, 2905-B24B/West S-127 (4401/45)) were also compared to the proposed vials and stoppers to be used for the perfusion-derived material (New, Wheaton 5 ml, 2905-B8BA/West S-127 (4432/50)).

Vials were filled after rhASB had been passed through a 0.2 μm filter using a 10 ml disposable pipette. Two vials were filled for each rhASB-containing test. Both were used for the visual assay with one dedicated for particle counting and the other saved for the remainder of assays. Only one buffer control vial/test was filled. Few particles were introduced due to set-up, sample handling, filtration or filling. From visual and particle count analysis (results shown in Tables 25A–C and 26A–C below), on days 0, 1 and 14 days, no significant particulate formation was detected in unshaken vials of formulated drug relative to buffer-only controls.

After 18 hr of shaking at 4 degrees C., a large increase in particles was observed in both vial configurations with rhASB in formulation buffer alone (10 mM sodium phosphate, 150 mM sodium chloride, pH 5.8), without polysorbate. Fine flakes were clearly visible.

The particle counting was done using the HIAC/ROYCO Model 9703 Particle Counter. The liquid particle counter is capable of sizing and counting particles ranging from 2.0 μm to 150 μm. Three aliquots of not less than 5 mL each are put into the light obscuration sensor. The average particle counts from runs 2 and 3 are reported as particle counts per mL. Based on HIAC-Royko quantification of particles 10 μm in size, 2069 and 1190 particles/mL were counted in old and new vials configurations, respectively. In the presence of 0.001% Polysorbate-80, a markedly lower count was found with 21 and 49 particles/ml. At 0.005% Polysorbate-80, essentially no difference between shaken and unshaken vials could be detected.

In old vials/seals without Polysorbate-80, there was an unexpected drop in particle counts/ml from 2069 to 268 from days 1 to 14 days after shaking. The visual assay indicated larger flakes in the same 14 day vials in which lower counts were found; it is possible that the larger particles interfered with the HIAC-Royko assay, or that the old vial configuration contributes to increased particle formation with eventual coalescence and aggregation into larger, albeit fewer, particles.

Additional testing was done to confirm the integrity of the protein after shaking. Specific activity was unchanged. Size Exclusion Chromatography, a method that can detect changes in protein aggregation, which might be influenced by mechanical agitation, showed no increase in larger molecular weight species. In order to detect breakdown products, SDS-PAGE gels of rhASB were either silver stained or transferred onto nitrocellulose and blotted with Anti-rhASB antibody. No additional bands were detected in any of the samples.

TABLE 25A

Visual Assay, Day 0

| Vial | [Polysorbate-80] % | 102PD0089-01 No Shake | Buffer No Shake |
|---|---|---|---|
| Old | 0 | (−) (−) | (−) |
| Old | 0.005 | (−) (−) | (−) |
| Old | 0.001 | (−) (−) | (−) |
| New | 0 | (−) (−) | (−) |
| New | 0.005 | (−) (−) | (−) |
| New | 0.001 | (−) (−) | (−) |

TABLE 25B

Visual Assay, Day 1

| Vial | [Polysorbate-80] % | 102PD0089-08 Shake | No Shake | | Buffer Shake | No Shake |
|---|---|---|---|---|---|---|
| Old | 0 | (++) | (++) | (−) (−) | (−) | (−) |
| Old | 0.005 | (−) | (−) | (−) (−) | (−) | (−) |
| Old | 0.001 | (+/−) | (−) | (−) (−) | (−) | (−) |
| New | 0 | (++) | (++) | (+/−) (−) | (−) | (−) |
| New | 0.005 | (−) | (−) | (−) (−) | (−) | (−) |
| New | 0.001 | (+/−) | (−) | (+/−) (−) | (−) | (−) |

TABLE 25C

Visual Assay, Day 14

| Vial | [Polysorbate-80] % | 102PD0089-01 Shake | No Shake | | Buffer Shake | No Shake |
|---|---|---|---|---|---|---|
| Old | 0 | (+++) | (+++) | (−) (−) | (−) | (−) |
| Old | 0.005 | (−) | (−) | (−) (−) | (−) | (−) |
| Old | 0.001 | (+/−) | (+) | (−) (−) | (−) | (−) |
| New | 0 | (++) | (++) | (+/−) (−) | (−) | (−) |
| New | 0.005 | (−) | (−) | (−) (−) | (−) | (−) |
| New | 0.001 | (+/−) | (−) | (+/−) (−) | (−) | (−) |

Visual Assay:
No visible precipitation −
Borderline, uncertain about observation −/+
Small amount of fine precipitate +
Significant precipitation, cloudy ++
Very cloudy, large flakes of precipitate +++

TABLE 26A

Particulate Analysis, HIAC-Royko (Particles/mL), Day 0

| | | 102PD0089-01 No Shake | | Buffer No Shake | |
|---|---|---|---|---|---|
| Vial | [Polysorbate-80] % | 10 μm | 25 μm | 10 μm | 25 μm |
| Old | 0 | 4.5 | 0.5 | 2.5 | 0.0 |
| Old | 0.005 | 2.0 | 0.5 | 1.5 | 0.0 |
| Old | 0.001 | 4.5 | 1.5 | 2.5 | 1.0 |
| New | 0 | 6.5 | 2.5 | 6.0 | 4.0 |
| New | 0.005 | 1.5 | 0.5 | 3.0 | 1.0 |
| New | 0.001 | 19.5 | 5.0 | 2.0 | 0.0 |

TABLE 26B

Particulate Analysis, HIAC-Royko (Particles/mL). Day 1

| Vial | [Polysorbate-80] % | 102PD0089-01 | | | | Buffer | | | |
| --- | --- | --- | --- | --- | --- | --- | --- | --- | --- |
| | | Shake | | No Shake | | Shake | | No Shake | |
| | | 10 µm | 25 µm | 10 µm | 25 µm | 10 µm | 25 µm | 10 µm | 25 µm |
| Old | 0 | 2069.0 | 74.5 | 3.0 | 0.5 | 0.5 | 0.5 | 2.5 | 2.0 |
| Old | 0.005 | 3.5 | 0.0 | 2.0 | 0.5 | 3.5 | 2.5 | 1.0 | 0.5 |
| Old | 0.001 | 21.5 | 2.5 | 2.0 | 1.0 | 2.5 | 1.0 | 1.5 | 1.5 |
| New | 0 | 1190.0 | 34.5 | 5.0 | 0.5 | 0.0 | 0.5 | 2.5 | 3.5 |
| New | 0.005 | 19.0 | 0.0 | 4.5 | 0.0 | 2.5 | 0.0 | 17.0 | 0.0 |
| New | 0.001 | 49.0 | 0.5 | 9.0 | 2.5 | 9.5 | 0.5 | 6.0 | 1.0 |

TABLE 26C

Particulate Analysis, HIAC-Royko (Particles/mL). Day 14

| Vial | [Polysorbate-80] % | 102PD0089-01 | | | | Buffer | | | |
| --- | --- | --- | --- | --- | --- | --- | --- | --- | --- |
| | | Shake | | No Shake | | Shake | | No Shake | |
| | | 10 µm | 25 µm | 10 µm | 25 µm | 10 µm | 25 µm | 10 µm | 25 µm |
| Old | 0 | 268.0 | 18.0 | 0.5 | 0.0 | 4.5 | 2.0 | 0.0 | 0.5 |
| Old | 0.005 | 2.0 | 2.5 | 1.0 | 1.0 | 2.5 | 0.5 | 6.0 | 3.0 |
| Old | 0.001 | 72.0 | 6.5 | 7.0 | 3.0 | 7.0 | 1.0 | 1.0 | 2.0 |
| New | 0 | 1335.0 | 29.0 | 2.0 | 0.0 | 1.5 | 0.0 | 1.5 | 0.5 |
| New | 0.005 | 7.0 | 0.5 | 16.0 | 0.0 | 13.5 | 0.0 | 13.0 | 2.0 |
| New | 0.001 | 38.0 | 1.5 | 5.5 | 0.5 | 16.0 | 0.5 | 8.0 | 0.0 |

The results indicated that the manual fill procedure generates very few particles regardless of formulation. After constant and vigorous shaking at 180 rpm, particles were clearly visible in vials containing rhASB formulated without Polysorbate-80.

The presence of Polysorbate-80 was highly effective in inhibiting mechanically-induced particle formation. Protection was dramatic, with particle counts kept down to essentially background levels in shaken vials at 0.001% and 0.005% Polysorbate-80. The 0.005% Polysorbate-80 concentration shows slight improvement in reducing particle counts over the 0.001% Polysorbate-80 concentration.

Shaking or formulation was not observed to cause any product instability as evaluated by activity, protein concentration, purity or percent aggregation.

EXAMPLE 11

Clinical Study in Humans

A Phase ½, randomized, double-blinded clinical trial of recombinant human N-acetylgalactosamine-4-sulfatase (rhASB) in patients with mucopolysaccharidosis VI (MPS VI), Maroteaux-Lamy Syndrome, was conducted using drug product produced according to the batch process described herein. The rhASB was formulated at a concentration of 1 mg/mL, pH 5.8, 9 mM monobasic sodium phosphate 1 $H_2O$, 1 mM dibasic sodium phosphate 7 $H_2O$, 150 mM sodium chloride. When administered to patients, the rhASB was prepared by diluting the appropriate amount of drug solution in an intravenous (IV) bag with normal saline at room temperature. All patients were premedicated with an antihistamine prior to infusion to reduce the potential for infusion-associated reactions.

The objectives of this study were to evaluate the safety, efficacy and pharmacokinetic profile of two doses of rhASB as ERT in patients with MPS VI. Patients were randomized in a double-blind fashion to one of two dose groups, 0.2 and 1.0 mg/kg. Drug was given once per week as a four-hour IV infusion. Measures of safety included complete chemistry panel, urinalysis, complete blood count (CBC) with differential, and tracking of AEs. Immune response and infusion-associated reactions, complement activation and antibody formation are assessed for all patients. Efficacy parameters included exercise tolerance/endurance (6-minute walk test), respiratory capacity (pulmonary function tests), joint range of motion (JROM), functional status (Childhood Health Assessment Questionaire [CHAQ]), levels of urinary GAGs, and changes in hepatomegaly, visual acuity, cardiac function, and sleep apnea.

Pharmacokinetic evaluations were conducted during infusions at Weeks 1, 2, 12, 24 and periodically thereafter to measure antigen (enzyme) levels during and after infusion. Pharmacokinetic evaluations were also conducted at Weeks 83, 84 and 96 of the open-label extension of the study, when patients were switched commencing at Week 84 to the new perfusion-process purified rhASB in a formulation with 0.005% polysorbate80.

A total of seven patients was enrolled, and included patients with a range of characteristics consistent with rapidly advancing or moderately advancing disease. One patient dropped out of the study at Week 3 for personal reasons and was replaced. A pre-specified interim analysis was conducted following the completion of 24 weeks of treatment for the remaining six patients. Data from the Week 24 interim analysis showed that rhASB was well tolerated and the 1.0 mg/kg dose appeared to produce greater clinical benefit and to have a safety profile comparable to that of the 0.2 mg/kg dose.

Patients in the low-dose group were offered continued treatment at the 1.0 mg/kg dose level. Two patients initiated therapy at the higher dose level at intervals after Week 48 (Weeks 59 and 69). Patients treated through Week 96 have received the majority of planned rhASB infusions. No patient has missed more than two infusions total during this period.

Safety assessments performed during the initial 24, then 48 weeks of treatment showed that weekly treatment with rhASB at 0.2 or 1.0 mg/kg was well tolerated without significant differences between the two-dose groups. Longer term treatment (through Week 96) at 1.0 mg/kg weekly also was well tolerated.

Anti-rhASB Antibody Development and Complement Levels

Figure 10:
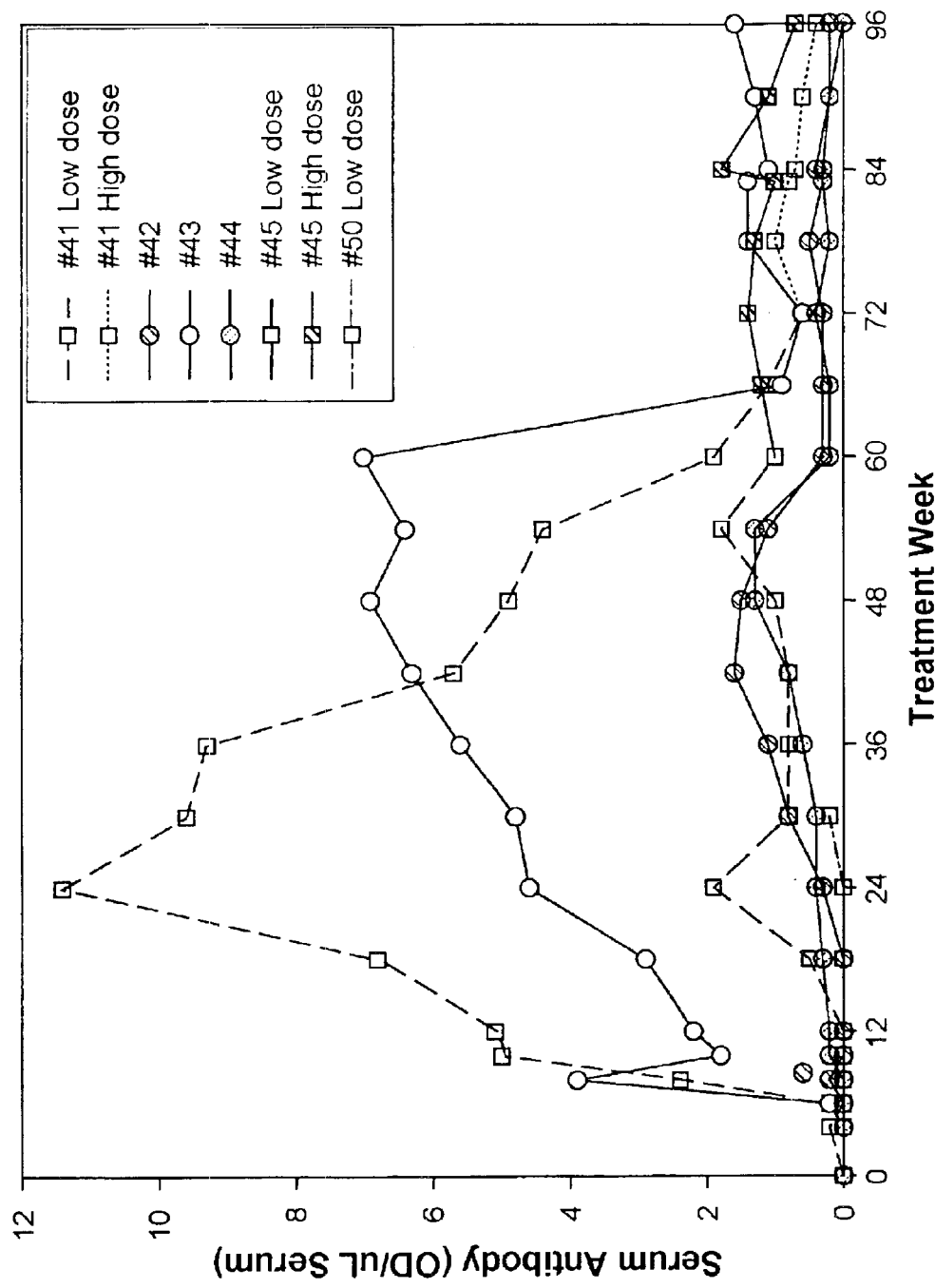
FIG. 10 shows serum anti-ASB antibody levels over 96 weeks of treatment with rhASB in a Phase 1/2 clinical study in humans.

All six patients on study drug at Week 30 had developed antibody to rhASB. Levels for four of the six patients remained relatively low and declined from peak levels by Week 60. Of the two patients that developed higher levels of antibody than the other four patients one patient's antibody levels declined from the peak level at Week 24, and the other patient's levels fell rapidly from the peak level at Week 60. No consistent changes in CH50, C3, or C4 complement levels have been observed during 96 weeks of treatment. Several patients have had modest intermittent declines in CH50 levels; however, no evidence of complement consumption of correlation between these low levels and infusion-associated symptoms were noted. FIG. 10 shows antibody levels over 96 weeks of treatment.

Urinary Glycosaminoglycans

Figure 11:
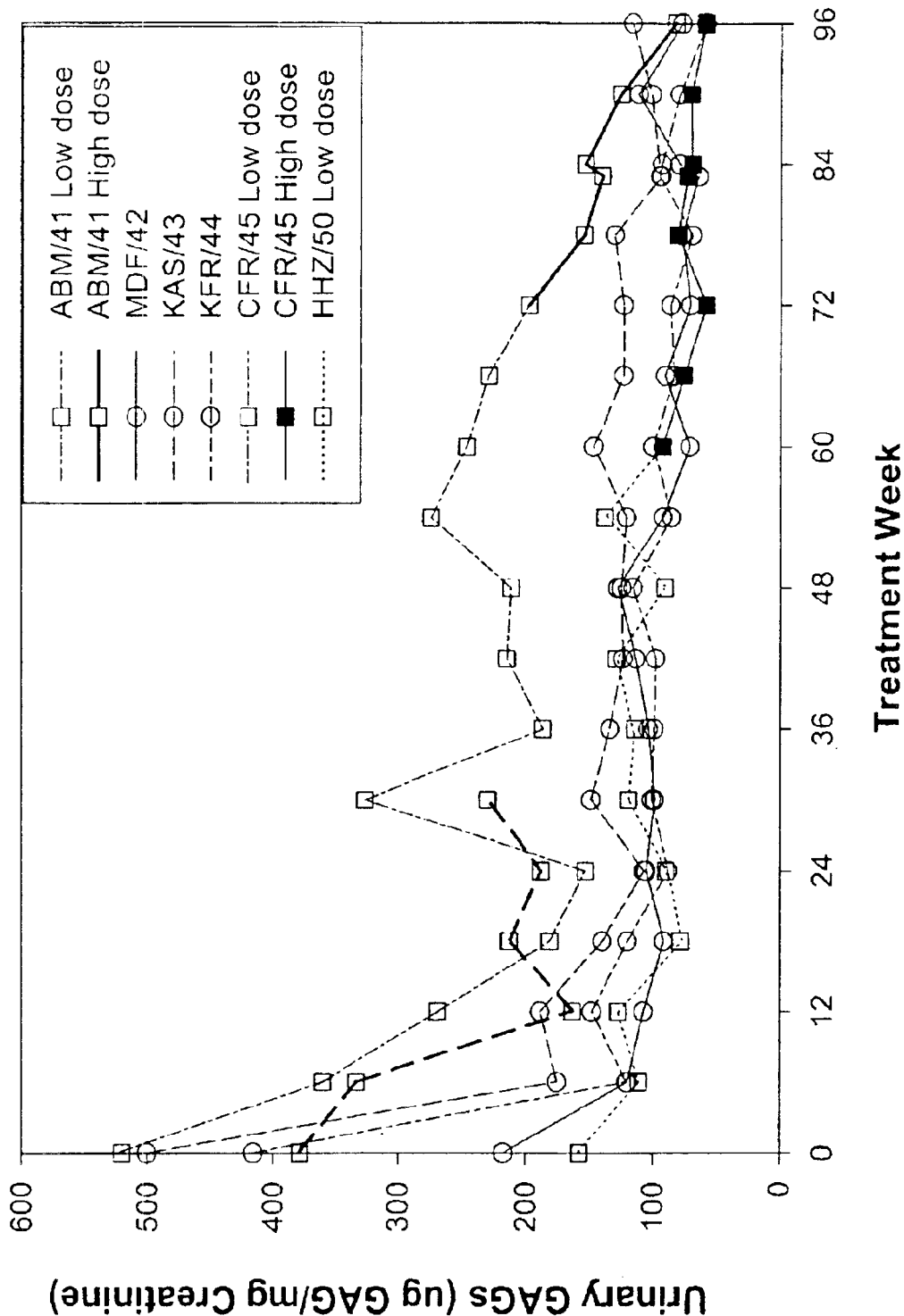
FIG. 11 shows the reduction in total urinary GAG levels over 96-weeks of treatment with rhASB in a Phase 1/2 clinical study in humans.
Figure 12:
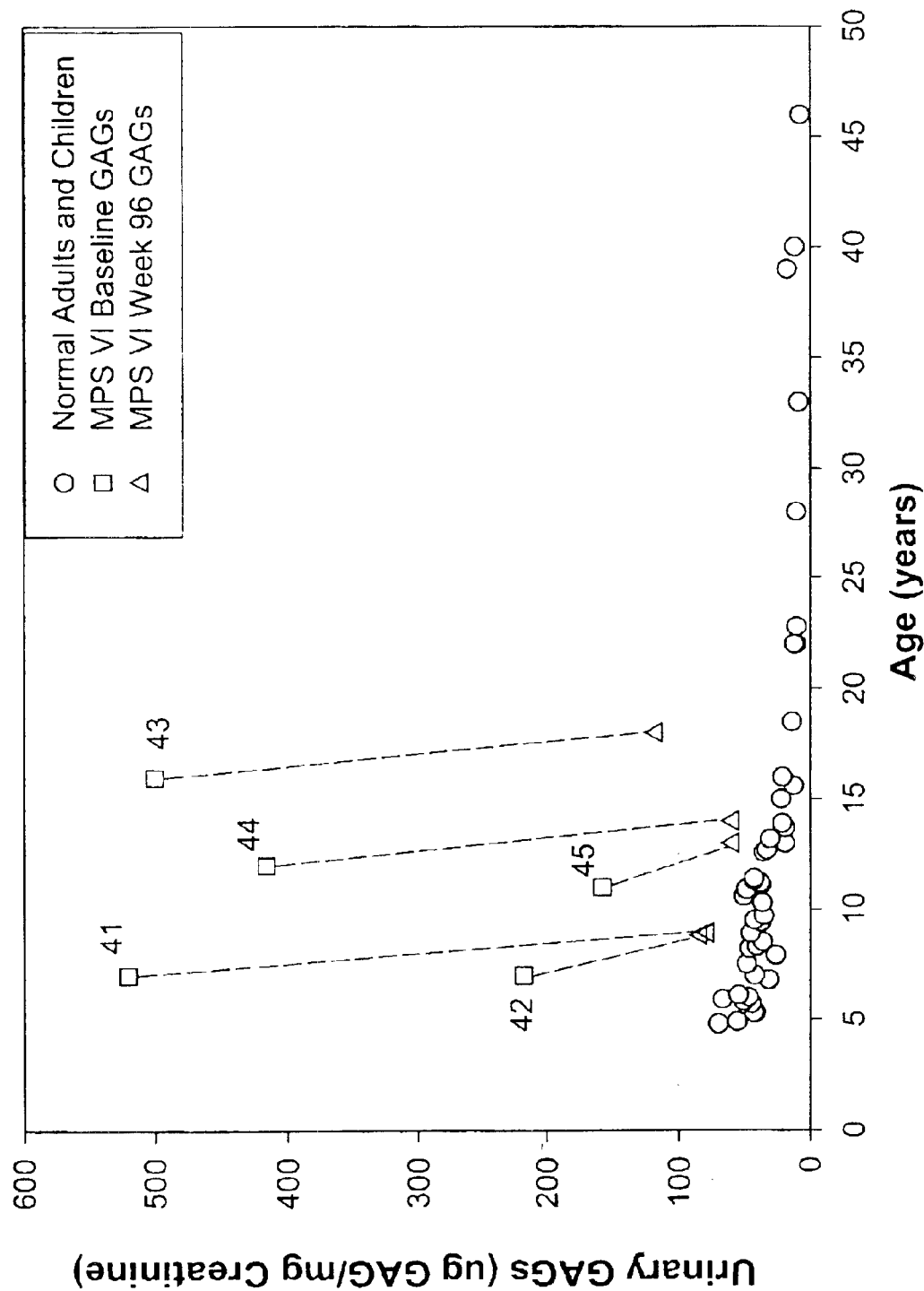
FIG. 12 shows a comparison of urinary GAG levels at week 96 in humans treated with rhASB to age-appropriate normal levels.

The level of urinary GAGs is a biochemical marker of the degree of lysosomal storage in MPS-affected individuals. By Week 24, urinary GAGs were reduced by an average of 70% in the high-dose group versus 55% in the low-dose group. The percentage of DS, the primary storage product of MPS VI, was similarly decreased by 44% and 18%, respectively. Examination of the time course of the change in urinary excretion of GAGs as a function of weeks on treatment showed a more pronounced drop in total urinary-GAGs by Week 6 in the high-dose group. These data confirm that the higher dose produced a larger change in both urinary GAGs and DS. Urinary GAGs have continued to decline through Week 96 for the patients in both treatment groups who remained in the study. FIG. 11 shows the reduction in total urinary GAG levels over the 96 weeks and FIG. 12 shows a comparison of levels at week 96 to age-appropriate normal levels. Note that the two patients in the 0.2 mg/kg dose group who remained in the study, Patients 41 and 45, rolled over to the 1.0 mg/kg dose on Weeks 69 and 59, respectively. At Week 96, these two patients had reductions in GAGs from screening of 85% and 63%. These were similar to reductions seen in the patients on 1.0 mg/kg through the entire 96 weeks. Patients 42, 43, and 44 had reductions of 64%, 77%, and 86% from screening, respectively. In both groups, the patients who had higher baseline GAG levels had higher percent reductions than patients with GAG levels that were closer to the normal range (<5 times upper limit of normal, i.e., mean plus 2 SD).

Endurance

Figure 13:
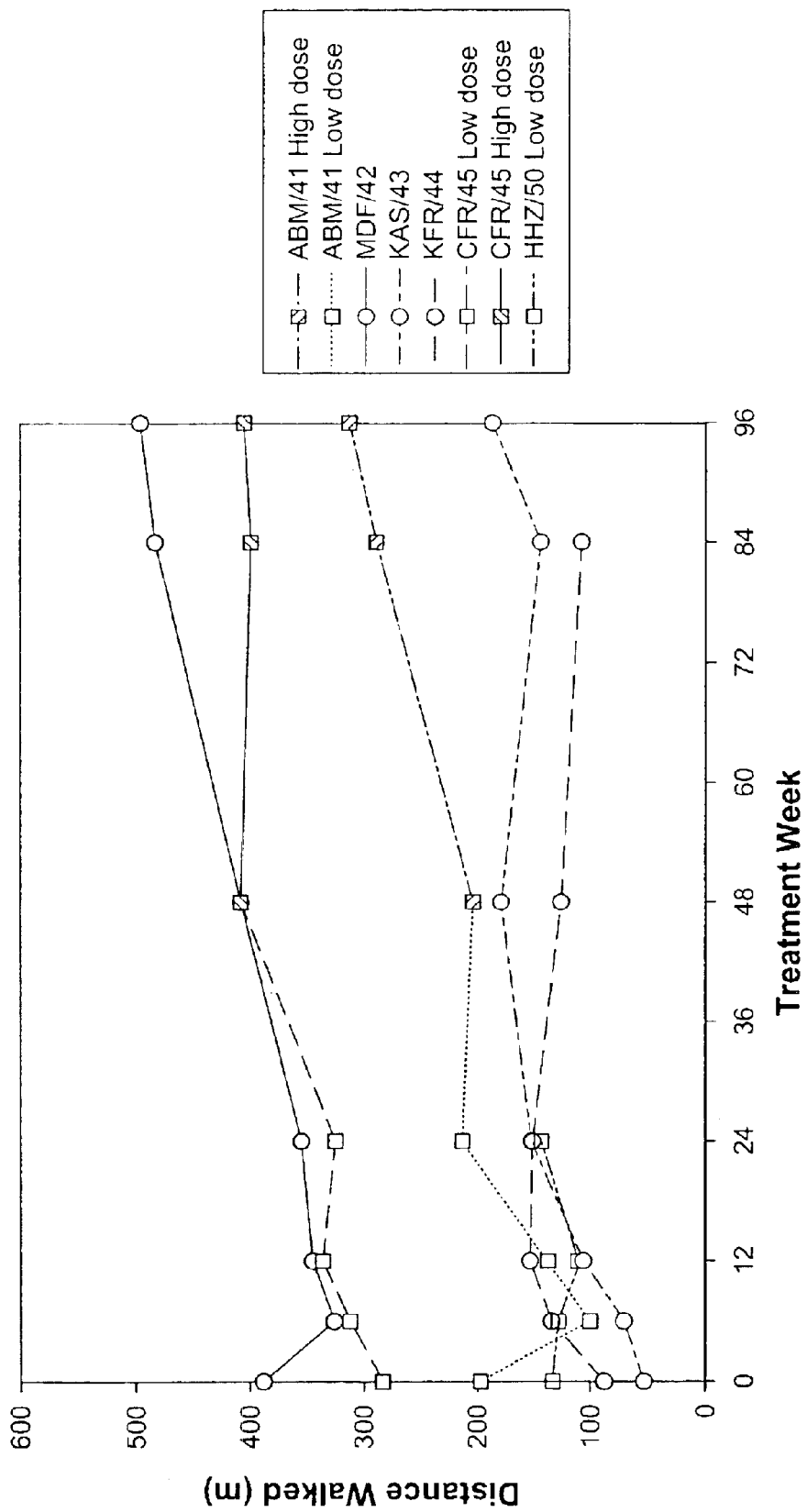
FIG. 13 shows the improvement in results of the 6-minute walk test over 96 weeks of treatment with rhASB in a Phase 1/2 clinical study in humans.

The 6-minute walk test served as the primary clinical measure of endurance. The two patients unable to walk >100 m at baseline, who were randomized to receive 1.0 mg/kg of study drug (#43 and #44), had large improvements in the total distance walked by Week 24. All patients except #44, who developed C1–C2 cord compression, showed improvement in their distance walked by Weeks 48 and 96. FIG. 13 shows the improvement in results of the 6-minute walk test over 96 weeks of treatment.

Additional Measures of Efficacy

Modest improvements in a number of other efficacy parameters were seen during the 96 weeks of study drug treatment. Shoulder ROM, particularly for flexion, improved in five of the six study patients at the Week 24 assessment. Three of the four patients (#41, 43 and 45) with assessments at Week 96 continued to show increases in shoulder flexion. Slight improvements were also seen in the measures of respiratory function, forced vital capacity (FVC) and forced expiratory volume for one second (FEV1), in three of four patients, at Week 96. Visual acuity, measurable in four out of six patients enrolled, improved by one or more lines in three of these four patients, although one patient had changes in his prescription lenses during this period. Hepatomegaly, measured by CT scan, although not a prominent feature of this disease, also declined modestly, particularly in those patients with larger livers at baseline.

Little change was seen in the remaining efficacy parameters, including cardiac function by ECG, grip and pinch strength, CHAQ questionnaire, height and weight, bone mineral density, and sleep'studies. No significant deterioration was observed in any of these parameters over the 96 weeks.

Pharmacokinetics

Pharmacokinetic evaluations were conducted during Weeks 1, 2, 12 and 24 of the double-blind study and during Weeks 83, 84 and 96 of the open-label extension. Beginning with Week 84, patients began to receive rhASB manufactured by the perfusion process described in Example 9.

Blood samples were collected during the infusion at 0, 15, 30, 60, 90 and 180 minutes, at the end of infusion at 240 minutes, and post-infusion at 5, 10, 15, 30, 45, 60, 90, 120 and 240 minutes. Pharmacokinetic parameters for rhASB were calculated using non-compartmental methods. Areas under the plasma concentration-time curve to infinity and first moment were calculated using the linear trapezoidal method to the last time point with a concentration above the qualified limit of quantitation.

For patients administered 0.2-mg/kg/week, the mean values for $AUC_{0-t}$ were relatively consistent from Week 1 through Week 24 (10,009±5,107 at Week 1, 11,232±3,914 at Week 2, 13,812±9,230 at Week 12, and 13,812±9,230 at Week 24). For the 1.0 mg/kg/week cohort, the mean values for AUC were 94,476±13,785 at Week 1, 180,909±46,377 at Week 2, 157,890±45,386 at Week 12 and 251,907±201,747 at Week 24. For this, 1.0 mg/kg/week group the increase in values for $AUC_{0-t}$ and $AUC_\infty$ and large standard deviation was due to a single patient whose AUCs were about 2-fold higher than the other two patients in the group.

Comparison of the mean values for $AUC_{0-t}$ between the 0.2 and 1.0 mg/kg/week cohorts showed an increase far in excess of the 5-fold increase in dose, indicating that the pharmacokinetics of rhASB are not linear over this dose range.

Pharmacokinetic parameters at Weeks 83, 84 and 96 are shown in Table 27 below.

TABLE 27

| Parameter | Week 83 | Week 84 | Week 96 |
| --- | --- | --- | --- |
| Cmax (ng/mL) | 1,143 ± 284 | 1,367 ± 262 | 1,341 ± 523 |
| Tmax (min) | 180 | 120 | 121 |
| $AUC_{0-t}$ (min · ng/mL) | 172,423 ± 49,495 | 213,713 ± 45,794 | 200,116 ± 76,506 |
| $AUC_\infty$ (min · ng/mL) | 173,570 ± 49,969 | 215,383 ± 47,018 | 201,157 ± 77,248 |

TABLE 27-continued

| Parameter | Week 83 | Week 84 | Week 96 |
| --- | --- | --- | --- |
| CL (mL/min/kg) | 6.23 ± 2.10 | 4.81 ± 0.99 | 5.54 ± 2.09 |
| Vz (mL/kg) | 67.6 ± 22.0 | 122 ± 60.2 | 123 ± 17.4 |
| Vss (mL/kg) | 266 ± 52.3 | 236 ± 21.1 | 233 ± 27.6 |
| t½ (min), half-life | 8.49 ± 4.68 | 19.0 ± 13.2 | 17.3 ± 8.26 |
| MRT (min) | 44.4 ± 7.61 | 50.9 ± 12.9 | 46.1 ± 16.1 |

Arithmetic mean and standard deviation are reported except for Tmax which is the median. Individual patient values were reported if n < 3.

Parameters for Week 83 were comparable to those obtained from Weeks 2 through 24 (excluding one patient with high AUCs), indicating consistency in rhASB pharmacokinetics after weekly exposure for approximately 18 months. From Week 83 to Week 84, mean AUC values trended upward by approximately 25% while total body clearance trended downward by approximately 25%. From Week 83 to Week 84, the half-life increased from about 8.5 minutes to 17–19 minutes. Parameters from Week 96 were comparable to those from Week 84. Although this pharmacokinetic data was from a small number of patients and there was substantial overlap of individual values, these results indicated that the high purity rh ASB preparation obtained from the modified process described in Example 9 had a longer half-life than the original rhASB preparation.

EXAMPLE 12

Further Clinical Study in Humans

A Phase 2 open-label clinical trial of recombinant human N-acetylgalactosamine-4-sulfatase (rhASB) in patients with mucopolysaccharidosis VI (MPS VI), Maroteaux-Lamy Syndrome, was conducted using drug product produced according to the new perfusion process described in Example 9. The rhASB was formulated at a concentration of 1 mg/mL, pH 5.8, 9 mM sodium phosphate, monobasic, 1 $H_2O$, 1 mM sodium phosphate, dibasic, 7 H20, 150 mM sodium chloride, 0.005% polysorbate 80.

The objectives of this study were to evaluate the safety, efficacy and pharmacokinetics of 1.0 mg/kg rhASB given as a weekly IV infusion. The inclusion criteria were modified for this study to include a relatively uniform set of patients with impaired endurance. Patients had to be able to walk at least 1 m but no more than 250 min the first six minutes of a 12-minute walk test at baseline. The other inclusion and exclusion criteria were similar to those of the Phase 1/2 Study in that patients had to be at least five years old and have a documented biochemical or genetic diagnosis. In addition to the walk test, a number of endpoints not previously studied in MPS patients were included in this study.

Measures of safety included clinical laboratory evaluations, urinalysis, CBC with differential, ECG and tracking of AEs. Infusion-associated reactions as well as complement consumption and antibody formation are being assessed for all patients. Efficacy parameters included measures of endurance and mobility, including a 12-minute walk test, the Expanded Timed Get Up and Go test, the 3-minute stair climb test and physical activity. Subjective effects, such as joint pain and joint stiffness, were assessed with a questionnaire, and other measures in the Denver Developmental scale such as time to tie shoes, touch top of head, pull over sweater, and pick up coins and put them in a cup were also assessed. Additional efficacy measures included measures of visual acuity, bone density studies, assessment of grip and pinch strength, shoulder ROM, functional status, pulmonary function, urinary GAG excretion, visual exams, cardiac function, and oxygen saturation during sleep. Pharmacokinetic evaluations were conducted during infusions at Weeks 1, 2, 12 and 24 to measure antigen (enzyme) levels during and after infusion. Ten patients were enrolled—five in the U.S. and five in Australia. All patients completed Week 24 of treatment. There were no deaths or discontinuations. All patients received all 24 study drug infusions; therefore, all patients were included in the safety and efficacy analyses.

As in the Phase 1/2 study, there was wide heterogeneity of disease severity among the MPS VI patients enrolled in the Phase 2 Study. Several patients also had neurological features of the disease, including communicating hydrocephalus, cervical spine instability, and spinal disc disease.

Clinical Laboratory Assessments

No clinically significant laboratory abnormalities Were observed in these patients over the 24-week period.

Anti-rhASB Antibodies and Complement Studies

Figure 14:
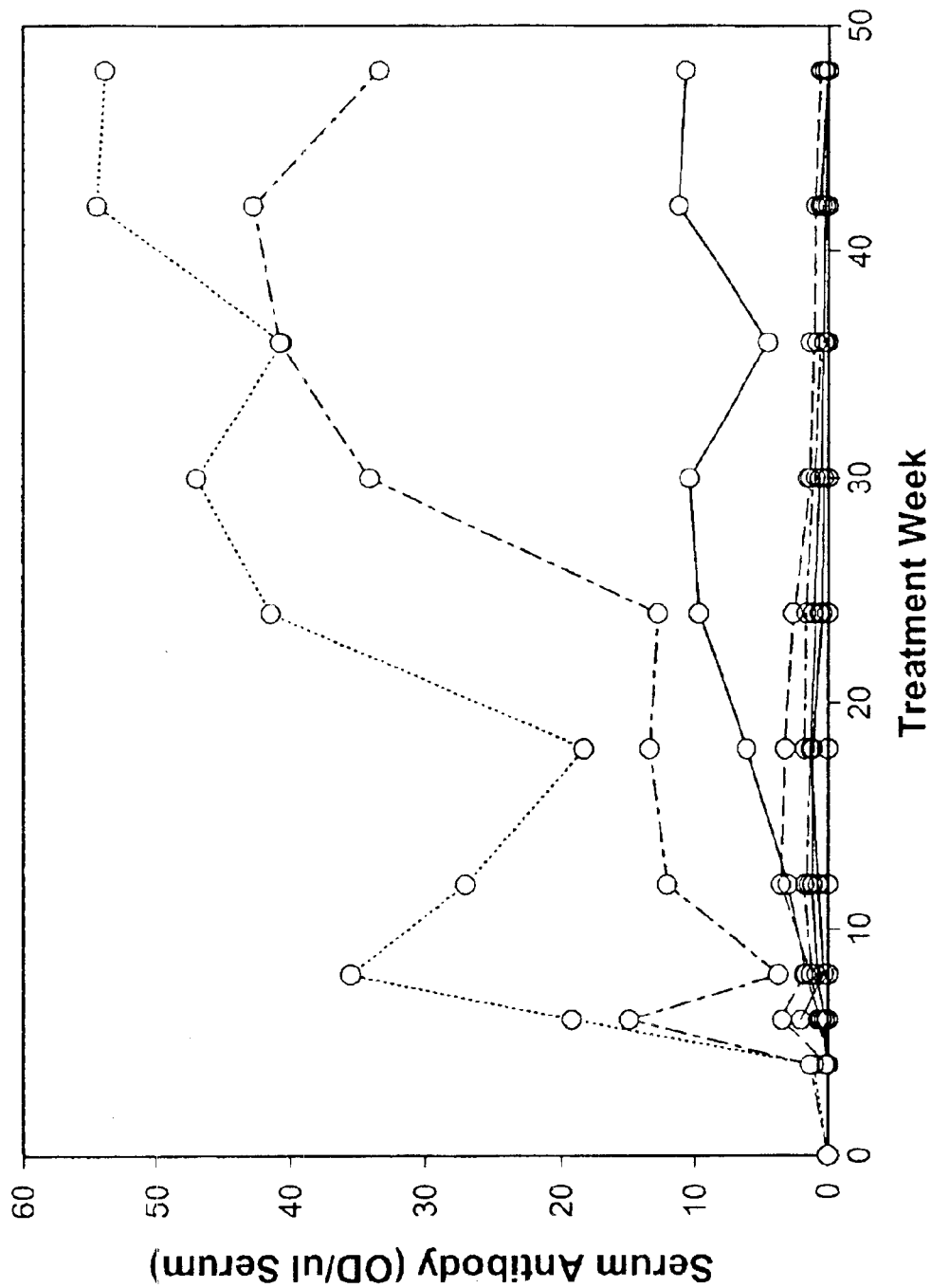
FIG. 14 shows serum anti-ASB antibody levels over 48 weeks of treatment in a Phase 2 clinical study in humans.

Eight of the 10 patients developed antibody to rhASB by Week 24. Of the three patients that developed higher levels of antibody than the other patients, two patients' antibody levels continued to rise after Week 24 but appeared to have stabilized by Week 48. These two patients were either the "null" genotype or had a mutation in the presumed major antigenic site for ASB. The reduction in urinary GAGs was less for these two patients compared to the others. FIG. 14 shows antibody levels over 48 weeks of treatment.

At Week 24, one patient had decreased C4 and CH50 values, both pre- and post-Week 12 infusion, which were considered to be clinically significant by the investigator. C4 and CH50 were slightly below the lower limit of normal prior to infusion and showed a greater decrease following the infusion. Although these results suggested the possibility of complement consumption, no clinical signs or symptoms consistent with such consumption were observed. Clinically significant abnormalities in complement levels were not observed in any of the other patients in the study.

Urinary Glycosaminoglycans

Figure 15:
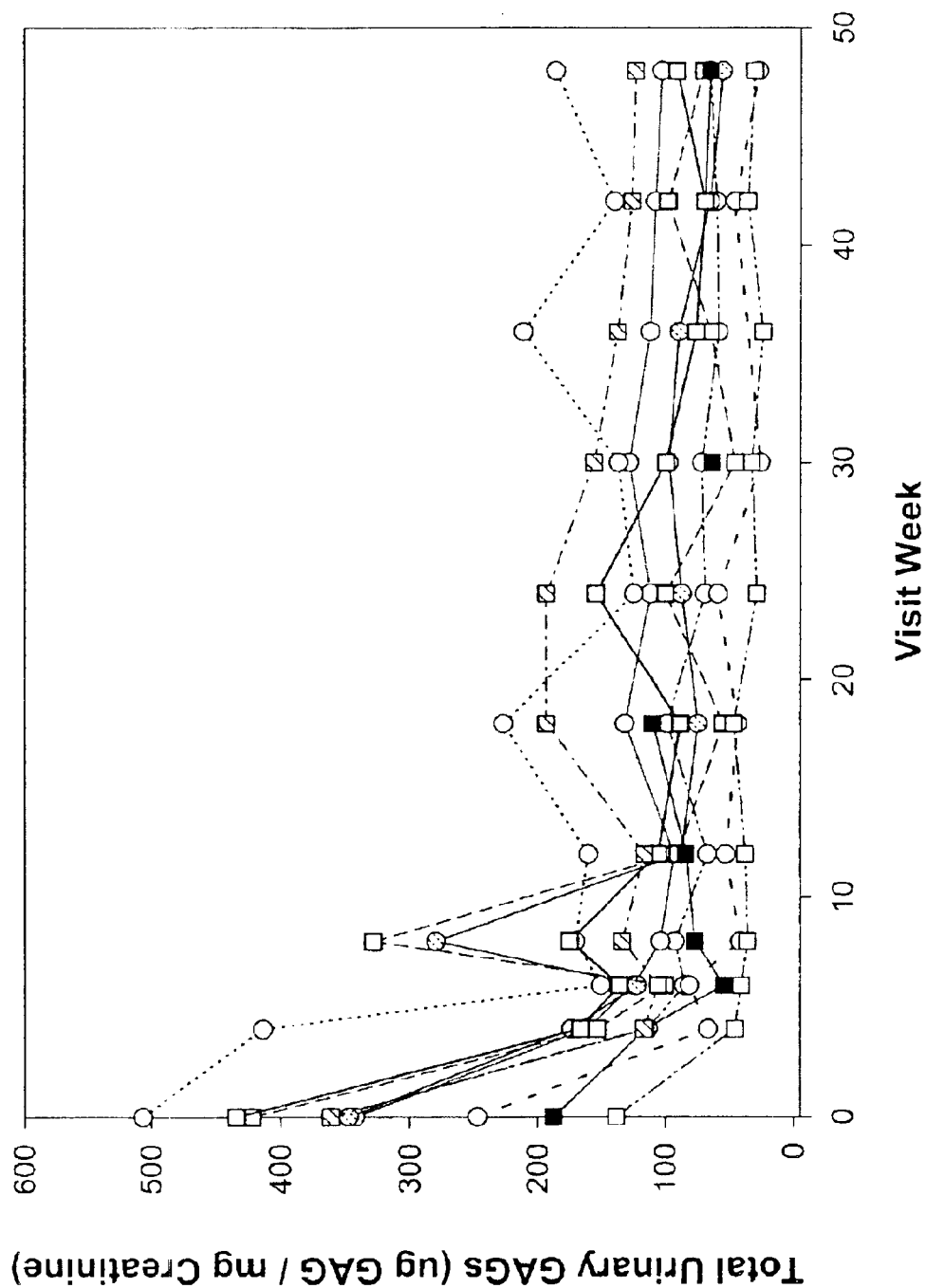
FIG. 15 shows the reduction in total urinary GAG levels over 48 weeks of treatment in a Phase 2 clinical study in humans.
Figure 16:
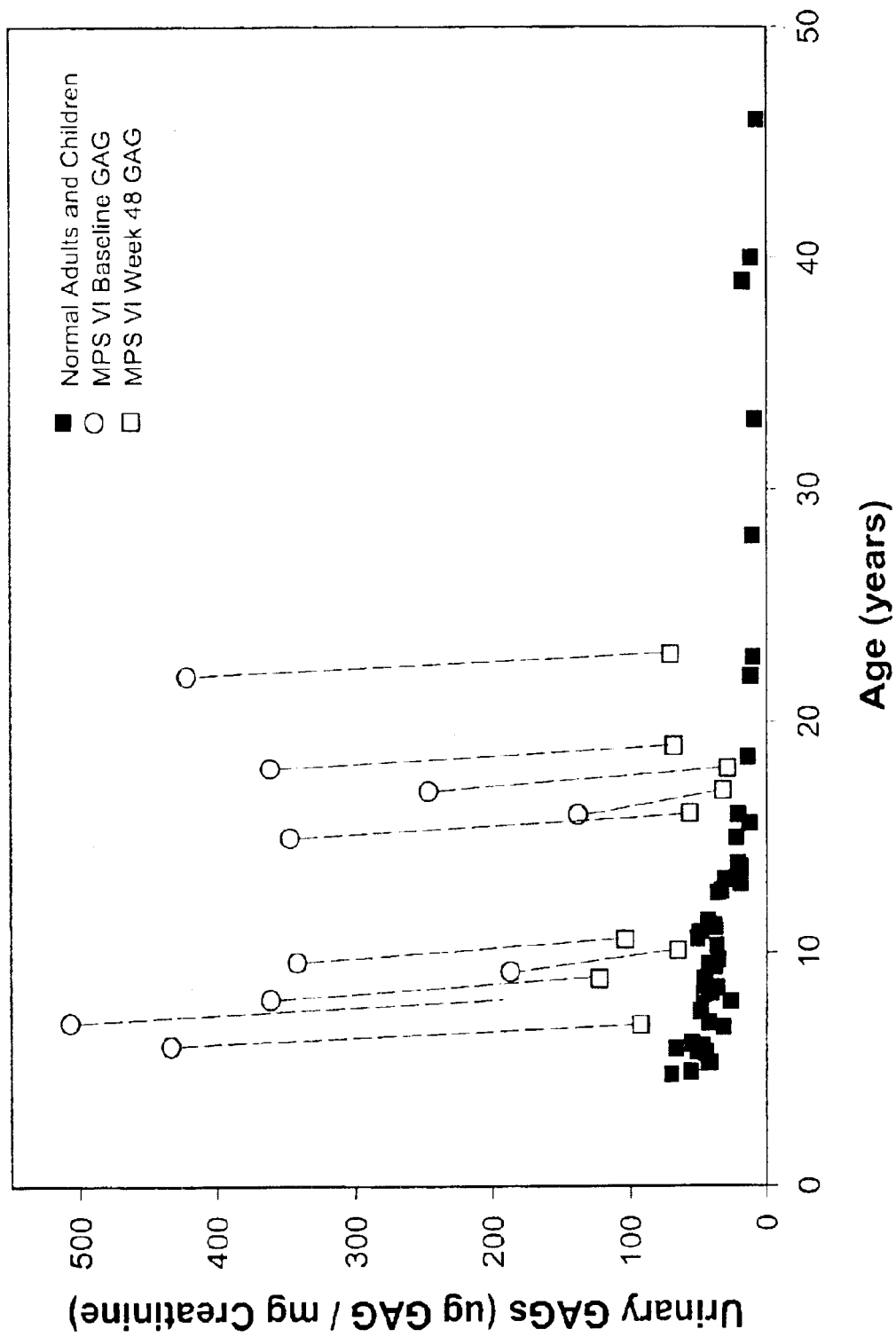
FIG. 16 shows a comparison of levels at week 48 in humans treated with rhASB to age-appropriate normal levels.

The mean reduction in urinary GAG levels was rapid, reaching a nadir at Week 6 and remaining relatively constant from Week 6 through Week 24. By Week 24, urinary GAGs were reduced by an average of 71%, and by Week 48 urinary GAGs were reduced by an average of 76%. All ten patients showed a decrease in urinary GAG levels that approached the normal range after 24 weeks of treatment. These data are consistent with the results seen for the seven patients in the Phase 1/2 stud. FIG. 15 shows the reduction in total urinary GAG levels over the 48 weeks and FIG. 16 shows a comparison of levels at week 48 to age appropriate normal levels.

Measures of Endurance

Figure 17:
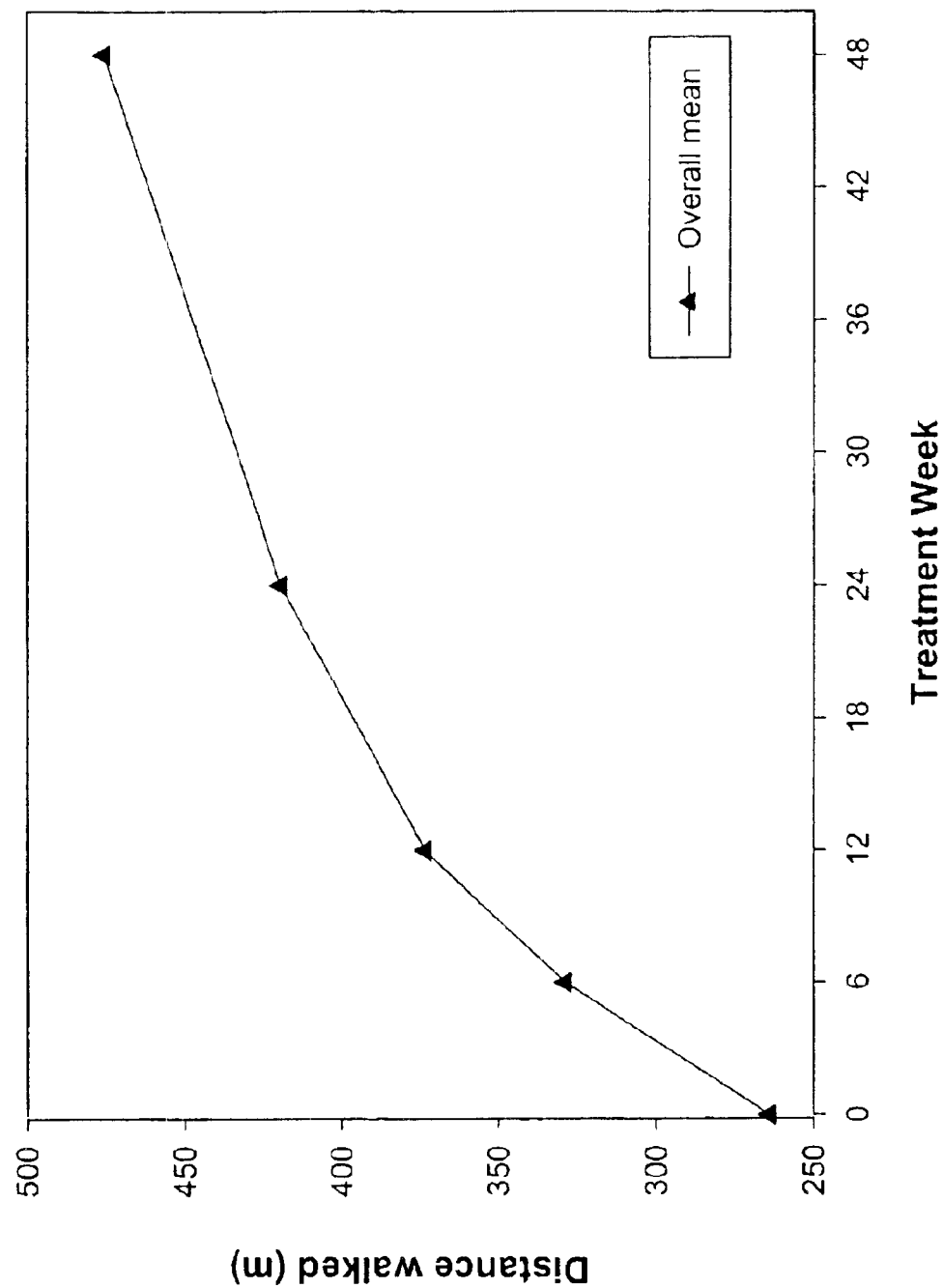
FIG. 17 shows the improvement in the 12-minute walk test results over 48 weeks of treatment in a Phase 2 clinical study in humans.

Distance walked was assessed in a 12-minute walk test for all patients at baseline and every six weeks thereafter. Distance was recorded as the mean of two separate measures at each evaluation and was determined at both 6 minutes and 12 minutes;

At baseline, the mean distances walked at 6 and 12 minutes were 152.4 (±75.0) and 264.0 (±161.7) meters, respectively. At Week 24 the mean distance walked at 6 minutes had improved by 57.3 (±59.0) meters (62% per patient), while the mean distance walked at 12 minutes had improved by an average of 155 meters (98% per patient). All patients improved their distance walked at 12 minutes, and all but one patient improved in the first 6 minutes of the walk. At Week 48, the average improvement in the 12-minute walk test was 212 meters (138% per patient). FIG. 17 shows the improvement in the 12-minute walk test results over the 48 weeks.

Figure 18:
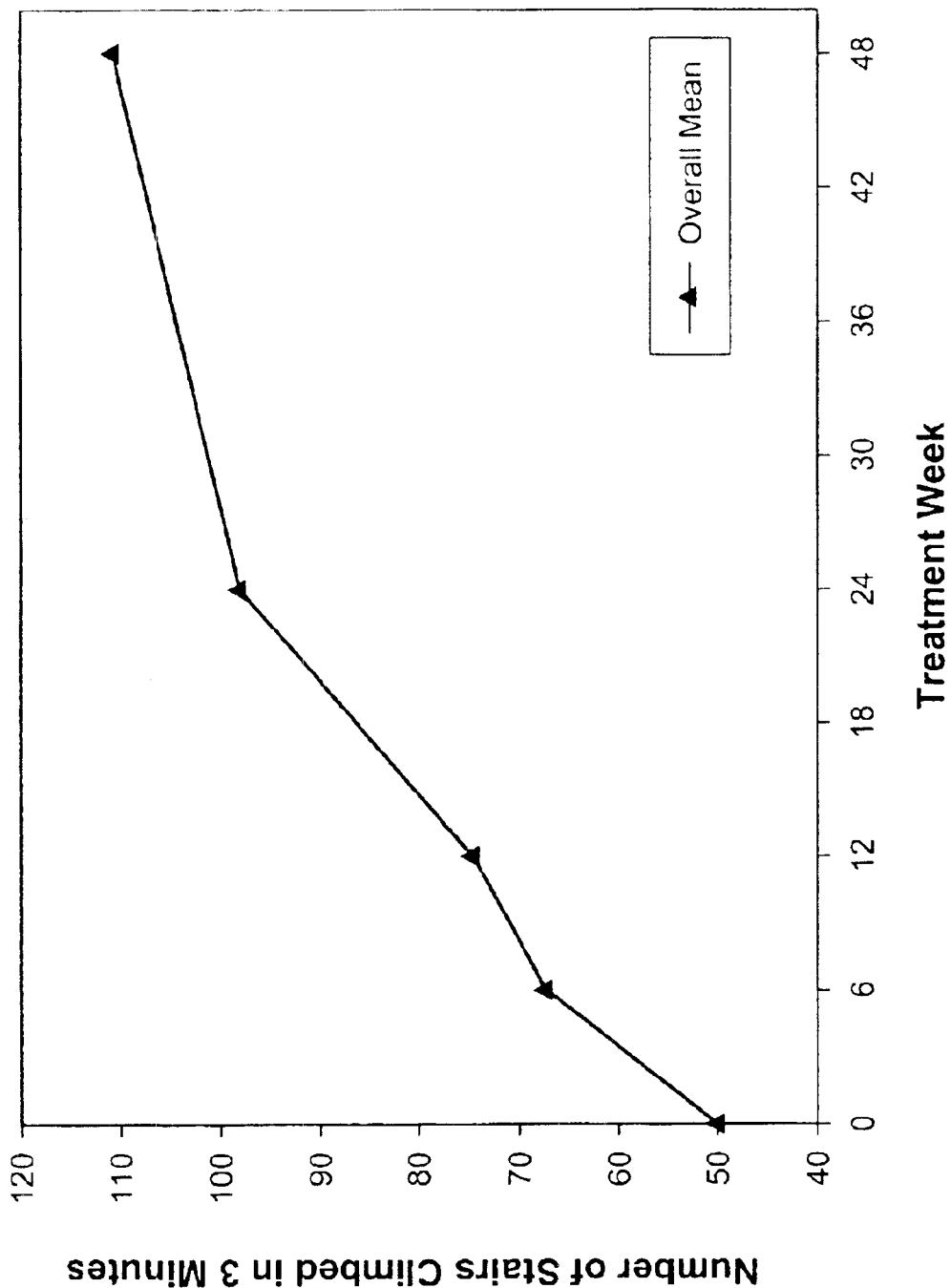
FIG. 18 shows the improvement in the 3-minute stair climb results over 48 weeks of treatment in a Phase 2 clinical study in humans.

The 3-minute stair climb was the second measure of endurance tested. At baseline, patients could climb a mean of 50.3 (±29.5) stairs. By 24 weeks, the mean number of stairs climbed had increased to 98.1 (±62.5) stairs, an improvement of 48 stairs or 110% per patient. (±116%). By 48 weeks, the average number of stairs climbed had increased by 61 stairs to a total of 111 stairs, an improvement of 147% per patient. FIG. 18 shows the improvement in the 3-minute stair climb results over the 48 weeks. Patients varied greatly in terms of the number of stairs climbed, and performance at baseline did not necessarily correlate with the degree of improvement at Week 24.

Additional Efficacy Measures

Figure 19:
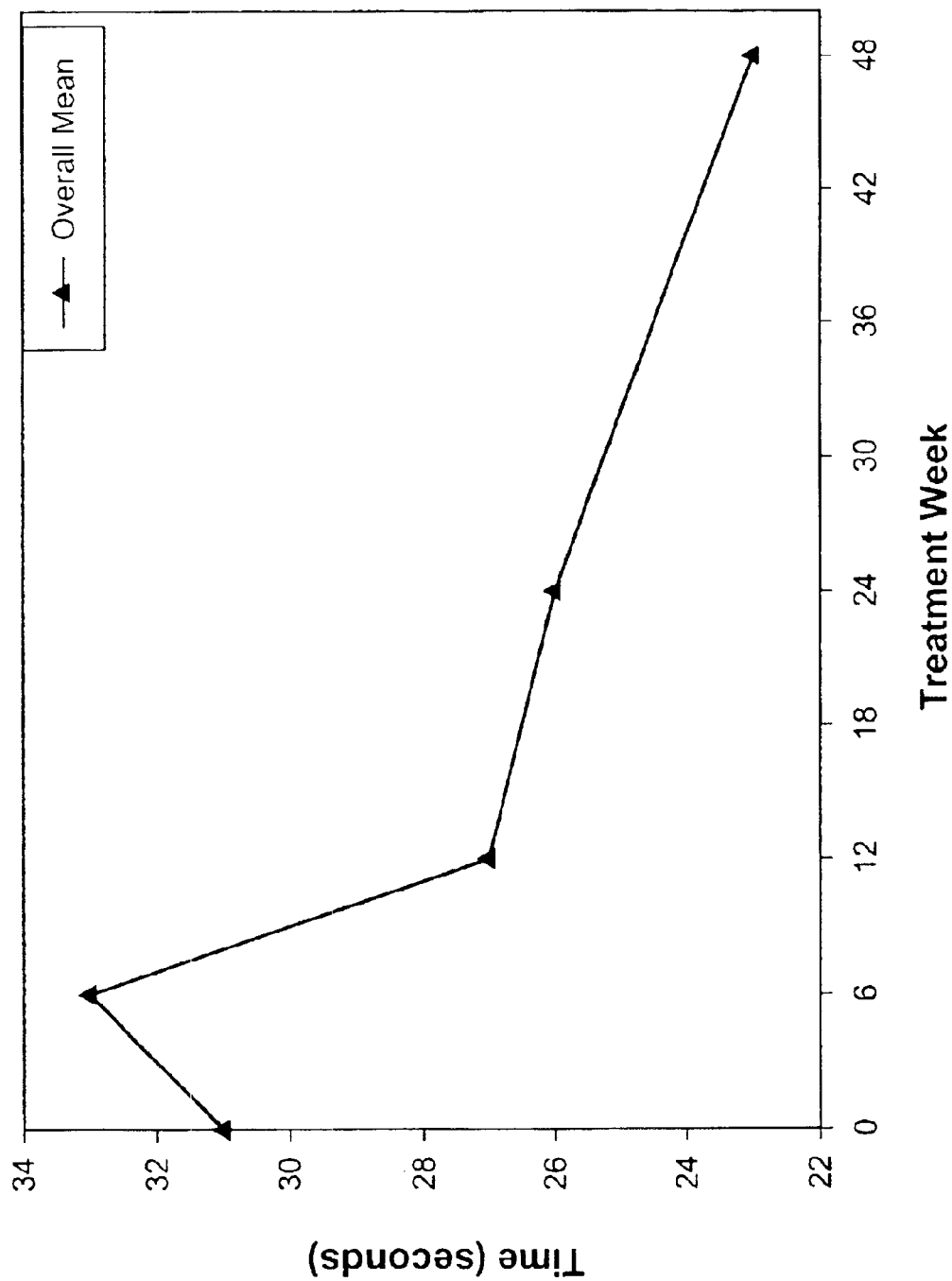
FIG. 19 shows results of the Expanded Timed Get Up and Go Test over 48 weeks of treatment in a Phase 2 clinical study in humans.

A number of additional efficacy parameters were evaluated during the first 24 weeks of this study. The Expanded Timed Get Up and Go Test was used as a measure of general functional ability. Overall, there was no significant reduction in total time needed for this test between baseline and Week 24, but there was a modest improvement by Week 48. FIG. 19 shows results of the Expanded Timed Get Up and Go Test over 48 weeks of treatment.

Forced Expiratory Time (FET), FVC and FEV1 were performed to assess pulmonary function. Table 28 below displays pulmonary function values at baseline, Week 24 and Week 48 and also shows improvement in height and organomegaly at Week 48. No significant changes in these parameters were seen over the 24-week period. At Week 48, 5/10 patients improved in FVC and FEV1, of whom 3 of the 5 showed improvement despite less than 2% change in growth. At Week 48 there was also an average 43% improvement in Forced Expiratory Time (>1 second).

TABLE 29

Shoulder Range of Motion

| Shoulder Motion | Baseline | Change @ Week 24 (degrees of function) | Change @ Week 48 |
|---|---|---|---|
| All patients (n = 10) | | | |
| Active Flexion | 102 | 6 | 3 |
| Passive Flexion | 116 | 4 | (1) |
| Active Extension | 52 | 5 | 5 |
| Passive Extension | 63 | 9 | (6) |
| Active Lateral Rotation | 59 | 7 | 6 |
| Passive Lateral Rotation | 69 | 9 | (6) |
| Patients with baseline flexion <90° (n = 3) | | | |
| Active Flexion | 85 | 9 | 5 |
| Active Extension | 50 | 6 | 4 |
| Active Lateral Rotation | 52 | 7 | 7 |

Table X2

Shoulder ROM (flexion, extension, rotation) was assessed both actively and passively. Overall for the group, a modest percent increase was seen in both active and passive ROM; however, some patients showed a decrease in some measures at 24 weeks. At 48 weeks, there was great variability in results due to several outliers; however, there continued to be improvement seen in shoulder ROM particularly in patients that had less than 90 degrees of flexion at baseline. Table 29 above displays the degrees of shoulder range of motion at baseline, Week 24 and Week 48.

Figure 20:
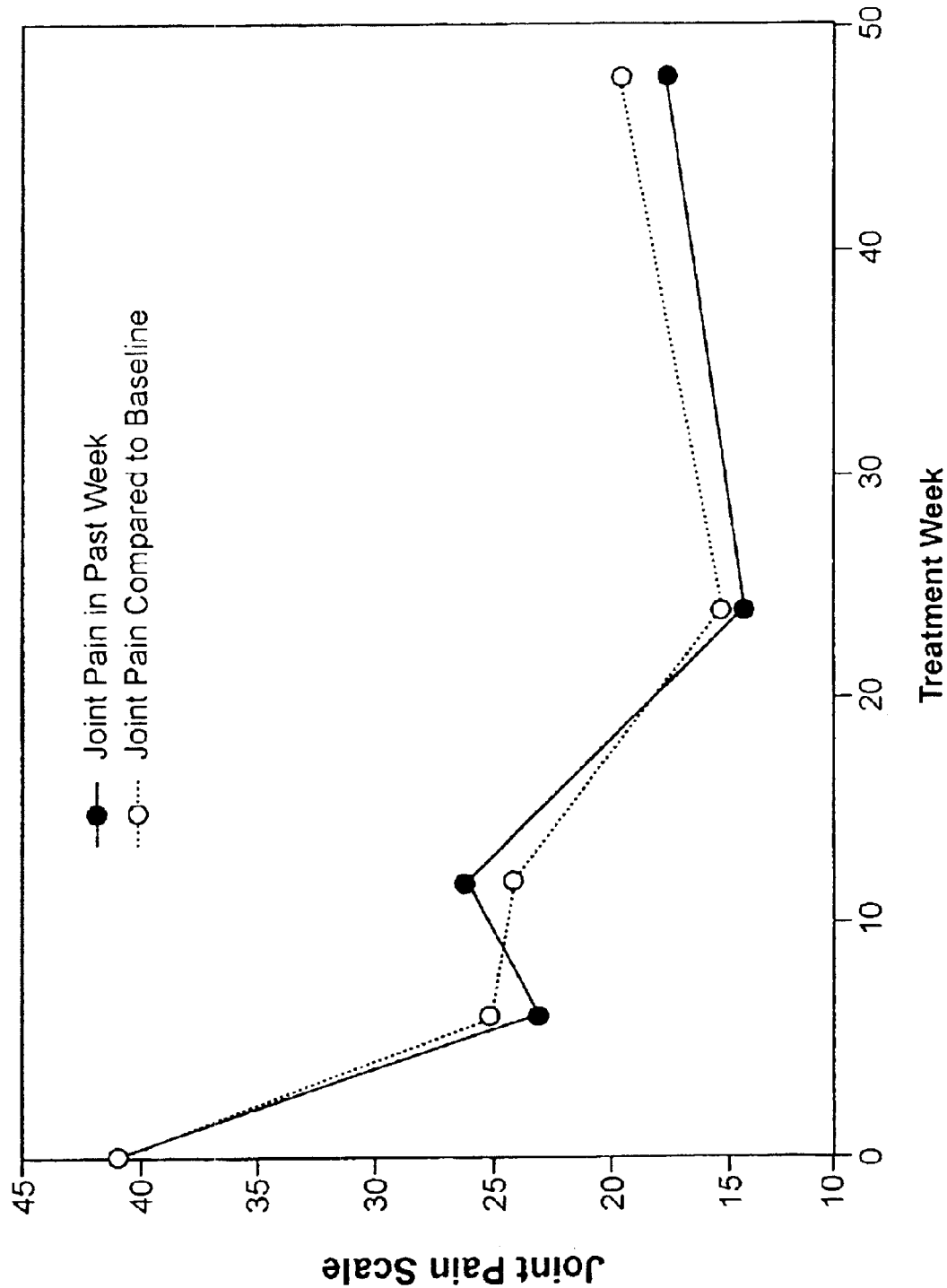
FIGS. 20 and 21, respectively, show results of joint pain and joint stiffness questionnaires over 48 weeks of treatment in a Phase 2 clinical study in humans.
Figure 21:
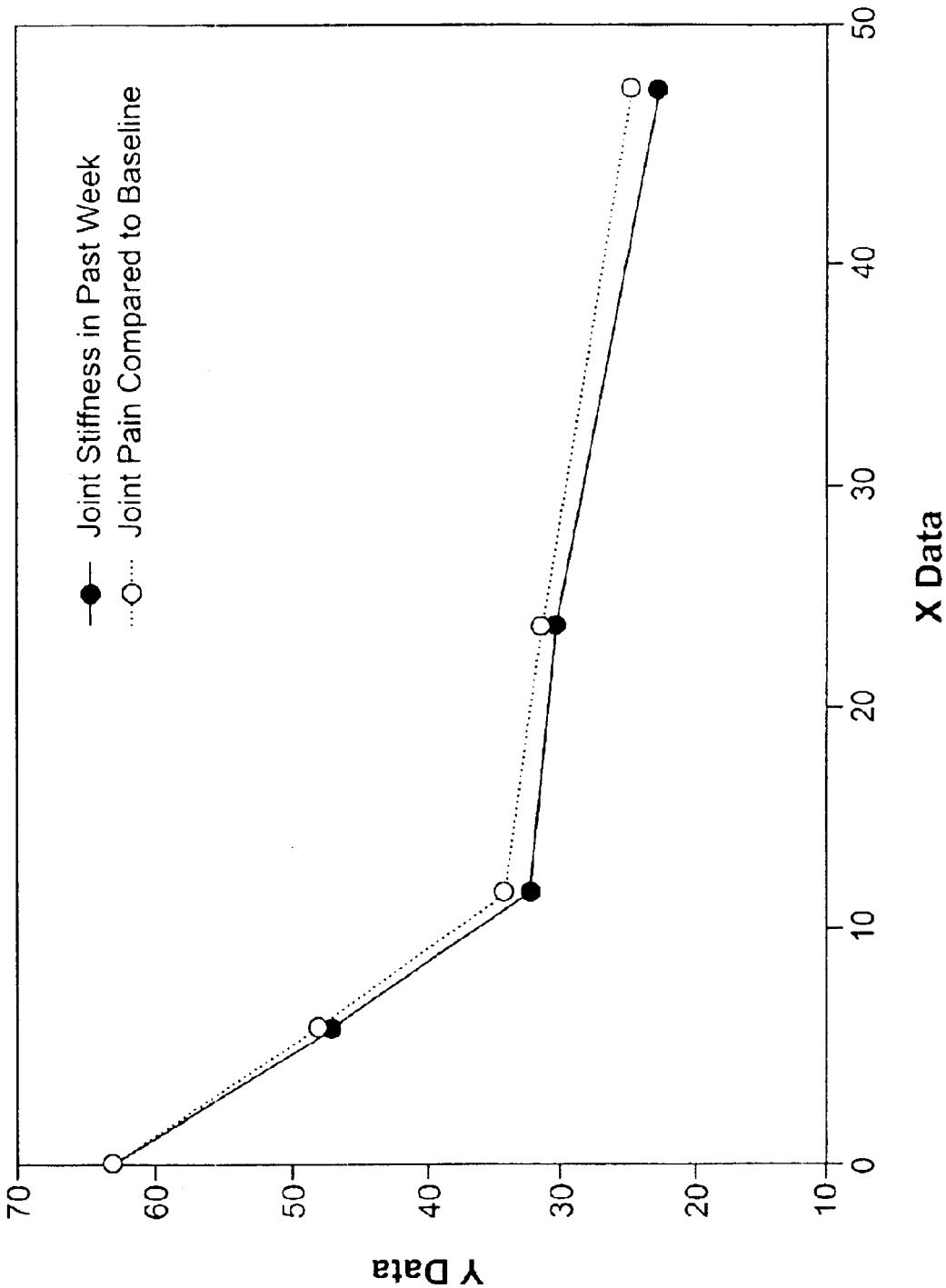

Pain and stiffness were assessed using a questionnaire: While two patients had no change in pain score, seven patients showed improvement in pain by Week 24 (one patient had no baseline evaluation). All of the nine patients evaluated showed improvement in stiffness at Week 24. Pain and stiffness evaluated using the questionnaire continued to improve by Week 48. Results of the joint pain questionnaire and joint stiffness questionnaire over 48 weeks of treatment are shown in FIGS. 20 and 21, respectively.

TABLE 28

Pulmonary Function versus Growth & Organomegaly

| Patient | Age | Baseline Height (cm) | Baseline FVC (liters) | Wk 24 FVC | Wk 48 FVC[1] | Change in Height [cm] (%) | % Δ Liver Wk 48[2] | Relative % Δ Liver Wk 48 | % Δ Spleen Wk 48[3] | Relative % Δ Spleen Wk 48 |
|---|---|---|---|---|---|---|---|---|---|---|
| 200 | 18 | 96.2 | 0.47 | 0.44 | 0.48 | −0.05 (<1) | −6.3 | −15.2* | −5.88 | −13.90 |
| 201 | 9 | 93.2 | 0.52 | 0.54 | 0.60 | 6.65 (7.1) | −2.3 | −14.4* | −8.82 | −20.17 |
| 202 | 17 | 120 | 0.75 | ND | 0.92 | 0.55 (<1) | −6.7 | −5.3 | −27.81 | −26.69 |
| 203 | 15 | 107 | 0.28 | 0.27 | 0.38 | 1.9 (1.8) | −8.6 | −12.5 | −16.45 | −20.22 |
| 204 | 7 | 87 | 0.52 | 0.60 | 0.50 | 3.8 (4.4) | −1.3 | −4.5 | −6.74 | −9.71 |
| 300 | 22 | 102.4 | 0.37 | 0.39 | 0.37 | 2.5 (2.4) | −15.5 | −20* | −16.58 | −21.09 |
| 301 | 9 | 121.1 | 1.40 | 1.46 | 1.55 | 4.9 (4.0) | +26.3 | +3 | 19.67 | −2.56 |
| 302 | 6 | 99.7 | 0.81 | 0.85 | 0.83 | 4.8 (4.8) | +5.7 | −13 | −1.92 | −19.99 |
| 303 | 8 | 84.6 | 0.16 | 0.27 | 0.31 | 1.1 (1.3) | −5.8 | −13+ | −45.33 | −49.38 |
| 304 | 16 | 124.7 | 0.83 | 0.74 | 0.83 | 1.3 (1.0) | −2.8 | −15* | 6.93 | −6.03 |

[1]Bolded values indicate FVC values that represent clinically meaningful increases
[2]mean liver size at baseline 681.6 ± 118 cc
[3]mean spleen size at baseline 146.8 ± 40 cc
*Liver volumes above 95% limit age-adjusted to body weight at baseline, and within normal limits at week 48
+Liver volumes above 95% limit age-adjusted to body weight at baseline and week 48

Significant improvements in grip strength were seen across the entire group of patients. Seven patients had improvements in grip strength for one or both hands. Little change was seen in the pinch test over the 24-week period. There was little significant change seen in the other quality of life assessments, except that at Week 48, there was a modest improvement in Dexterity and Sensation (as measured by the coin pick-up test).

Activity levels were measured using the belt-attached ActiTrac® device. No significant changes in activity level were observed.

No significant changes were observed in cardiac function assessments (ECGs) or in standing height and supine length. Sleep studies performed in a subset of patients showed no clinically significant changes.

Although the invention has been described with reference to the presently preferred embodiments, it should be understood that various modifications can be made without departing—from the spirit of the invention. Accordingly, the invention is limited only by the following claims.

What is claimed is:

1. A method for treating mucopolysaccharidosis VI (MPS VI) or Maroteaux-Lamy syndrome comprising the step of administering to a human subject an effective amount of a composition comprising recombinant human N-acetylgalactosamine-4-sulfatase (rhASB) at a dose of at least 0.2 mg/kg per week.

2. The method of claim 1 wherein the rhASB is administered at a dose of at least 1 mg/kg per week.

3. The method of claim 1 wherein the rhASB is administered at a dose of at least 2 mg/kg per week.

4. The method of claim 1, 2 or 3 wherein the rhASB is administered via a once weekly infusion over a period of 2 to 4 hours.

5. The method of claim 4 wherein the rhASB is administered via a once weekly infusion over a period of 4 hours.

* * * * *

UNITED STATES PATENT AND TRADEMARK OFFICE
CERTIFICATE OF CORRECTION

PATENT NO.    : 6,972,124 B2
DATED         : December 6, 2005
INVENTOR(S)   : Qin et al.

It is certified that error appears in the above-identified patent and that said Letters Patent is hereby corrected as shown below:

Title page,
Item [75], Inventors, delete "Stuart Sweidler" and insert -- Stuart Swiedler --.
Item [73], Assignee, delete "BioMarin Pharmaceuticals Inc." and insert -- BioMarin Pharmaceutical Inc. --.

Signed and Sealed this

Eighteenth Day of April, 2006

JON W. DUDAS
*Director of the United States Patent and Trademark Office*